US011535679B2

(12) United States Patent
Elliott et al.

(10) Patent No.: US 11,535,679 B2
(45) Date of Patent: Dec. 27, 2022

(54) BISPECIFIC ANTIBODY AGAINST CD3 AND CD20 IN COMBINATION THERAPY FOR TREATING FOLLICULAR LYMPHOMA

(71) Applicant: GENMAB A/S, Copenhagen V (DK)

(72) Inventors: Brian Elliott, Hoboken, NJ (US); Tahamtan Ahmadi, Rydal, PA (US); Christopher W. L. Chiu, Warren, NJ (US); Esther C. W. Breij, Driebergen (NL)

(73) Assignee: GENMAB A/S, Copenhagen V (DK)

( * ) Notice: Subject to any disclaimer, the term of this patent is extended or adjusted under 35 U.S.C. 154(b) by 0 days.

(21) Appl. No.: 17/558,404

(22) Filed: Dec. 21, 2021

(65) Prior Publication Data

US 2022/0112300 A1    Apr. 14, 2022

Related U.S. Application Data

(63) Continuation of application No. 17/472,143, filed on Sep. 10, 2021, now abandoned.

(60) Provisional application No. 63/076,792, filed on Sep. 10, 2020.

(51) Int. Cl.
| | |
|---|---|
| *C07K 16/28* | (2006.01) |
| *A61P 35/00* | (2006.01) |
| *A61K 31/4184* | (2006.01) |
| *A61K 39/00* | (2006.01) |

(52) U.S. Cl.
CPC ...... *C07K 16/2887* (2013.01); *A61K 31/4184* (2013.01); *A61P 35/00* (2018.01); *A61K 2039/505* (2013.01); *A61K 2039/545* (2013.01)

(58) Field of Classification Search
CPC ............ C07K 16/2887; C07K 16/2809; C07K 2317/31; A61K 2300/00; A61K 45/06; A61K 2039/505; A61K 2039/545
See application file for complete search history.

(56) References Cited

U.S. PATENT DOCUMENTS

| | | | |
|---|---|---|---|
| 5,736,137 A | 4/1998 | Anderson et al. | |
| 7,375,118 B2 | 5/2008 | Sircar et al. | |
| 8,236,308 B2 | 8/2012 | Kischel et al. | |
| 9,150,663 B2 | 10/2015 | Labrijn et al. | |
| 9,212,230 B2 | 12/2015 | Schuurman et al. | |
| 10,273,227 B2 | 4/2019 | Kettle et al. | |
| 10,344,050 B2 | 7/2019 | Gramer et al. | |
| 10,407,501 B2 | 9/2019 | Van Den Brink et al. | |
| 10,465,006 B2 | 11/2019 | Van Den Brink et al. | |
| 10,544,220 B2 | 1/2020 | Engelberts et al. | |
| 10,590,206 B2 | 3/2020 | Labrijn et al. | |
| 10,597,464 B2 | 3/2020 | Labrijn et al. | |
| 10,906,991 B2 | 2/2021 | Schuurman et al. | |
| 2010/0105874 A1 | 4/2010 | Schuurman et al. | |
| 2011/0275787 A1 | 11/2011 | Kufer et al. | |
| 2013/0039913 A1 | 2/2013 | Labrijn et al. | |
| 2013/0216556 A1 | 8/2013 | Fowler et al. | |
| 2014/0088295 A1 | 3/2014 | Smith et al. | |
| 2014/0303356 A1 | 10/2014 | Gramer et al. | |
| 2015/0166661 A1 | 6/2015 | Chen et al. | |
| 2015/0337049 A1 | 11/2015 | Labrijn et al. | |
| 2016/0046727 A1 | 2/2016 | Labrijn et al. | |
| 2016/0159930 A1 | 6/2016 | Schuurman et al. | |
| 2016/0168247 A1 | 6/2016 | Van Den Brink et al. | |
| 2016/0199399 A1 | 7/2016 | Knudsen | |
| 2016/0333095 A1 | 11/2016 | Van Den Brink et al. | |
| 2017/0233497 A1 | 8/2017 | Labrijn et al. | |
| 2017/0355767 A1 | 12/2017 | Engelberts et al. | |
| 2018/0134798 A1 | 5/2018 | Chu et al. | |
| 2020/0048304 A1 | 2/2020 | Gramer et al. | |
| 2020/0123255 A1 | 4/2020 | Van Den Brink et al. | |
| 2020/0199229 A1 | 6/2020 | Van Den Brink et al. | |
| 2020/0199231 A1 | 6/2020 | Engelberts et al. | |
| 2020/0262932 A1 | 8/2020 | Labrijn et al. | |
| 2020/0332022 A1 | 10/2020 | Labrijn et al. | |
| 2021/0371538 A1* | 12/2021 | Ahmadi | C07K 16/2887 |
| 2022/0088070 A1 | 3/2022 | Albertson et al. | |
| 2022/0112287 A1 | 4/2022 | Elliott et al. | |
| 2022/0112301 A1 | 4/2022 | Elliott et al. | |
| 2022/0112309 A1 | 4/2022 | Elliott et al. | |
| 2022/0119544 A1 | 4/2022 | Elliott et al. | |
| 2022/0144964 A1 | 5/2022 | Elliott et al. | |

FOREIGN PATENT DOCUMENTS

| | | |
|---|---|---|
| CN | 104922688 A | 9/2015 |
| WO | 2004/035607 A2 | 4/2004 |
| WO | 2005/103081 A2 | 11/2005 |
| WO | 2007/042261 A2 | 4/2007 |
| WO | 2008/119353 A1 | 10/2008 |
| WO | 2008/119567 A2 | 10/2008 |

(Continued)

OTHER PUBLICATIONS

Friend et al (Transplantation, 1999, vol. 68, pp. 1632-1637) (Year: 1999).*
Seiler an Hiddemann (Current Opinion in Oncology, 2012, vol. 24, pp. 742-747) (Year: 2014).*
The abstractor Rummel et al (Blood, 2009, vol. 114, No. 22, abstract No. 405) (Year: 2009).*
Chen et a (Clinical Translational Science, 2019, vol. 12, pp. 600-608) (Year: 2019).*
Burger, J. et al., "Randomized trial of ibrutinib vs ibrutinib plus rituximab in patients with chronic lymphocytic leukemia," Blood, vol. 133(10):1011-1019 (2019).
Gramer, M. et al., "Production of stable bispecific IgG1 by controlled Fab-arm exchange Scalability from bench to large-scale manufacturing by application of standard approaches," mAbs, vol. 5(6): 962-973 (2013).

(Continued)

*Primary Examiner* — Karen A. Canella
(74) *Attorney, Agent, or Firm* — Nelson Mullins Riley & Scarborough LLP; Jane E. Remillard, Esq.; Christopher L. Frank

(57) ABSTRACT

Provided are methods of clinical treatment of follicular lymphoma (for example, relapsed and/or refractory follicular lymphoma) in human subjects using a bispecific antibody which binds to CD3 and CD20 in combination with standard of care regimens of rituximab and bendamustine.

27 Claims, 3 Drawing Sheets

Specification includes a Sequence Listing.

(56) References Cited

FOREIGN PATENT DOCUMENTS

| WO | 2008/145141 | A1 | 12/2008 | |
|---|---|---|---|---|
| WO | 2011014659 | A2 | 2/2011 | |
| WO | 2011/028952 | A1 | 3/2011 | |
| WO | 2011090762 | A1 | 7/2011 | |
| WO | 2011/131746 | A2 | 10/2011 | |
| WO | 2012162067 | A2 | 11/2012 | |
| WO | 2013/026833 | A1 | 2/2013 | |
| WO | 2013/060867 | A2 | 5/2013 | |
| WO | 2014/047231 | A1 | 3/2014 | |
| WO | 2014108483 | A1 | 7/2014 | |
| WO | 2014/131694 | A1 | 9/2014 | |
| WO | 2014/131711 | A1 | 9/2014 | |
| WO | 2015/001085 | A1 | 1/2015 | |
| WO | 2015006749 | A2 | 1/2015 | |
| WO | 2015/143079 | A1 | 9/2015 | |
| WO | 2016/081490 | A1 | 5/2016 | |
| WO | 2016/110576 | A1 | 7/2016 | |
| WO | 2017/210485 | A1 | 12/2017 | |
| WO | 2019/155008 | A1 | 8/2019 | |
| WO | WO-2021028587 | A1 * | 2/2021 | ............. A61P 35/00 |

OTHER PUBLICATIONS

Labrijn, A. et al., "Controlled Fab-arm exchange for the generation of stable bispecific IgG1," Nature Protocols, vol. 9 (10): 2450-63 (2014).

Sarkozy, C. et al., "Cause of Death in Follicular Lymphoma in the First Decade of the Rituximab Era: A Pooled Analysis of French and US Cohorts," J Clin Oncol., vol. 37:144-152. (2018).

Tam, C. et al., "Ibrutinib (Ibr) Plus Venetoclax (Ven) for First-Line Treatment of Chronic Lymphocytic Leukemia (CLL)/Small Lymphocytic Lymphoma (SLL): Results from the MRD Cohort of the Phase 2 Captivate Study," Blood, vol. 134 (Supplement_1): Abstract No. 35 (2019) Abstract Only, 8 pages.

Van der Horst, H. et al., "Duobody-CD3xCD20 Induces Potent Anti-Tumor Activity in Malignant Lymph Node B Cells from Patients with DLBCL, FL and MCL Ex Vivo, Irrespective of Prior Treatment with CD20 Monoclonal Antibodies," Blood, American Soc. of Hem., vol. 134(1): Abstract 4066: 4 pages (2019).

Van Der Neut Kolfschoten, M. et al., "Anti-Inflammatory Activity of Human IgG4 Antibodies by Dynamic Fab Arm Exchange," Science, vol. 317(5844):1554-1557 (2007).

Varadarajan I, et al., "Management of Cytokine Release Syndrome," Chimeric Antigen receptor T-cell therapies for Cancer, Chapter 5 :45-64 (2020).

VinCRIStine Sulfate Rx only Injection, USP, Retrieved on Feb. 9, 2022, www.accessdata.fda.gov/drugsatfda_docs/label/2014/071484s042lbl.pdf, 9 pages.

Wagner-Johnston, N. et al., "Outcomes of transformed follicular lymphoma in the modern era: a report from the National LymphoCare Study (NLCS)," Blood, vol. 126(7): 851-857 (2015).

Wierda, W et al., "Multivariable model for time to first treatment in patients with chronic lymphocytic leukemia," Journ Clin Oncol., vol. 29(31): 4088-4095 (2011).

Wolchok, J et al., "Guidelines for the evaluation of immune therapy activity in solid tumors: immune-related response criteria," Clin Cancer Res, vol. 15(23): 7412-7420 (2009).

Wu, C. et al., "Simultaneous targeting of multiple disease mediators by a dual-variable-domain immunoglobulin," Nat Biotechnol., vol. 25(11):1290-1297 (2007).

Xiong, D. et al., "Efficient inhibition of human B-cell lymphoma xenografts with an anti-CD20 x anti-CD3 bispecific diabody," Cancer Letters., vol. 177(1):29-39 (2002).

Zenz, T. et al., "From pathogenesis to treatment of chronic lymphocytic leukaemia," Nat Rev Cancer, vol. 10(1):37-50 (2010).

U.S. Appl. No. 14/934,956, filed Nov. 6, 2015, Janine Schuurman, U.S. Pat. No. 10,906,991.

U.S. Appl. No. 12/593,759, filed Jan. 6, 2010, U.S. Pat. No. 9,212,230.

U.S. Appl. No. 16/777,053, filed Jan. 30, 2020, Aran Frank Labrijn, US 2020-0262932.

U.S. Appl. No. 15/414,122, filed Jan. 24, 2017, Aran Frank Labrijn, U.S. Pat. No. 10,597,464.

U.S. Appl. No. 13/642,253, filed Oct. 24, 2012, Aran Frank Labrijn, U.S. Pat. No. 9,150,663.

U.S. Appl. No. 16/426,647, filed May 30, 2019, Michael Gramer, US 2020-0048304.

U.S. Appl. No. 14/353,962, filed Apr. 24, 2014, Michael Gramer, U.S. Pat. No. 10,344,050.

U.S. Appl. No. 16/783,720, filed Feb. 6, 2020, Aran Frank Labrijn, US 2020-0332022.

U.S. Appl. No. 14/760,157, filed Jul. 9, 2015, Aran Frank Labrijn, U.S. Pat. No. 10,590,206.

U.S. Appl. No. 16/582,428, filed Sep. 25, 2019 Edward Van Den Brink, US 2020-0123255.

U.S. Appl. No. 14/902,757, filed Jan. 4, 2016, Edward Van Den Brink, U.S. Pat. No. 10,465,006.

U.S. Appl. No. 16/544,376, filed Aug. 19, 2019, Edward Norbert Van Den Brink, US 2020-0199229.

U.S. Appl. No. 15/110,414, filed Jul. 8, 2016, Edward Norbert Van Den Brink, U.S. Pat. No. 10,407,501.

U.S. Appl. No. 16/702,996, filed Dec. 4, 2019, Patrick Engelberts, US 2020-0199231.

U.S. Appl. No. 15/541,594, filed Jul. 5, 2017, Patrick Engelberts, U.S. Pat. No. 10,544,220.

U.S. Appl. No. 17/559,935, filed Dec. 22, 2021, Brian Elliott.
U.S. Appl. No. 17/558,430, filed Dec. 21, 2021, Brian Elliott.
U.S. Appl. No. 17/559,938, filed Dec. 22, 2021, Brian Elliott.
U.S. Appl. No. 17/560,006, filed Dec. 22, 2021, Brian Elliott.
U.S. Appl. No. 17/559,965, filed Dec. 22, 2021, Brian Elliott.

Labrijn, AF et al., "Efficient generation of stable bispecific IgG1 by controlled Fab-arm exchange," PNAS, vol. 110 (13):5145-5150 (2013).

Lee, D et al., "ASTCT Consensus Grading for Cytokine Release Syndrome and Neurologic Toxicity Associated with Immune Effector Cells," Biol Blood Marrow Transplant, vol. 25(4): 625-638 (2019).

Leonard, J. P et al., "Augment: A Phase III Study of Lenalidomide Plus Rituximab Versus Placebo Plus Rituximab in Relapsed or Refractory Indolent Lymphoma," J Clin Oncol., vol. 37(14):1188-99 (2019).

Locke, F et al., "Long-term safety and activity of axicabtagene ciloleucel in refractory large B-cell lymphoma (ZUMA-1): a single-arm, multicentre, phase 1-2 trial," Lancet Oncol., vol. 20(1):31-42 (2019).

Mau-Soerensen, M. et al. "A phase I trial of intravenous catumaxomab: a bispecific monoclonal antibody targeting EpCAM and the T cell coreceptor CD32015," Cancer Chemother. Pharmacol., vol. 75(5): 1065-1073 (2015).

Morschhauser F. et al. "Rituximab plus Lenalidomide in Advanced Untreated Follicular Lymphoma" New England Journal of Medicine, vol. 379(10): 934-947 (2018).

Muller, D, et al., "Bispecific antibodies for cancer immunotherapy: Current perspectives," BioDrugs, vol. 24(2): 89-98 (2010).

Niemann, C et al., "Venetoclax and Ibrutinib for Patients with Relapsed/Refractory Chronic Lymphocytic Leukemia (R/R CLL)—15-Month Safety, Response and MRD Evaluation: Third Interim Analysis from the Phase II Vision HO141 Trial," Blood, vol. 134(1): Abstract 4292, 5 pages (2019).

Oganesyan V et al., "Structural characterization of a human Fc fragment engineered for lack of effector functions," Acta Cryst., (D64): 700-704 (2008).

Oken, M et al., "Toxicity and response criteria of the Eastern Cooperative Oncology Group," Am J Clin Oncol, vol. 5(6): 649-655 (1982).

Olejniczak, S et al., "A quantitative exploration of surface antigen expression in common B-cell malignancies using flow cytometry," Immunol Invest, vol. 35(1): 93-114 (2006).

Overdijk, M et al., "Crosstalk between human IgG isotypes and murine effector cells," J. Immunol., vol. 189(7): 3430-3438 (2012).

PARAPLATIN®, retrieved on Feb. 9, 2022 www.accessdata.fda.gov/drugsatfda_docs/label/2010/020452s005lbl.pdf, 21 pages.

(56) References Cited

OTHER PUBLICATIONS

Parren, P. et al., "Induction of T-cell proliferation by recombinant mouse and chimeric mouse/human anti-CD3 monoclonal antibodies," Res Immunol., vol. 142(9): 749-763 (1991).

Mondello, P. et al. "Bendamustine plus Rituximab Versus R-CHOP as First-Line Treatment for Patients with Follicular Lymphoma Grade 3A: Evidence from a Multicenter, Retrospective Study," The Oncologist, vol. 23(4):454-460 (2018).

Pedersen, I. et al., "The chimeric anti-CD20 antibody rituximab induces apoptosis in B-cell chronic lymphocytic leukemia cells through a p38 mitogen activated protein-kinase-dependent mechanism," Blood, vol. 99(4): 1314-1319 (2002).

Perks, B. et al., "Bispecific antibodies direct the immune system against blood; cancers," The Pharmaceutical Journal, URI: 20068566: 2 pages (2015).

Prescribing Information for Cyclophosphamide, Retrieved on Feb. 9, 2022, www.accessdata.fda.gov/drugsatfda_docs/label/2013/012141s090,012142s112lbl.pdf, 18 pages.

Prescribing Information for Eloxatin Retrieved on Feb. 9, 2022, www.accessdata.fda.gov/drugsatfda_docs/label/2020/021759s023lbl.pdf, 42 pages.

Prescribing Information for Gemzar, Retrieved on Feb. 9, 2022, www.accessdata.fda.gov/drugsatfda_docs/label/2014/020509s077lbl.pdf 18 pages.

Prescribing Information For Infugem, Retrieved on Feb. 9, 2022, www.accessdata.fda.gov/drugsatfda_docs/label/2018/208313Orig1s000lbl.pdf, 30 pages.

Prescribing Information for Rituxan®, Retrieved on Feb. 9, 2022, www.accessdata.fda.gov/drugsatfda_docs/label/2013/103705s5414lbl.pdf, 41 pages.

Prescribing Information for Treanda, 11 pages, (2008) retrieved on Feb. 9, 2022 https://www.accessdata.fda.gov/drugsatfda_docs/label/2008/022303lbl.pdf.

Prescribing Infromation for Bendeka Retrieved on Feb. 9, 2022, www.accessdata.fda.gov/drugsatfda_docs/label/2015/208194s000lbl.pdf. 23 pages.

Prescribing Infromation for Revlimid, Retrieved on Feb. 9, 2022, www.accessdata.fda.gov/drugsatfda_docs/label/2013/021880s034lbl.pdf, 33 pages.

Prevodnik, V. et al., "The predictive significance of CD20 expression in; B-cell lymphomas," Diagn Pathol., vol. 6(33): 6 pages (2011).

Shipp, M. et al., "A predictive model for aggressive non-Hodgkin's lymphoma," N Engl J Med., vol. 329(14):987-994 (1993).

Shen, Q.D. et al. "Gemcitabine-oxaliplatin plus rituximab (R-GemOx) as first-line treatment in elderly patients with diffuse large B-cell lymphoma: a single-arm, open-label, phase 2 trial," Lancet Haematology, vol. 5(6): 261-269 (2018).

Relander, T. et al., "Prognostic factors in follicular lymphoma," J Clin Oncol, vol. 28(17): 2902-2913 (2010).

Rigacci, L. et al., "Oxaliplatin-based chemotherapy (dexamethasone, high-dose cytarabine, and oxaliplatin) ± rituximab is an effective salvage regimen in patients with relapsed or refractory lymphoma," Cancer, vol. 116(19): 4573-4579 (2010).

Rossi, D et al., "Integrated mutational and cytogenetic analysis identifies new prognostic subgroups in chronic lymphocytic leukemia," Blood, vol. 121(8):1403-1412 (2013).

Rudikoff, S. et al., "Single amino acid substitution altering antigen-binding specificity," PNAS, vol. 79(6):1979-83 (1982).

Rummel, M. et al.,"Bendamustine plus rituximab versus CHOP plus rituximab as first-line treatment for patients with indolent and mantle-cell lymphomas: an open-label, multicentre, randomised, phase 3 non-inferiority trial," Lancet, vol. 381 (9873):1203-1210 (2013).

Safety and Efficacy Trial of Epcoritamab Combinations in Subjects With B-cell Non-Hodgkin Lymphoma, https://clinicaltrials.gov/ct2/show/NCT04663347 ClinicalTrials.gov Identifier: NCT04663347, Nov. 3, 2021, 13 pages.

Salles, G. et al., "Efficacy and safety of idelalisib in patients with relapsed, rituximab- and alkylating agent-refractory follicular lymphoma: a subgroup analysis of a phase 2 study," Haematologica, vol. 102(4):e159 (2017).

Schuster, S et al., "Tisagenlecleucel in Adult Relapsed or Refractory Diffuse Large B-Cell Lymphoma," N Engl J Med, vol. 380(1): 45-56 (2019).

Sehn, L. et al., "The revised International Prognostic Index (R-IPI) is a better predictor of outcome than the standard IPI for patients with diffuse large B-cell lymphoma treated with R-CHOP," Blood, vol. 109(5):1857-1861 (2007).

Seymour, JF et al., "Venetoclax-Rituximab in Relapsed or Refractory Chronic Lymphocytic Leukemia," N Engl J Med, vol. 378(12): 1107-1120(2018).

Shields, R et al., "High resolution mapping of the binding site on human IgG1 for Fc gamma RI, Fc gamma RII, Fc gamma RIII, and FcRn and design of IgG1 variants with improved binding to the Fc gamma R," Journ of Biol Chem., vol. 276(9): 6591-604 (2001).

Siegel, R et al., "Cancer statistics, 2019," 2019, CA Cancer J Clin, vol. 69(1):7-34 (2019).

Smith, E. et al."A novel, native-format bispecific antibody triggering T-cell killing of B-cells is robustly active in mouse tumor models and cynomolgus monkeys," Nat. Sci. Rep., vol. 5:17943: 12 pages (2015).

Staerz, U. et al., "Hybrid antibodies can target sites for attack by T cells," 1985, Nature, vol. 314(6012):628-31(1985).

Stanglmaier, M et al., "Bi20 (fBTA05), a novel trifunctional bispecific antibody (anti-CD20 x anti-CD3), mediates efficient killing of B-cell lymphoma cells even with very low CD20 expression levels," Int. J. Cancer, vol. 123 (5):1181-1189 (2008).

Sun, L et al., "Anti-CD20/CD3 T cell-dependent bispecific antibody; for the treatment of B cell malignancies," Science Transl Medicine, vol. 7(287): 1-11 (2015).

Tedder, TF et al., "The B cell surface molecule B1 is functionally linked with B cell activation and differentiation," J. Immunol., vol. 135(2): 973-979 (1985).

Tixier, F et al.,"Comparative toxicities of 3 platinum-containing chemotherapy regimens in relapsed/refractory lymphoma patients," Hematol Oncol., vol. 35(4):584-590 (2016).

Uhm, J., "Recent advances in chronic lymphocytic leukemia therapy," Blood Res Seoul, vol. 55(S1):S72-S82(2020).

Vajdos, F. et al., "Comprehensive functional maps of the antigen-binding site of an anti-ErbB2 antibody obtained with shotgun scanning mutagenesis," J Mol Biol., vol. 320(2): 415-28 (2002).

Valentine, M et al., "Phosphorylation of the CD20 phosphoprotein in resting B lymphocytes. Regulation by protein kinase C," J. Biol. Chem., vol. 264(19): 11282-11287 (1989).

Almasri, N et al., "Reduced expression of CD20 antigen as a characteristic marker for chronic lymphocytic leukemia," Am J Hematol, vol. 40(4):259-63 (1992).

Amgen, Blinatumomab prescribing information and medication guide, Dec. 2014, 24 pages.

Andersson, K. et al., "Expression of human B cell-associated antigens on leukemias and lymphomas: a model of human B cell differentiation," Blood, vol. 63(69):1424-1433 (1984).

Barrington, S. et al., "Role of imaging in the staging and response assessment of lymphoma: consensus of the International Conference on Malignant Lymphomas Imaging Working Group," J Clin Oncol., vol. 32(27):3048-58 (2014).

Bedouelle, H. et al., "Diversity and junction residues as hotspots of binding energy in an antibody neutralizing the dengue virus," FEBS J., vol. 273(1):34-46 (2006).

Berek, J. et al., "Catumaxomab for the treatment of malignant ascites in patients with chemotherapy-refractory ovarian cancer: a phase II study," Int. J Gynecol Cancer, vol. 24(9): 1583-1589 (2014).

Brown, M. et al., "Tolerance of single, but not multiple, amino acid replacements in antibody VH CDR 2: a means of minimizing B cell wastage from somatic hypermutation?," J Immunol., vol. 156(9):3285-91 (1996).

(56) References Cited

OTHER PUBLICATIONS

Canfield, S.M. et al., "The binding affinity of human IgG for its high affinity Fc receptor is determined by multiple amino acids in the CH2 domain and is modulated by the hinge region," J. Exp.Med., vol. 173(6):1483-91 (1991).
Casulo, C. et al., "Autologous Transplantation in Follicular Lymphoma with Early Therapy Failure: A National LymphoCare Study and Center for International Blood and Marrow Transplant Research Analysis," Biol Bood Marrow Transplant, vol. 24(6):1163-71 (2018).
Cheson, B. et al., "Recommendations for initial evaluation, staging, and response assessment of Hodgkin and non-Hodgkin lymphoma: the Lugano classification," J Clin Oncol., vol. 32(27):3059-68 (2014).
Cheson, B. et al., "Refinement of the Lugano Classification lymphoma response criteria in the era of immunomodulatory therapy," Blood, vol. 128(21):2489-96 (2016).
Chiorazzi, N. et al., "Chronic lymphocytic leukemia," N Engl J Med., vol. 352(8):804-15. (2005).
Chu, S. et al., "3111 Immunotherapy with Long-Lived Anti-CD20 x Anti-CD3 Bispecific Antibodies Stimulates Potent T Cell-Mediated Killing of Human B Cell Lines and of Circulating and Lymphoid B Cells in Monkeys: A Potential Therapy for B Cell Lymphomas and Leukemias,"56th ASH Annutal Meeting and Exposition, 2 pages (2014).
CLL-IPI, "An international prognostic index for patients with chronic lymphocytic leukaemia (CLL-IPI): a meta-analysis of individual patient data," Lancet Oncol., vol. 17(6):779-790(2016).
Coiffier, B. et al., "Guidelines for the management of pediatric and adult tumor lysis syndrome: an evidence-based review," J Clin Oncol., vol. 26(16):2767-2708 (2008).
Colman, P., "Effects of amino acid sequence changes on antibody-antigen interactions," Res Immunol., vol. 145 (1):33-6 (1994).
Cytarabine—cytarabine injection, solution Hospira, Inc., lebeling, retrieved on Feb. 9, 2022, labeling.pfizer.com/ShowLabeling.aspx?id=4397.
Dall'Acqua WF et al., "Modulation of the effector functions of a human IgG1 through engineering of its hinge region," J mmunol., vol. 177(2):1129-1138 (2006).
D'Arena, G et al., "Quantitative flow cytometry for the differential diagnosis of leukemic B-cell chronic lymphoproliferative disorders," Am J Hematol, vol. 64(4): 275-281 (2000).
Dexamethasone Sodium Phosphate Label, Retrieved on Feb. 9, 2022, www.accessdata.fda.gov/drugsatfda_docs/label/2014/40572s002lbledt pdf, 2 pages.
Doxorubicin Hydrochloride for Injection, usp, retrieved on Feb. 9, 2022 www.accessdata.fda.gov/drugsatfda_docs/label/2010/050467s070lbl.pdf, 22 pages.
Duncan, A.R., "The binding site for C1q on IgG," Nature, vol. 332(6166):738-40 (1988).
Einfeld, DA, et al., "Molecular cloning of the human B cell CD20 receptor predicts a hydrophobic protein with multiple transmembrane domains," EMBO Journ, vol. 7(3): 711-717 (1988).
Engelberts, P. J et al., "DuoBody-CD3xCD20 induces potent T-cell-mediated killing of malignant B cells in preclinical models and provides opportunities for subcutaneous dosing," EBioMedicine, vol. 52(102625) 13 pages (2020).
Fisher, K. et al., "Venetoclax and Obinutuzumab in Patients with CLL and Coexisting Conditions," N Engl J Med., vol. 380 (23):2225-2236 (2019).
Fitzmaurice, C et al., "Global, Regional, and National Cancer Incidence, Mortality, Years of Life Lost, Years Lived With Disability, and Disability-Adjusted Life-Years for 29 Cancer Groups, 1990 to 2016: A Systematic Analysis for the Global Burden of Disease Study," JAMA Oncol., vol. 4(11):1553-68 (2018).
Gall, J. M et al., "T cells armed with anti-CD3 x anti-CD20 bispecific antibody enhance killing of CD20+ malignant B cells and bypass complement-mediated rituximab resistance in vitro," Exp Hematol., vol. 33(4):452-9 (2005).
Garber, K., "Bispecific antibodies rise again," Nat. Rev. Drug Discov., vol. 13(11): 799-801 (2014).

GEN3013 Trial in Patients With Relapsed, Progressive or Refractory B-Cell Lymphoma, https://clinicaltrials.gov/ct2/show/study/NCT03625037, GEN3013 Trial in Patients With Relapsed . . . —Full Text View—ClinicalTrials.pdf, 8 pages.
Ginaldi, L. et al., "Levels of expression of CD19 and CD20 in chronic B cell leukaemias," J Clin Pathol., vol. 51(5): 364-369 (1988).
Gisselbrecht, C et al., "Salvage regimens with autologous transplantation for relapsed large B-cell lymphoma in the rituximab era," J Clin Oncol., vol. 28 (27): 4184-90 (2010).
Goede, V et al., "Obinutuzumab plus chlorambucil in patients with CLL and coexisting conditions," N Engl J Med., vol. 370(12):1101-10 (2014).
Gokarn Y. R. et al., "Self-buffering antibody formulations," Journal of Pharmaceutical Sciences, American Chemical Society and American Pharmaceutical Association US, vol. 97(8): 3051-66 (2008).
Hallek, M. et al., "Chronic lymphocytic leukaemia," The Lancet, vol. 391(10129):1524-1537 (2018).
Hallek, M. et al.,"Addition of rituximab to fludarabine and cyclophosphamide in patients with chronic lymphocytic leukaemia: a randomised, open-label, phase 3 trial," 2010, Lancet, vol. 376(9747): 1164-1174 (2010).
Herold, K et al., "A single course of anti-CD3 monoclonal antibody hOKT3gamma1 (Ala-Ala) results in improvement in C-peptide responses and clinical parameters for at least 2 years after onset of type 1 diabetes," Diabetes, vol. 54(6): 1763-1769 (2005).
Hezareh, M et al., "Effector function activities of a panel of mutants of a broadly neutralizing antibody against human immunodeficiency virus type 1," J Virol., vol. 75(24): 12161-12168 (2001).
Hiddemann, W. et al., "Frontline therapy with rituximab added to the combination of cyclophosphamide, doxorubicin, vincristine, and prednisone (CHOP) significantly improves the outcome for patients with advanced-stage follicular lymphoma compared with therapy with CHOP alone: results of a prospective randomized study of the German Low-Grade Lymphoma Study Group," Blood, vol. 106(12):3725-3732 (2005).
Howard, S. et al., "The tumor lysis syndrome," N Engl J Med, vol. 364(19): 1844-1854 (2011).
Ito K et al.,"Influence of R-CHOP Therapy on Immune System Restoration in Patients with B-Cell Lymphoma," Oncology, vol. 91(6):302-310 (2016).
Jabbour, E. et al., "Phase II Study Of The Hyper-CVAD Regimen In Combination With Ofatumumab As Frontline Therapy For Adults With CD-20 Positive Acute Lymphoblastic Leukemia (ALL)," Blood, vol. 122(21):2664: 5 pages (2003).
Jardin F., "Improving R-CHOP in diffuse large B-cell lymphoma is still a challenge" Lancet Oncology, vol. 20 (5): 605-606 (2019).
Jurinovic, V et al., "Autologous Stem Cell Transplantation for Patients with Early Progression of Follicular Lymphoma: A Follow-Up Study of 2 Randomized Trials from the German Low Grade Lymphoma Study Group," Biol Blood Marrow Transplant, vol. 24(6): 1172-9 (2018).
Kang J, et al., "Rapid formulation Development for Monoclonal Antibodies" Bioprocess International, 6 page, Apr. 12, 2016.
Khan, Y et al., "Acalabrutinib and its use in treatment of chronic lymphocytic leukemia," Future Oncol., vol. 15(6) 579-589 (2019).
Kontermann, R et al., "Bispecific antibodies," Drug Discov Today, vol. 20(7):838-847 (2015).
Kontemamm R "Dual targeting strategies with bispecific antibodies" mAbs vol. 4(2):182-197 (2012).
Kurokawa, T. et al., "Immune reconstitution of B-cell lymphoma patients receiving CHOP-based chemotherapy containing rituximab," Hematol Oncol., vol. 29(1): 5-9 (2011).
Sarkozy, C. et al., "New drugs for the management of relapsed or refractory diffuse large B-cell lymphoma," Ann Lymphoma, vol. 3(10) 19 pages (2019).
Adriamycin (DOXOrubicin HCl) for Injection, retrieved on Feb. 9, 2022 www.accessdata.fda.gov/drugsatfda_docs/label/2012/062921s022lbl.pdf, 21 pages.
Bacac, M. et al., "CD20-TCB with obinutuzumab pretreatment as next generation treatment of hematological malignancies," Clin Cancer Res., vol. 24(19):4785-4797 (2018).

(56) References Cited

OTHER PUBLICATIONS

Chiu, H. et al., "Combination lenalidomide-rituximab immunotherapy activates anti-tumour immunity and induces tumour cell death by complementary mechanisms of action in follicular lymphoma," British Journal of Haematology, vol. 185:240-253 (2019).

Genmab, "GEN3013 Trial in Patients With Relapsed, Progressive or Refractory B-Cell Lymphoma," NCT03625037, ClinicalTrials.gov, 8 pages (2018).

Lignon, J. et al., "Rituximab, Dexamethasone, Cytarabine, and Oxaliplatin (R-DHAX) Is an Effective and Safe Salvage Regimen in Relapsed/Refractory B-Cell Non-Hodgkin Lymphoma," Clinical Lymphoma, Myeloma & Leukemia, vol. 10 (4): 262-269 (2010).

Lum and Thakur, "Targeting T cells with bispecific antibodies for cancer therapy," BioDrugs, vol. 25(6): 365-379 (2011).

MedlinePlus. Lenalidomide, Mar. 2, 2022 pp. 1-7 (2022).

Mounier, N. et al., "Rituximab plus CHOP (R-CHOP) overcomes bcl-2-associated resistance to chemotherapy in elderly patients with diffuse large B-cell lymphoma (DLBCL)," Blood, vol. 101:4279-4284 (2003).

Mounier, N. et al., "Rituximab plus gemcitabine and oxaliplatin in patients with refractory/relapsed diffuse large B-cell lymphoma who are not candidates for high-dose therapy. A phase II Lymphoma Study Association trial," Haematologica, vol. 98(11): 1726-1731 (2013).

Sarkozy and Sehn, "Management of relapsed/refractory DLBCL," Best Practice & Research in Clinical Hematology, vol. 31: 209-216 (2018).

Tessoulin, B. et al., "Carboplatin instead of cisplatin in combination with dexamethasone, high-dose cytarabine with or without rituximab (DHAC+/−R) is an effective treatment with low toxicity in Hodgkin's and non-Hodgkin's lymphomas," Annals of Hematology, vol. 96: 943-950 (2017).

Genbank locus IGKC Human, P01834.2, Aug. 12, 2020, pp. 1-6 (2020).

NCT04358458, pp. 1-7, Apr. 20, 2020. (2020).

U.S. Department of Health and Human Services, FDA, Center for Drug Evaluation and Research (CDER), Jul. 2005, pp. i-iii and 1-27. (2005).

* cited by examiner

SEQUENCE LISTING

```
<160> NUMBER OF SEQ ID NOS: 29

<210> SEQ ID NO 1
<211> LENGTH: 8
<212> TYPE: PRT
<213> ORGANISM: Artificial sequence
<220> FEATURE:
<223> OTHER INFORMATION: CDR sequence

<400> SEQUENCE: 1

Gly Phe Thr Phe Asn Thr Tyr Ala
1               5

<210> SEQ ID NO 2
<211> LENGTH: 10
<212> TYPE: PRT
<213> ORGANISM: Artificial sequence
<220> FEATURE:
<223> OTHER INFORMATION: CDR sequence

<400> SEQUENCE: 2

Ile Arg Ser Lys Tyr Asn Asn Tyr Ala Thr
1               5                   10

<210> SEQ ID NO 3
<211> LENGTH: 16
<212> TYPE: PRT
<213> ORGANISM: Artificial sequence
<220> FEATURE:
<223> OTHER INFORMATION: CDR sequence

<400> SEQUENCE: 3

Val Arg His Gly Asn Phe Gly Asn Ser Tyr Val Ser Trp Phe Ala Tyr
1               5                   10                  15

<210> SEQ ID NO 4
<211> LENGTH: 9
<212> TYPE: PRT
<213> ORGANISM: Artificial sequence
<220> FEATURE:
<223> OTHER INFORMATION: CDR sequence

<400> SEQUENCE: 4

Thr Gly Ala Val Thr Thr Ser Asn Tyr
1               5
```

```
<210> SEQ ID NO 5
<211> LENGTH: 9
<212> TYPE: PRT
<213> ORGANISM: Artificial sequence
<220> FEATURE:
<223> OTHER INFORMATION: CDR sequence

<400> SEQUENCE: 5

Ala Leu Trp Tyr Ser Asn Leu Trp Val
1               5

<210> SEQ ID NO 6
<211> LENGTH: 125
<212> TYPE: PRT
<213> ORGANISM: Artificial sequence
<220> FEATURE:
<223> OTHER INFORMATION: Heavy chain variable region sequence 1

<400> SEQUENCE: 6

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 7
<211> LENGTH: 109
<212> TYPE: PRT
<213> ORGANISM: Artificial sequence
<220> FEATURE:
<223> OTHER INFORMATION: Light chain variable region sequence

<400> SEQUENCE: 7

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 8
```

<211> LENGTH: 8
<212> TYPE: PRT
<213> ORGANISM: Artificial sequence
<220> FEATURE:
<223> OTHER INFORMATION: CDR sequence

<400> SEQUENCE: 8

Gly Phe Thr Phe His Asp Tyr Ala
1               5

<210> SEQ ID NO 9
<211> LENGTH: 8
<212> TYPE: PRT
<213> ORGANISM: Artificial sequence
<220> FEATURE:
<223> OTHER INFORMATION: CDR sequence

<400> SEQUENCE: 9

Ile Ser Trp Asn Ser Gly Thr Ile
1               5

<210> SEQ ID NO 10
<211> LENGTH: 15
<212> TYPE: PRT
<213> ORGANISM: Artificial sequence
<220> FEATURE:
<223> OTHER INFORMATION: CDR sequence

<400> SEQUENCE: 10

Ala Lys Asp Ile Gln Tyr Gly Asn Tyr Tyr Tyr Gly Met Asp Val
1               5                   10                  15

<210> SEQ ID NO 11
<211> LENGTH: 6
<212> TYPE: PRT
<213> ORGANISM: Artificial sequence
<220> FEATURE:
<223> OTHER INFORMATION: CDR sequence

<400> SEQUENCE: 11

Gln Ser Val Ser Ser Tyr
1               5

<210> SEQ ID NO 12
<211> LENGTH: 9
<212> TYPE: PRT
<213> ORGANISM: Artificial sequence
<220> FEATURE:
<223> OTHER INFORMATION: CDR sequence

<400> SEQUENCE: 12

Gln Gln Arg Ser Asn Trp Pro Ile Thr
1               5

<210> SEQ ID NO 13
<211> LENGTH: 122
<212> TYPE: PRT
<213> ORGANISM: Artificial sequence
<220> FEATURE:
<223> OTHER INFORMATION: Heavy chain variable region sequence

<400> SEQUENCE: 13

Glu Val Gln Leu Val Glu Ser Gly Gly Gly Leu Val Gln Pro Asp Arg
1               5                   10                  15

Ser Leu Arg Leu Ser Cys Ala Ala Ser Gly Phe Thr Phe His Asp Tyr
            20                  25                  30

```
Ala Met His Trp Val Arg Gln Ala Pro Gly Lys Gly Leu Glu Trp Val
         35                  40                  45

Ser Thr Ile Ser Trp Asn Ser Gly Thr Ile Gly Tyr Ala Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                 85                  90                  95

Ala Lys Asp Ile Gln Tyr Gly Asn Tyr Tyr Gly Met Asp Val Trp
            100                 105                 110

Gly Gln Gly Thr Thr Val Thr Val Ser Ser
            115                 120
```

<210> SEQ ID NO 14
<211> LENGTH: 107
<212> TYPE: PRT
<213> ORGANISM: Artificial sequence
<220> FEATURE:
<223> OTHER INFORMATION: Light chain variable region sequence

<400> SEQUENCE: 14

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105
```

<210> SEQ ID NO 15
<211> LENGTH: 329
<212> TYPE: PRT
<213> ORGANISM: Homo Sapiens

<400> SEQUENCE: 15

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
            115                 120                 125
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 16
<211> LENGTH: 329
<212> TYPE: PRT
<213> ORGANISM: Artificial sequence
<220> FEATURE:
<223> OTHER INFORMATION: Heavy chain constant region

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
```

```
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly
                325

<210> SEQ ID NO 17
<211> LENGTH: 329
<212> TYPE: PRT
<213> ORGANISM: Artificial sequence
<220> FEATURE:
<223> OTHER INFORMATION: Heavy chain constant region

<400> SEQUENCE: 17

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
```

```
                180                 185                 190
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 18
<211> LENGTH: 329
<212> TYPE: PRT
<213> ORGANISM: Artificial sequence
<220> FEATURE:
<223> OTHER INFORMATION: Heavy chain constant region

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
```

```
                210                 215                 220
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 19
<211> LENGTH: 329
<212> TYPE: PRT
<213> ORGANISM: Artificial sequence
<220> FEATURE:
<223> OTHER INFORMATION: Heavy chain constant region

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
```

```
                    245                 250                 255
Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Leu
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 20
<211> LENGTH: 329
<212> TYPE: PRT
<213> ORGANISM: Artificial sequence
<220> FEATURE:
<223> OTHER INFORMATION: Heavy chain constant region

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                275                 280                 285
Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 21
<211> LENGTH: 106
<212> TYPE: PRT
<213> ORGANISM: Homo sapiens

<400> SEQUENCE: 21

```
Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105
```

<210> SEQ ID NO 22
<211> LENGTH: 106
<212> TYPE: PRT
<213> ORGANISM: Homo sapiens

<400> SEQUENCE: 22

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 23
<211> LENGTH: 107
<212> TYPE: PRT
<213> ORGANISM: Homo sapiens

<400> SEQUENCE: 23

```
Arg Thr Val Ala Ala Pro Ser Val Phe Ile Phe Pro Pro Ser Asp Glu
1               5                   10                  15
```

```
Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 24
<211> LENGTH: 454
<212> TYPE: PRT
<213> ORGANISM: Artificial sequence
<220> FEATURE:
<223> OTHER INFORMATION: Antibody heavy chain

<400> SEQUENCE: 24

Glu Val Lys Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
             20                  25                  30

Ala Met Asn Trp Val Arg Gln Ala Pro Gly Lys Gly Leu Glu Trp Val
         35                  40                  45

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Ser Ser
 65                  70                  75                  80

Leu Tyr Leu Gln Met Asn Asn Leu Lys Thr Glu Asp Thr Ala Met Tyr
                 85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Phe Glu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270
```

```
Ala Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Leu Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly
450

<210> SEQ ID NO 25
<211> LENGTH: 215
<212> TYPE: PRT
<213> ORGANISM: Artificial sequence
<220> FEATURE:
<223> OTHER INFORMATION: Antibody light chain

<400> SEQUENCE: 25

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175
```

```
Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
            195                 200                 205

Val Ala Pro Thr Glu Cys Ser
            210             215

<210> SEQ ID NO 26
<211> LENGTH: 451
<212> TYPE: PRT
<213> ORGANISM: Artificial sequence
<220> FEATURE:
<223> OTHER INFORMATION: Antibody heavy chain

<400> SEQUENCE: 26

Glu Val Gln Leu Val Glu Ser Gly Gly Gly Leu Val Gln Pro Asp Arg
1               5                   10                  15

Ser Leu Arg Leu Ser Cys Ala Ala Ser Gly Phe Thr Phe His Asp Tyr
            20                  25                  30

Ala Met His Trp Val Arg Gln Ala Pro Gly Lys Gly Leu Glu Trp Val
            35                  40                  45

Ser Thr Ile Ser Trp Asn Ser Gly Thr Ile Gly Tyr Ala Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
            210                 215                 220

Cys Asp Lys Thr His Thr Cys Pro Pro Cys Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ala Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320
```

```
Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
                435                 440                 445

Ser Pro Gly
    450

<210> SEQ ID NO 27
<211> LENGTH: 214
<212> TYPE: PRT
<213> ORGANISM: Artificial sequence
<220> FEATURE:
<223> OTHER INFORMATION: Antibody light chain

<400> SEQUENCE: 27

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 28
<211> LENGTH: 207
<212> TYPE: PRT
<213> ORGANISM: Homo Sapiens

<400> SEQUENCE: 28

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 29
<211> LENGTH: 297
<212> TYPE: PRT
<213> ORGANISM: Homo Sapiens

<400> SEQUENCE: 29

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

-continued

```
Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295
```

BISPECIFIC ANTIBODY AGAINST CD3 AND CD20 IN COMBINATION THERAPY FOR TREATING FOLLICULAR LYMPHOMA

CROSS-REFERENCE TO RELATED APPLICATIONS

This application is a continuation of U.S. application Ser. No. 17/742,143, filed on Sep. 10, 2021, which claims the benefit of U.S. Provisional Application Ser. No. 63/076,792, filed on Sep. 10, 2020. The entire contents of the above-referenced patent applications are incorporated herein by reference.

SEQUENCE LISTING

The instant application contains a Sequence Listing which has been submitted electronically in ASCII format and is hereby incorporated by reference in its entirety. Said ASCII copy, created on Dec. 21, 2021, is named GMI_198CN_Sequence_Listing.txt and is 43449 bytes in size.

FIELD

The present invention relates to bispecific antibodies targeting both CD3 and CD20 and the use of such antibodies in combination with a standard of care regimen of rituximab and bendamustine for the treatment of follicular lymphoma, for example, previously untreated follicular lymphoma. Advantageous treatment regimens are also provided.

BACKGROUND

Follicular lymphoma is an incurable disease characterized by an indolent clinical course with a frequent need for several lines of treatment. Approximately 2 to 3% of patients per year will have histologic transformation to an aggressive lymphoma, frequently DLBCL (approximately 20% transformation at 5 years and approximately 30% transformation at 10 years). The prognosis after histologic transformation is extremely poor (median OS of 1 to 2 years) (Relander et al., *J Clin Oncol* 2010; 28:2902-13; Wagner-Johnston et al., *Blood* 2015; 126:851-7).

The most common first-line therapies for advanced follicular lymphoma are R-CHOP or rituximab and bendamustine (BR) (Hiddemann et al., *Blood* 2005; 106:3725-32; Rummel et al., *Lancet* 2013; 381:1203-10). Treatment of relapsed or refractory (R/R) follicular lymphoma is influenced by previous therapy regimens, duration of remission, and PS. Irrespective of first-line treatment choice (including R-CHOP/obinutuzumab-CHOP, BR), progression of disease at 24 months occurs in 20% of patients and is a robust predictor of poor OS, with only 35% to 50% of patients alive at 5 years. A non-cross-resistant salvage regimen is usually applied in progression of disease at 24 months, and HDT-ASCT is considered for eligible patients (Casulo et al., *Biol Blood Marrow Transplant* 2018; 24:1163-71; Jurinovic et al., *Biol Blood Marrow Transplant* 2018; 24:1172-9).

Several treatment options are approved for a second or later relapse of follicular lymphoma. The combination of rituximab +lenalidomide ($R^2$) has demonstrated impressive response rates, but with a 2-year PFS of only 50 to 60% (Leonard et al., *J Clin Oncol* 2019; 37:1188-99). Treatment options for patients who have failed several lines of therapy, including monoclonal anti-CD20 antibodies and alkylating agents, are limited. Although idelalisib is approved for double-refractory cases, it demonstrated a 1-year PFS of only 43% and several toxicities leading to treatment discontinuation (Salles et al., *Haematologica* 2017;e156).

Given the limited efficacy of and response of subjects to currently available treatments for follicular lymphoma, new treatments for this patient population are highly desired.

SUMMARY

Provided herein are methods of treating human subjects who have follicular lymphoma, for example, previously untreated follicular lymphoma, by administering a bispecific antibody which binds to CD3 and CD20 in combination with a standard of care regimen of rituximab and bendamustine, in particular, advantageous clinical treatment regimens.

In one aspect, provided herein is a method of treating follicular lymphoma in a human subject, the method comprising administering to the subject the combination of epcoritamab with rituximab and bendamustine, e.g., the method comprising administering to the subject an effective amount of rituximab, bendamustine, and epcoritamab.

In one aspect, provided herein is a method of treating follicular lymphoma, for example, previously untreated follicular lymphoma in a human subject, the method comprising administering to the subject a bispecific antibody and an effective amount of rituximab and bendamustine, wherein the bispecific antibody comprises:

(i) a first binding arm comprising a first antigen-binding region which binds to human CD3c (epsilon) and comprises a variable heavy chain (VH) region and a variable light chain (VL) region, wherein the VH region comprises the CDR1, CDR2 and CDR3 sequences that are in the VH region sequence of SEQ ID NO: 6, and the VL region comprises the CDR1, CDR2 and CDR3 sequences that are in the VL region sequence of SEQ ID NO: 7; and (ii) a second binding arm comprising a second antigen-binding region which binds to human CD20 and comprises a VH region and a VL region, wherein the VH region comprises the CDR1, CDR2 and CDR3 sequences that are in the VH region sequence of SEQ ID NO: 13, and the VL region comprises the CDR1, CDR2 and CDR3 sequences that are in the VL region sequence of SEQ ID NO: 14, wherein the bispecific antibody is administered at a dose of 24 mg or 48 mg, and wherein rituximab, bendamustine, and the bispecific antibody are administered in 28-day cycles.

In some embodiments, the bispecific antibody is administered at a dose of (or a dose of about) 24 mg. In some embodiments, the bispecific antibody is administered at a dose of (or a dose of about) 48 mg.

In one embodiment, the bispecific antibody is administered once every week at a dose of 24 mg or 48 mg (weekly administration), e.g., for 2.5 28-day cycles. In some embodiments, the bispecific antibody is administered once every two weeks after the weekly administration (biweekly administration), e.g., for six 28-day cycles. In yet some embodiments, the bispecific antibody is administered once every four weeks after the biweekly administration, e.g., for up to two years total duration of treatment with the bispecific antibody from initiation of rituximab and bendamustine (i.e., from cycle 1). In a further embodiment, a priming dose (e.g., 0.16 mg or about 0.16 mg) of the bispecific antibody is administered two weeks prior to administering the first weekly dose of 24 mg or 48 mg. In some embodiments, after administering the priming dose and prior to administering the weekly dose of 24 mg or 48 mg, an intermediate dose (e.g., 0.8 mg or about 0.8 mg) of the bispecific antibody is administered. In some embodiments, the priming dose is administered one week before the intermediate dose, and the intermediate dose is administered one week before the first weekly dose of 24 mg or 48 mg.

In some embodiments, rituximab is administered in a 28-day cycle once every four weeks, e.g., for six 28-day cycles. In some embodiments, rituximab is administered at a dose of 375 mg/m$^2$.

In some embodiments, bendamustine is administered once a day from day 1 to day 2 of the 28-day cycles, e.g., for six 28-day cycles. In some embodiments, bendamustine is administered at a dose of 90 mg/m$^2$.

In some embodiments, rituximab, bendamustine, and the bispecific antibody are administered on the same day (e.g., on day 1 of cycles 1-6), e.g., as shown in Table 2.

In some embodiments, administration is performed in 28-day cycles, wherein
  (a) the bispecific antibody is administered as follows:
    (i) in cycle 1, a priming dose of 0.16 mg is administered on day 1, an intermediate dose of 0.8 mg is administered on day 8, and a dose of 24 mg is administered on days 15 and 22;
    (ii) in cycles 2 and 3, a dose of 24 mg is administered on days 1, 8, 15, and 22;
    (iii) in cycles 4-9, a dose of 24 mg is administered on days 1 and 15; and
    (iv) in cycle 10 and subsequent cycles, a dose of 24 mg is administered on day 1;
  (b) rituximab is administered on day 1 in cycles 1-6; and
  (c) bendamustine is administered on days 1 and 2 in cycles 1-6.

In another embodiment, administration is performed in 28-day cycles, wherein
  (a) the bispecific antibody is administered as follows:
    (i) in cycle 1, a priming dose of 0.16 mg is administered on day 1, an intermediate dose of 0.8 mg is administered on day 8, and a dose of 48 mg is administered on days 15 and 22;
    (ii) in cycles 2 and 3, a dose of 48 mg is administered on days 1, 8, 15, and 22;
    (iii) in cycles 4-9, a dose of 48 mg is administered on days 1 and 15; and
    (iv) in cycle 10 and subsequent cycles, a dose of 48 mg is administered on day 1;
  (b) rituximab is administered on day 1 in cycles 1-6; and
  (c) bendamustine is administered on days 1 and 2 in cycles 1-6.

In some embodiments, rituximab, bendamustine, and the bispecific antibody epcoritamab are administered on the same day (e.g., on day 1 of cycles 1-6), e.g., as shown in Table 2.

In some embodiments, administration is performed in 28-day cycles, wherein
  (a) the bispecific antibody epcoritamab is administered as follows:
    (i) in cycle 1, a priming dose of 0.16 mg is administered on day 1, an intermediate dose of 0.8 mg is administered on day 8, and a dose of 24 mg is administered on days 15 and 22;
    (ii) in cycles 2 and 3, a dose of 24 mg is administered on days 1, 8, 15, and 22;
    (iii) in cycles 4-9, a dose of 24 mg is administered on days 1 and 15; and
    (iv) in cycle 10 and subsequent cycles, a dose of 24 mg is administered on day 1;
  (b) rituximab is administered on day 1 in cycles 1-6; and
  (c) bendamustine is administered on days 1 and 2 in cycles 1-6.

In some embodiments, administration is performed in 28-day cycles, wherein
  (a) the bispecific antibody epcoritamab is administered as follows:
    (i) in cycle 1, a priming dose of 0.16 mg is administered on day 1, an intermediate dose of 0.8 mg is administered on day 8, and a dose of 48 mg is administered on days 15 and 22;
    (ii) in cycles 2 and 3, a dose of 48 mg is administered on days 1, 8, 15, and 22;
    (iii) in cycles 4-9, a dose of 48 mg is administered on days 1 and 15; and
    (iv) in cycle 10 and subsequent cycles, a dose of 48 mg is administered on day 1;
  (b) rituximab is administered on day 1 in cycles 1-6; and
  (c) bendamustine is administered on days 1 and 2 in cycles 1-6.

In some embodiments, the bispecific antibody is administered subcutaneously. In some embodiments, rituximab is administered intravenously. In some embodiments, bendamustine is administered intravenously.

In some embodiments, the bispecific antibody, rituximab, and bendamustine are administered sequentially. For example, if administered on the same day, (a) rituximab is administered before the bispecific antibody (e.g., day 1 of cycles 1-6); (b) bendamustine is administered before the bispecific antibody (e.g., day 1 of cycles 1-6); (c) rituximab is administered before bendamustine (e.g., day 1 of cycles 1-6); or (d) rituximab is administered first, bendamustine is administered second, and the bispecific antibody is administered last (e.g., day 1 of cycles 1-6). In some embodiments, if administered on the same day, (a) rituximab is administered before the bispecific antibody (e.g., day 1 of cycles 1-6); (b) bendamustine is administered before the bispecific antibody (e.g., day 1 of cycles 1-6); (c) bendamustine is administered before rituximab (e.g., day 1 of cycles 1-6); or (d) bendamustine is administered first, rituximab is administered second, and the bispecific antibody is administered last (e.g., day 1 of cycles 1-6).

In some embodiments, the subject has grade 1, 2, or 3a previously untreated follicular lymphoma. In some embodiments, the subject has Stage II, III, or IV previously untreated follicular lymphoma.

In some embodiments, the subject is treated with prophylaxis for cytokine release syndrome (CRS). In some embodiments, the prophylaxis comprises administering a corticosteroid (e.g., prednisolone at a dose of, e.g., 100 mg or equivalent thereof, including oral dose) on, for example, the same day as the bispecific antibody. In some embodiments, the corticosteroid is further administered on the second, third, and fourth days after administering the bispecific antibody.

In some embodiments, the subject is administered pre-medication, such as antihistamine (e.g., diphenhydramine, intravenously or orally at a dose of, e.g., 50 mg or equivalent thereof) and/or antipyretic (e.g., acetaminophen at a dose of, e.g., 560-1000 mg), to reduce reactions to injections. In some embodiments, the premedication is administered on the same day as the bispecific antibody.

In some embodiments, the prophylaxis and premedication are administered during cycle 1. In some embodiments, the prophylaxis is administered during cycle 2 when the subject experiences CRS greater than grade 1 after the last administration of the bispecific antibody in cycle 1. In yet some embodiments, the prophylaxis is continued in a subsequent cycle, when in the last administration of the bispecific antibody of the previous cycle, the subject experiences CRS greater than grade 1. In a further embodiment, the premedication is administered during cycle 2. In yet a further embodiment, the premedication is administered during subsequent cycles.

In some embodiments, the subject is administered antibiotics if the subject develops Grade 1 CRS. In some embodiments, the subject is administered a vasopressor if the subject develops Grade 2 or Grade 3 CRS. In some embodiments, the subject is administered at least two vasopressors if the subject develops Grade 4 CRS.

In some embodiments, the subject is administered tocilizumab if the subject develops Grade 2, Grade 3, or Grade 4 CRS. In some embodiments, the subject is further administered a steroid (e.g., dexamethasone or methylprednisolone). In yet some embodiments, tocilizumab is switched to an anti-IL-6 antibody (e.g., siltuximab) or an IL-1R antagonist (e.g., anakinra) if the subject is refractory to tocilizumab.

In some embodiments, the subject is administered prophylaxis for tumor lysis syndrome (TLS). In some embodiments, the prophylaxis for TLS comprises administering one or more uric acid reducing agents prior to administration of the bispecific antibody. In yet some embodiments, rasburicase and/or allopurinol is administered as the uric acid reducing agent. In some embodiments, when a subject shows signs of TLS, supportive therapy, such as rasburicase, may be used.

In some embodiments, the subject treated with the methods described herein achieves a complete response, a partial response, or stable disease, e.g., as defined by the Lugano criteria or LYRIC.

In some embodiments, the first antigen-binding region of the bispecific antibody comprises VHCDR1, VHCDR2, and VHCDR3 comprising the amino acid sequences set forth in SEQ ID NOs: 1, 2, and 3, respectively, and VLCDR1, VLCDR2, and VLCDR3 comprising the amino acid sequences set forth in SEQ ID NO: 4, the sequence GTN, and SEQ ID NO: 5, respectively; and the second antigen-binding region comprises VHCDR1, VHCDR2, and VHCDR3 comprising the amino acid sequences set forth in SEQ ID NOs: 8, 9, and 10, respectively, and VLCDR1, VLCDR2, and VLCDR3 comprising the amino acid sequences set forth in SEQ ID NO: 11, the sequence DAS, and SEQ ID NO: 12, respectively.

In some embodiments, the first antigen-binding region of the bispecific antibody comprises a VH region comprising the amino acid sequence of SEQ ID NO: 6, and the VL region comprising the amino acid sequence of SEQ ID NO: 7; and the second antigen-binding region comprises a VH region comprising the amino acid sequence of SEQ ID NO: 13, and the VL region comprising the amino acid sequence of SEQ ID NO: 14.

In some embodiments, the first binding arm of the bispecific antibody is derived from a humanized antibody, preferably from a full-length IgG1,λ (lambda) antibody (e.g., SEQ ID NO: 22). In some embodiments, the second binding arm of the bispecific antibody is derived from a human antibody, preferably from a full-length IgG1,κ (kappa) antibody (e.g., SEQ ID NO: 23). In yet some embodiments, the bispecific antibody is a full-length antibody with a human IgG1 constant region.

In some embodiments, the bispecific antibody comprises an inert Fc region, for example, an Fc region in which the amino acids in the positions corresponding to positions L234, L235, and D265 in the human IgG1 heavy chain constant region of SEQ ID NO: 15 are F, E, and A, respectively. In some embodiments, the bispecific antibody comprises substitutions which promote bispecific antibody formation, for example, wherein in the first heavy chain, the amino acid in the position corresponding to F405 in the human IgG1 heavy chain constant region of SEQ ID NO: 15 is L, and wherein in the second heavy chain, the amino acid in the position corresponding to K409 in the human IgG1 heavy chain constant region of SEQ ID NO: 15 is R, or vice versa. In some embodiments, the bispecific antibody has both an inert Fc region (e.g., substitutions at L234, L235, and D265 (e.g., L234F, L235E, and D265A)) and substitutions which promote bispecific antibody formation (e.g., F405L and K409R). In a further embodiment, the bispecific antibody comprises heavy chain constant regions comprising the amino acid sequences of SEQ ID NOs: 19 and 20.

In some embodiments, the bispecific antibody comprises a first heavy chain and a first light chain comprising (or consisting of) the amino acid sequences set forth in SEQ ID NOs: 24 and 25, respectively, and a second heavy chain and a second light chain comprising (or consisting of) the amino acid sequences set forth in SEQ ID NOs: 26 and 27, respectively. In some embodiments, the bispecific antibody is epcoritamab, or a biosimilar thereof.

BRIEF DESCRIPTION OF THE DRAWINGS

FIG. 1B: CD25; FIG. 1C: LAMP-1) and percentage T-cell-mediated cytotoxicity (FIG. 1D). Results shown are from one representative donor out of three donors tested.

DETAILED DESCRIPTION

Definitions

Figure 1A:
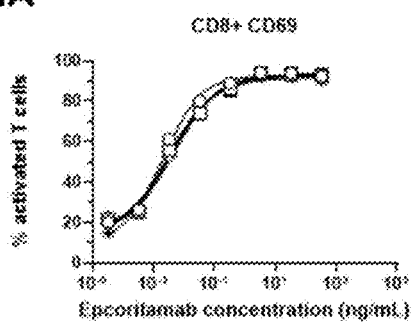
FIGS. 1A-1D are graphs showing the effects of bendamustine on epcoritamab-induced T-cell activation and T-cell-mediated cytotoxicity. T cells were incubated with Raji (left panels) or SU-DHL-4 (right panels) cells in the presence of epcoritamab with or without bendamustine. Data shown are percentages activated CD8+ T cells (FIG. 1A: CD69.
Figure 1A:
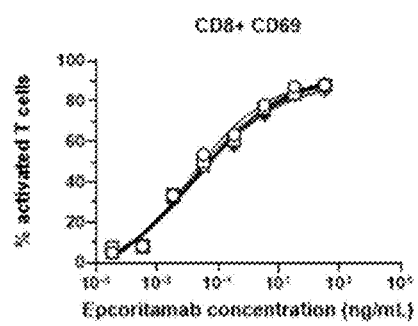

The term "immunoglobulin" as used herein refers to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized (see, e.g., Fundamental Immunology Ch. 7 (Paul, W., ed., 2nd ed. Raven Press, N.Y. (1989)). Briefly, each heavy chain typically is comprised of a heavy chain variable region (abbreviated herein as VH or $V_H$) and a heavy chain constant region (abbreviated herein as CH or $C_H$). The heavy chain constant region typically is comprised of three domains, CH1, CH2, and CH3. The hinge region is the region between the CH1 and CH2 domains of the heavy chain and is highly flexible. Disulfide bonds in the hinge region are part of the interactions between two heavy chains in an IgG molecule. Each light chain typically is comprised of a light chain variable region (abbreviated herein as VL or $V_L$) and a light chain constant region (abbreviated herein as CL or $C_L$). The light chain constant region typically is comprised of one domain, CL. The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk *J Mol Biol* 1987; 196:90117). Unless otherwise stated or contradicted by context, CDR sequences herein are identified according to IMGT rules (Brochet X., *Nucl Acids Res* 2008; 36:W503-508; Lefranc MP., *Nucl Acids Res* 1999; 27:209-12; www.imgt.org/). Unless otherwise stated or contradicted by context, reference to amino acid positions in the constant regions is according to the EU-numbering (Edelman et al., *PNAS.* 1969; 63:78-85; Kabat et al., Sequences of Proteins of Immunological Interest, Fifth Edition. 1991 NIH Publication No. 91-3242). For example, SEQ ID NO: 15 sets forth amino acids positions 118-447, according to EU numbering, of the IgG1 heavy chain constant region.

The term "amino acid corresponding to position . . . " as used herein refers to an amino acid position number in a human IgG1 heavy chain. Corresponding amino acid positions in other immunoglobulins may be found by alignment with human IgG1. Thus, an amino acid or segment in one sequence that "corresponds to" an amino acid or segment in another sequence is one that aligns with the other amino acid or segment using a standard sequence alignment program such as ALIGN, ClustalW or similar, typically at default settings and has at least 50%, at least 80%, at least 90%, or at least 95% identity to a human IgG1 heavy chain. It is within the ability of one of ordinary skill in the art to align a sequence or segment in a sequence and thereby determine the corresponding position in a sequence to an amino acid position according to the present invention.

The term "antibody" (Ab) as used herein in the context of the present invention refers to an immunoglobulin molecule which has the ability to specifically bind to an antigen under typical physiological conditions with a half-life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The term antibody, unless specified otherwise, also encompasses polyclonal antibodies, monoclonal antibodies (mAbs), antibody-like polypeptides, chimeric antibodies and humanized antibodies.

The term "antibody fragment" or "antigen-binding fragment" as used herein refers to a fragment of an immunoglobulin molecule which retains the ability to specifically bind to an antigen, and can be generated by any known technique, such as enzymatic cleavage, peptide synthesis, and recombinant techniques. Examples of antibody fragments include (i) a Fab' or Fab fragment, a monovalent fragment consisting of the VL, VH, CL and CH1 domains, or a monovalent antibody as described in WO2007059782 (Genmab); (ii) F(ab')$_2$ fragments, bivalent fragments comprising two Fab fragments linked by a disulfide bridge at the hinge region; (iii) a Fd fragment consisting essentially of the VH and CH1 domains; (iv) a Fv fragment consisting essentially of the VL and VH domains of a single arm of an antibody, (v) a dAb fragment (Ward et al., *Nature* 1989; 341: 54446), which consists essentially of a VH domain and also called domain antibodies (Holt et al; *Trends Biotechnol* 2003; 21:484-90); (vi) camelid or nanobodies (Revets et al; *Expert Opin Biol Ther* 2005; 5:111-24) and (vii) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see, e.g., Bird et al., *Science* 1988; 242:42326 and Huston et al., *PNAS* 1988; 85:587983). Such single chain antibodies are encompassed within the term antibody fragment unless otherwise noted or clearly indicated by context.

The term "antibody-binding region" or "antigen-binding region" as used herein refers to the region which interacts with the antigen and comprises both the VH and the VL regions. The term antibody when used herein refers not only to monospecific antibodies, but also multispecific antibodies which comprise multiple, such as two or more, e.g., three or more, different antigen-binding regions. The term antigen-binding region, unless otherwise stated or clearly contradicted by context, includes fragments of an antibody that are antigen-binding fragments, i.e., retain the ability to specifically bind to the antigen.

As used herein, the term "isotype" refers to the immunoglobulin class (for instance IgG1, IgG2, IgG3, IgG4, IgD, IgA, IgE, or IgM) that is encoded by heavy chain constant region genes. When a particular isotype, e.g., IgG1, is mentioned, the term is not limited to a specific isotype sequence, e.g., a particular IgG1 sequence, but is used to indicate that the antibody is closer in sequence to that isotype, e.g. IgG1, than to other isotypes. Thus, e.g., an IgG1 antibody may be a sequence variant of a naturally-occurring IgG1 antibody, which may include variations in the constant regions.

The term "bispecific antibody" or "bs" or "bsAb" as used herein refers to an antibody having two different antigen-binding regions defined by different antibody sequences. A bispecific antibody can be of any format.

The terms "half molecule", "Fab-arm", and "arm", as used herein, refer to one heavy chain-light chain pair.

When a bispecific antibody is described as comprising a half-molecule antibody "derived from" a first parental antibody, and a half-molecule antibody "derived from" a second parental antibody, the term "derived from" indicates that the bispecific antibody was generated by recombining, by any known method, said half-molecules from each of said first and second parental antibodies into the resulting bispecific antibody. In this context, "recombining" is not intended to be limited by any particular method of recombining and thus includes all of the methods for producing bispecific antibodies described herein, including for example recombining by half-molecule exchange (also known as "controlled Fab-arm exchange"), as well as recombining at nucleic acid level and/or through co-expression of two half-molecules in the same cells.

The term "full-length" as used herein in the context of an antibody indicates that the antibody is not a fragment but contains all of the domains of the particular isotype normally found for that isotype in nature, e.g., the VH, CH1, CH2, CH3, hinge, VL and CL domains for an IgG1 antibody. A full-length antibody may be engineered. An example of a "full-length" antibody is epcoritamab.

The term "Fc region" as used herein refers to an antibody region consisting of the Fc sequences of the two heavy chains of an immunoglobulin, wherein said Fc sequences comprise at least a hinge region, a CH2 domain, and a CH3 domain.

The term "heterodimeric interaction between the first and second CH3 regions" as used herein refers to the interaction between the first CH3 region and the second CH3 region in a first-CH3/second-CH3 heterodimeric protein.

The term "homodimeric interactions of the first and second CH3 regions" as used herein refers to the interaction between a first CH3 region and another first CH3 region in a first-CH3/first-CH3 homodimeric protein and the interaction between a second CH3 region and another second CH3 region in a second-CH3/second-CH3 homodimeric protein.

The term "binding" as used herein in the context of the binding of an antibody to a predetermined antigen typically refers to binding with an affinity corresponding to a $K_D$ of about $10^{-6}$ M or less, e.g., $10^{-7}$ M or less, such as about $10^{-8}$ M or less, such as about $10^{-9}$ M or less, about $10^{-10}$ M or less, or about $10^{-11}$ M or even less, when determined by, e.g., BioLayer Interferometry (BLI) technology in a Octet HTX instrument using the antibody as the ligand and the antigen as the analyte, and wherein the antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ of binding to a non-specific antigen (e.g., BSA, casein) other than the predetermined antigen or a closely related antigen. The amount with which the $K_D$ of binding is lower is dependent on the $K_D$ of the antibody, so that when the $K_D$ of the antibody is very low, then the amount with which the $K_D$ of binding to the antigen is lower than the $K_D$ of binding to a non-specific antigen may be at least 10,000-fold (i.e., the antibody is highly specific).

The term "isolated antibody" as used herein refers to an antibody which is substantially free of other antibodies having different antigenic specificities. In a preferred embodiment, an isolated bispecific antibody that specifically binds to CD20 and CD3 is in addition substantially free of monospecific antibodies that specifically bind to CD20 or CD3.

The term "CD3" as used herein refers to the human Cluster of Differentiation 3 protein which is part of the T-cell co-receptor protein complex and is composed of four distinct chains. CD3 is also found in other species, and thus, the term "CD3" is not limited to human CD3 unless contradicted by context. In mammals, the complex contains a CD3γ (gamma) chain (human CD3γ chain UniProtKB/Swiss-Prot No P09693, or cynomolgus monkey CD3γ UniProtKB/Swiss-Prot No Q95LI7), a CD3δ (delta) chain (human CD3δ UniProtKB/Swiss-Prot No P04234, or cynomolgus monkey CD3δ UniProtKB/Swiss-Prot No Q95LI8), two CD3ε (epsilon) chains (human CD3ε UniProtKB/Swiss-Prot No P07766, SEQ ID NO: 28); cynomolgus CD3ε UniProtKB/Swiss-Prot No Q95LI5; or rhesus CD3ε UniProtKB/Swiss-Prot No G7NCB9), and a CD3ζ-chain (zeta) chain (human CD3ζ UniProtKB/Swiss-Prot No P20963, cynomolgus monkey CD3ζ UniProtKB/Swiss-Prot No Q09TK0). These chains associate with a molecule known as the T-cell receptor (TCR) and generate an activation signal in T lymphocytes. The TCR and CD3 molecules together comprise the TCR complex.

The term "CD3 antibody" or "anti-CD3 antibody" as used herein refers to an antibody which binds specifically to the antigen CD3, in particular human CD3ε (epsilon).

The term "human CD20" or "CD20" refers to human CD20 (UniProtKB/Swiss-Prot No P11836, SEQ ID NO: 29) and includes any variants, isoforms, and species homologs of CD20 which are naturally expressed by cells, including tumor cells, or are expressed on cells transfected with the CD20 gene or cDNA. Species homologs include rhesus monkey CD20 (macaca mulatta; UniProtKB/Swiss-Prot No H9YXP1) and cynomolgus monkey CD20 (*Macaca fascicularis*; UniProtKB No G7PQ03).

The term "CD20 antibody" or "anti-CD20 antibody" as used herein refers to an antibody which binds specifically to the antigen CD20, in particular to human CD20.

The term "CD3xCD20 antibody", "anti-CD3xCD20 antibody", "CD20xCD3 antibody" or "anti-CD20xCD3 antibody" as used herein refers to a bispecific antibody which comprises two different antigen-binding regions, one of which binds specifically to the antigen CD20 and one of which binds specifically to CD3.

The term "DuoBody-CD3xCD20" as used herein refers to an IgG1 bispecific CD3xCD20 antibody comprising a first heavy and light chain pair as defined in SEQ ID NO: 24 and SEQ ID NO: 25, respectively, and comprising a second heavy and light chain pair as defined in SEQ ID NO: 26 and SEQ ID NO: 27. The first heavy and light chain pair comprises a region which binds to human CD3ε (epsilon), the second heavy and light chain pair comprises a region which binds to human CD20. The first binding region comprises the VH and VL sequences as defined by SEQ ID NOs: 6 and 7, and the second binding region comprises the VH and VL sequences as defined by SEQ ID NOs: 13 and 14. This bispecific antibody can be prepared as described in WO 2016/110576.

Antibodies comprising functional variants of the heavy chain, light chains, VL regions, VH regions, or one or more CDRs of the antibodies of the examples as also provided herein. A functional variant of a heavy chain, a light chain, VL, VH, or CDRs used in the context of an antibody still allows the antibody to retain at least a substantial proportion (at least about 90%, 95% or more) of functional features of the "reference" and/or "parent" antibody, including affinity and/or the specificity/selectivity for particular epitopes of CD20 and/or CD3, Fc inertness and PK parameters such as half-life, Tmax, Cmax. Such functional variants typically retain significant sequence identity to the parent antibody and/or have substantially similar length of heavy and light chains. The percent identity between two sequences is a function of the number of identical positions shared by the sequences (i.e., % homology=# of identical positions/total # of positionsx100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, *J Mol Biol* 1970; 48:444-453 algorithm. Exemplary variants include those which differ from heavy and/or light chains, VH and/or VL, and/or CDR regions of the parent antibody sequences mainly by conservative substitutions; e.g., 10, such as 9, 8, 7, 6, 5, 4, 3, 2 or 1 of the substitutions in the variant may be conservative amino acid residue replacements.

Conservative substitutions may be defined by substitutions within the classes of amino acids reflected in the following table:

TABLE 1

| Amino acid residue classes for conservative substitutions | |
| --- | --- |
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Unless otherwise indicated, the following nomenclature is used to describe a mutation: i) substitution of an amino acid in a given position is written as, e.g., K409R which means a substitution of a Lysine in position 409 with an Arginine; and ii) for specific variants the specific three or one letter codes are used, including the codes Xaa and X to indicate any amino acid residue. Thus, the substitution of Lysine with Arginine in position 409 is designated as: K409R, and the substitution of Lysine with any amino acid residue in position 409 is designated as K409X. In case of deletion of Lysine in position 409 it is indicated by K409*.

The term "humanized antibody" as used herein refers to a genetically engineered non-human antibody, which contains human antibody constant domains and non-human variable domains modified to contain a high level of sequence homology to human variable domains. This can be achieved by grafting of the six non-human antibody CDRs, which together form the antigen binding site, onto a homologous human acceptor framework region (FR) (see WO92/22653 and EP0629240). In order to fully reconstitute the binding affinity and specificity of the parental antibody, the substitution of framework residues from the parental antibody (i.e., the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. The VH and VL of the CD3 arm that is used herein in DuoBody-CD3xCD20 represents a humanized antigen-binding region. Optionally, additional amino acid modifications, which are not necessarily back-mutations, may be applied to obtain a humanized antibody with preferred characteristics, such as affinity and biochemical properties.

The term "human antibody" as used herein refers to antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The VH and VL of the CD20 arm that is used in DuoBody-CD3xCD20 represents a human antigen-binding region. Human monoclonal antibodies of the invention can be produced by a variety of techniques, including conventional monoclonal antibody methodology, e.g., the standard somatic cell hybridization technique of Kohler and Milstein, *Nature* 256: 495 (1975). Although somatic cell hybridization procedures are preferred, in principle, other techniques for producing monoclonal antibody can be employed, e.g., viral or oncogenic transformation of B-lymphocytes or phage display techniques using libraries of human antibody genes. A suitable animal system for preparing hybridomas that secrete human monoclonal antibodies is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known. Human monoclonal antibodies can thus be generated using, e.g., transgenic or transchromosomal mice or rats carrying parts of the human immune system rather than the mouse or rat system. Accordingly, in one embodiment, a human antibody is obtained from a transgenic animal, such as a mouse or a rat, carrying human germline immunoglobulin sequences instead of animal immunoglobulin sequences. In such embodiments, the antibody originates from human germline immunoglobulin sequences introduced in the animal, but the final antibody sequence is the result of said human germline immunoglobulin sequences being further modified by somatic hyper-mutations and affinity maturation by the endogenous animal antibody machinery (see, e.g., Mendez et al. *Nat Genet* 1997; 15:146-56). The VH and VL regions of the CD20 arm that is used in DuoBody-CD3xCD20 represents a human antigen-binding region.

The term "biosimilar" (e.g., of an approved reference product/biological drug) as used herein refers to a biologic product that is similar to the reference product based on data from (a) analytical studies demonstrating that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is approved and intended to be used and for which approval is sought (e.g., that there are no clinically meaningful differences between the biological product and the reference product in terms of the safety, purity, and potency of the product). In some embodiments, the biosimilar biological product and reference product utilizes the same mechanism or mechanisms of action for the condition or conditions of use prescribed, recommended, or suggested in the proposed labeling, but only to the extent the mechanism or mechanisms of action are known for the reference product. In some embodiments, the condition or conditions of use prescribed, recommended, or suggested in the labeling proposed for the biological product have been previously approved for the reference product. In some embodiments, the route of administration, the dosage form, and/or the strength of the biological product are the same as those of the reference product. A biosimilar can be, e.g., a presently known antibody having the same primary amino acid sequence as a marketed antibody, but may be made in different cell types or by different production, purification, or formulation methods.

The term "reducing conditions" or "reducing environment" as used herein refers to a condition or an environment in which a substrate, here a cysteine residue in the hinge region of an antibody, is more likely to become reduced than oxidized.

The term "recombinant host cell" (or simply "host cell") as used herein is intended to refer to a cell into which an expression vector has been introduced, e.g., an expression vector encoding an antibody described herein. Recombinant host cells include, for example, transfectomas, such as CHO, CHO-S, HEK, HEK293, HEK-293F, Expi293F, PER.C6 or NS0 cells, and lymphocytic cells.

The term "follicular lymphoma" or "FL" as used herein refers to any of several types of non-Hodgkin's lymphoma in which the lymphomatous cells are clustered into nodules or follicles. The term "follicular" is used because the cells tend to grow in a circular, or nodular, pattern in lymph nodes. The malignant cells can be characterized by activation of the Bcl2 oncogene, typically via translocation t(14; 18), involving Ig heavy chain gene on chromosome 14 and the Bcl-2 on chromosome 18, and by expression of CD10, CD20, BCL2 and BCL6, but CD5 negative. FL typically has a slow disease course which persists essentially unchanged for years. FL can be classified in accordance with the WHO classification as defined in Swerdlow SH, Campo E, Harris NL, et al. WHO Classification of Tumours of Haematopoietic and Lymphoid Tissues (ed. 4th). Lyon, France: IARC Press (2008) and Swerdlow SH, Campo E, Harris NL, et al. WHO Classification of Tumours of Haematopoietic and Lymphoid Tissues (Revised ed. 4th). Lyon, France: IARC Press (2017), which are incorporated herein by reference.

The term "relapsed follicular lymphoma" or "relapsed FL" as used herein refers to follicular lymphoma which progressed after achieving partial (PR) or complete response (CR) to prior treatment with an anti-neoplastic therapy, such as immunochemotherapy containing an anti-CD20 antibody. The term "refractory follicular lymphoma" or "refractory FL" as used herein refers to follicular lymphoma which was treated with an anti-neoplastic therapy but failed to achieve at least a partial response to the therapy. The term "R/R follicular lymphoma" or "R/R FL" as used herein, unless specified otherwise, is intended to refer to relapsed and/or refractory follicular lymphoma.

The term "rituximab" (CAS Number: 174722-31-7; DrugBank—DB00073; Kyoto Encyclopedia of Genes and Genomes (KEGG) entry D02994) as used herein refers to a genetically engineered chimeric human gamma 1 murine constant domain containing monoclonal antibody against human CD20. The chimeric antibody contains human gamma 1 constant domains and is referred to as "C2B8" in U.S. Pat. No. 5,736,137 (the entire content of which is herein incorporated by reference). Rituximab is commercially available, for example, as Rituxan®, MabThera®, or Zytux®. In certain embodiments of the methods described herein, rituximab can be replaced with a biosimilar thereof. Accordingly, it will be understood that the term "rituximab" is intended to encompass biosimilars of rituximab. Also encompassed by the term "rituximab" are antibodies which have CDRs, variable regions, or heavy and light chains of rituximab. Non-limiting examples of biosimilars of rituximab include Truxima® (rituximab-abbs), Ruxience® (rituximab-pvvr), and Rixathon®. The biosimilar may be administered according to a standard of care dosage, or at a dose equivalent to the standard of care dosage specified for rituximab.

The term "bendamustine" as used herein refers to an alkylating agent with the chemical name 4-[5-[Bis(2-chloroethyl)amino]-1-methyl-1H-benzo[d]imidazole-2-yl]butanoic acid, and chemical formula $C_{16}H_{21}Cl_2N_3O_2$ (CAS No. 3543-75-7). Trade names include Ribomustin®, Treanda®, Bendeka®). Bendamustine can be provided in the form of bendamustine hydrochloride. The term "bendamustine" is also intended to encompass branded and generic versions (generic equivalents) of bendamustine, as well as pharmaceutically acceptable salts, isomers, racemates, solvates, complexes and hydrates, anhydrate forms thereof, and any polymorphic or amorphous forms thereof or combinations thereof.

The term "treatment" refers to the administration of an effective amount of a therapeutically active antibody described herein for the purpose of easing, ameliorating, arresting or eradicating (curing) symptoms or disease states such as follicular lymphoma. Treatment may result in a complete response (CR), partial response (PR), or stable disease (SD), for example, as defined by Lugano criteria and/or LYRIC. Treatment may be continued, for example, for up to two years total duration of treatment with the bispecific antibody from initiation of rituximab and bendamustine, or up to disease progression or unacceptable toxicity.

The term "administering" or "administration" as used herein refers to the physical introduction of a composition (or formulation) comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, a therapeutic agent described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods. In the methods described herein, the bispecific antibody (e.g., epcoritamab) is administered subcutaneously. Other agents used in combination with the bispecific antibody, such as for cytokine release syndrome prophylaxis and/or tumor lysis syndrome (TLS) prophylaxis, may be administered via other routes, such as intravenously or orally.

The term "effective amount" or "therapeutically effective amount" refers to an amount effective, at dosages and for periods of time necessary, to achieve a desired therapeutic result.

For example, dosages as defined herein for the bispecific antibody (e.g., epcoritamab), i.e., 24 mg or 48 mg, administered subcutaneously can be defined as such an "effective amount" or "therapeutically effective amount". A therapeutically effective amount of an antibody may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects. In some embodiments, patients treated with the methods described herein will show an improvement in ECOG performance status. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or disorder (e.g., cytokine release syndrome) or of suffering a recurrence of disease, inhibits the development or recurrence of the disease.

The term "inhibits growth" of a tumor as used herein includes any measurable decrease in the growth of a tumor, e.g., the inhibition of growth of a tumor by at least about 10%, for example, at least about 20%, at least about 30%, at least about 40%, at least about 50%, at least about 60%, at least about 70%, at least about 80%, at least about 90%, at least about 99%, or 100%.

The term "subject" as used herein refers to a human patient, for example, a human patient with follicular lymphoma. The terms "subject" and "patient" are used interchangeably herein.

The term "buffer" as used herein denotes a pharmaceutically acceptable buffer. The term "buffer" encompasses those agents which maintain the pH value of a solution, e.g., in an acceptable range and includes, but is not limited to, acetate, histidine, TRIS® (tris (hydroxymethyl) aminomethane), citrate, succinate, glycolate and the like. Generally, the "buffer" as used herein has a pKa and buffering capacity suitable for the pH range of about 5 to about 6, preferably of about 5.5.

"Disease progression" or "PD" as used herein refers to a situation in which one or more indices of follicular lymphoma show that the disease is advancing despite treatment. In one embodiment, disease progression is defined based on the Lugano Response Criteria for Malignant Lymphoma ("Lugano criteria") and/or Lymphoma Response to Immunomodulatory Therapy Criteria (LYRIC). Details regarding the Lugano criteria/classification system, including definitions for complete response (CR), partial response (PR), no response/stable disease (NR/SD), and progressive disease (PD) are provided in Cheson et al. *J Clin Oncol* 2014; 32:3059-68, the contents of which are incorporated by reference herein (see, in particular, Table 3 in Cheson et al., 2014). Details regarding LYRIC are provided in Table 8.

A "surfactant" as used herein is a compound that is typically used in pharmaceutical formulations to prevent drug adsorption to surfaces and or aggregation. Furthermore, surfactants lower the surface tension (or interfacial tension) between two liquids or between a liquid and a solid. For example, an exemplary surfactant can significantly lower the surface tension when present at very low concentrations (e.g., 5% w/v or less, such as 3% w/v or less, such as 1% w/v or less such as 0.4% w/v or less, such as below 0.1% w/v or less, such as 0.04% w/v). Surfactants are amphiphilic, which means they are usually composed of both hydrophilic and hydrophobic or lipophilic groups, thus being capable of forming micelles or similar self-assembled structures in aqueous solutions. Known surfactants for pharmaceutical use include glycerol monooleate, benzethonium chloride, sodium docusate, phospholipids, polyethylene alkyl ethers, sodium lauryl sulfate and tricaprylin (anionic surfactants); benzalkonium chloride, citrimide, cetylpyridinium chloride and phospholipids (cationic surfactants); and alpha tocopherol, glycerol monooleate, myristyl alcohol, phospholipids, poloxamers, polyoxyethylene alkyl ethers, polyoxyethylene castor oil derivatives, polyoxyethylene sorbintan fatty acid esters, polyoxyethylene sterarates, polyoxyl hydroxystearate, polyoxylglycerides, polysorbates such as polysorbate 20 or polysorbate 80, propylene glycol dilaurate, propylene glycol monolaurate, sorbitan esters sucrose palmitate, sucrose stearate, tricaprylin and TPGS (Nonionic and zwitterionic surfactants).

A "diluent" as used herein is one which is pharmaceutically acceptable (safe and non-toxic for administration to a human) and is useful for the preparation of dilutions of the pharmaceutical composition or pharmaceutical formulation (the terms "composition" and "formulation" are used interchangeably herein). Preferably, such dilutions of the composition dilute only the antibody concentration but not the buffer and stabilizer. Accordingly, in one embodiment, the diluent contains the same concentrations of the buffer and stabilizer as is present in the pharmaceutical composition of the invention. Further exemplary diluents include sterile water, bacteriostatic water for injection (BWFI), a pH buffered solution which is preferably an acetate buffer, sterile saline solution such as water for injection, Ringer's solution or dextrose solution. In one embodiment the diluent comprises or consists essentially of acetate buffer and sorbitol.

As used herein, the term "about" refers to a value that is no more than 10% above and no more than 10% below a specified value.

Follicular Lymphoma Treatment Regimens

Provided herein are methods of treating follicular lymphoma in a human subject using a bispecific antibody which binds to CD3 and CD20 ("anti-CD3xCD20 antibody"), e.g., an isolated anti-CD3xCD20 antibody such as epcoritamab which binds to human CD3 and human CD20, in combination with standard of care regimens of rituximab and bendamustine. The methods are useful for treating, e.g., newly diagnosed, previously untreated follicular lymphoma. It is understood that the methods of treating follicular lymphoma (e.g., newly-diagnosed, previously untreated follicular lymphoma) with a bispecific antibody which binds to both CD3 and CD20 described herein also encompass corresponding uses of the bispecific antibody for treating follicular lymphoma (e.g., newly-diagnosed, previously untreated follicular lymphoma) in a human subject.

Accordingly, in one aspect, provided herein is a method of treating follicular lymphoma in a human subject, the method comprising administering a bispecific antibody and an effective amount of rituximab (e.g., intravenously) and bendamustine (e.g., intravenously), wherein the bispecific antibody comprises:

(i) a first binding arm comprising a first antigen-binding region which binds to human CD3ε (epsilon) and comprises a variable heavy chain (VH) region and a variable light chain (VL) region, wherein the VH region comprises the CDR1, CDR2 and CDR3 sequences that are in the VH region sequence of SEQ ID NO: 6, and the VL region comprises the CDR1, CDR2 and CDR3 sequences that are in the VL region sequence of SEQ ID NO: 7; and (ii) a second binding arm comprising a second antigen-binding region which binds to human CD20 and comprises a VH region and a VL region, wherein the VH region comprises the CDR1, CDR2 and CDR3 sequences that are in the VH region sequence of SEQ ID NO: 13, and the VL region comprises the CDR1, CDR2 and CDR3 sequences that are in the VL region sequence of SEQ ID NO: 14;

wherein the bispecific antibody is administered at a dose of 24 mg or 48 mg, and wherein rituximab, bendamustine, and the bispecific antibody are administered in 28-day cycles.

In some embodiments, the bispecific antibody is administered at a dose of (or a dose of about) 24 mg. In some embodiments, the bispecific antibody is administered at a dose of (or a dose of about) 48 mg.

In some embodiments, the bispecific antibody is a full length antibody. In other embodiments, the bispecific antibody is an antibody with an inert Fc region. In yet other embodiments, the bispecific antibody is a full length antibody with an inert Fc region.

With regard to the dose of (or dose of about) 24 mg or 48 mg of the bispecific antibody that is to be administered, or any other specified dose, it is understood that this amount refers to the amount of a bispecific antibody representing a full-length antibody, such as epcoritamab as defined in the Examples section. Hence, one may refer to administering a dose of a bispecific antibody of 24 mg as administering a dose of a bispecific antibody described herein, wherein the dose corresponds to a dose of 24 mg of epcoritamab. One of ordinary skill in the art can readily determine the amount of antibody to be administered when, for example, the antibody used differs substantially in molecular weight from the molecular weight of a full-length antibody such as epcoritamab. For instance, the amount of antibody can be calculated by dividing the molecular weight of the antibody by the weight of a full-length antibody such as epcoritamab and multiplying the outcome thereof with the specified dose as described herein. As long as the bispecific antibody (e.g., a functional variant of DuoBody CD3xCD20) has highly similar features as DuoBody CD3xCD20, with regard to plasma half-life, Fc inertness, and/or binding characteristics for CD3 and CD20, i.e., with regard to CDRs and epitope binding features, such antibodies are suitable for use in the methods provided herein at a dose described for a full-length antibody such as epcoritamab.

In some embodiments, the dose of bispecific antibody is administered once a week (weekly administration) in 28-day cycles. In one embodiment, the weekly dose of 24 mg or 48 mg is administered for 2.5 28-day cycles (i.e., 10 times; on days 15 and 22 of cycle 1, and days 1, 8, 15, and 22 of cycles 2 and 3). In other embodiments, after the weekly administration, one may reduce the interval of administration to once every two weeks (biweekly administration). In one embodiment, the biweekly administration is performed for six 28-day cycles (i.e., 12 times). In some embodiments, after the biweekly administration, one may reduce the interval of administration to once every four weeks. In one embodiment, the administration once every four weeks may be performed for an extended period, for example, for at least 1 cycle, at least 2 cycles, at least 3 cycles, at least 4 cycles, at least 5 cycles, at least 6 cycles, at least 7 cycles, at least 8 cycles, at least 9 cycles, at least 10 cycles, at least 11 cycles, at least 12 cycles, at least 13 cycles, at least 14 cycles, at least 15 cycles, at least 16 cycles, at least 17 cycles, 1-20 cycles, 1-19 cycles, 1-18 cycles, 1-17 cycles, 1-16 cycles, 1-15 cycles, 1-14 cycles, 1-13 cycles, 1-12 cycles, 1-10 cycles, 1-5 cycles, 5-20 cycles, 5-15 cycles, or 5-10 cycles of the 28-day cycles. In some embodiments, the bispecific antibody is administered as monotherapy (i.e., without rituximab or bendamustine) from cycle 7 of the 28-day cycles. In some embodiments, the bispecific antibody is administered as monotherapy from cycle 7 to cycle 26 of the 28-day cycles. In some embodiments, the bispecific antibody is administered as monotherapy from cycle 7 of the 28-day cycles for up to two years total duration of treatment with the bispecific antibody from initiation of rituximab and bendamustine, or until disease progression (e.g., as defined by the Lugano criteria or LYRIC) or unacceptable toxicity.

In one embodiment, the weekly dose of the bispecific antibody is administered in 28-day cycles on cycles 1-3 (which may include priming and intermediate doses, as described below), the biweekly dose of the bispecific antibody is administered on cycles 4-9, and the dose once every four weeks is administered from cycle 10 onwards, for example, on cycles 10-15, cycles 10-20, cycles 10-25, cycles 10-30, or more cycles, e.g., for up to two years total duration of treatment with the bispecific antibody from initiation of rituximab and bendamustine, or until disease progression or unacceptable toxicity is observed in the subject. In some embodiments, the dose once every four weeks is administered on cycles 10-26.

It is understood that the doses referred to herein may also be referred to as a full or a flat dose in the scenarios above wherein, e.g., the weekly dose, biweekly dose, and/or the dose every four weeks is administered is at the same level. Accordingly, when a dose of 48 mg is selected, preferably, at each weekly administration, at each biweekly administration, and each administration every four weeks, the same dose of 48 mg is administered. Prior to administering the dose, a priming or a priming and subsequent intermediate (second priming) dose may be administered. This may be advantageous as it may help mitigate cytokine release syndrome (CRS) risk and severity, a side-effect that can occur during treatment with the bispecific anti-CD3xCD20 antibody described herein. Such priming, or priming and intermediate doses, are at a lower dose as compared with the flat or full dose.

Accordingly, in some embodiments, prior to administering the weekly dose of 24 mg or 48 mg, a priming dose of the bispecific antibody may be administered. In one embodiment, the priming dose is administered two weeks prior to administering the first weekly dose of 24 mg or 48 mg in cycle 1. In one embodiment, the priming dose is 0.16 mg (or about 0.16 mg) of the full-length bispecific antibody.

In some embodiments, after administering the priming dose and prior to administering the weekly dose of 24 mg or 48 mg, an intermediate dose of said bispecific antibody is administered. In one embodiment, the priming dose is administered one week before the intermediate dose (i.e., on day 1 of cycle 1), and the intermediate dose is administered one week before the first weekly dose of 24 mg or 48 mg (i.e., on day 8 of cycle 1). In one embodiment, the intermediate dose is 800 µg (0.8 mg) or about 800 µg (0.8 mg) of the full-length bispecific antibody.

The methods described herein involve treating human subjects who have follicular lymphoma with a bispecific antibody which binds to CD3 and CD20 in combination with a standard-of-care regimen of rituximab and bendamustine.

In some embodiments, rituximab and bendamustine are administered at standard-of-care dosages, e.g., as supported by clinical studies, according to local guidelines, and/or according to relevant local labels.

In some embodiments, rituximab is administered according to the product label or summary of product characteristics (see, e.g., RITUXAN® (rituximab) prescribing information, available at www.accessdata.fda.gov/drugsatfda_docs/label/2013/103705s5414lbl.pdf). In some embodiments, a biosimilar of rituximab is used in place of rituximab in the methods described herein.

In some embodiments, bendamustine is administered according to the product label or summary of product characteristics (see, e.g., TREANDA® (bendamustine hydrochloride) for injection prescribing information, available at www.accessdata.fda.gov/drugsatfda_docs/label/2008/022303lbl.pdf; BENDEKA® (bendamustine hydrochloride) injection prescribing information available at www.accessdata.fda.gov/drugsatfda_docs/label/2015/208194s000lbl.pdf. In some embodiments, bendamustine is in the form of bendamustine hydrochloride. In some embodiments, bendamustine is in the form of a solution. In other embodiments, bendamustine is in the form of a lyophilized powder.

In one embodiment, rituximab is administered according to local guidelines and local labels. In some embodiments, rituximab is administered at a dose of (or a dose of about) 375 mg/m². In yet some embodiments, rituximab is administered intravenously.

In one embodiment, rituximab is administered once every four weeks (Q4W) in 28-day cycles. In yet some embodiments, administration of rituximab once every four weeks is performed for six 28-day cycles (i.e., 6 times).

In one embodiment, bendamustine is administered according to local guidelines and local labels. In some embodiments, bendamustine is administered at a dose of (or a dose of about) 90 mg/m². In some embodiments, bendamustine is administered intravenously.

In one embodiment, bendamustine is administered for two consecutive days (i.e., days 1-2) in 28-day cycles. In some embodiments, bendamustine is administered for six 28-day cycles (i.e., on days 1-2 of cycles 1-6 of the 28-day cycles).

In one embodiment, administration of bendamustine is delayed when a subject presents with bendamustine-related toxicity (Grade 3 hematologic toxicity or ≥Grade 2 non-hematologic toxicity) during a treatment cycle in accordance with standard of care guidelines, for example, as specified in the product label. In some embodiments, bendamustine is re-initiated once non-hematologic toxicity has recovered (e.g., to ≤Grade 1) and/or blood counts improve (ANC ≥1.0×10⁹/L with a platelet count ≥75×10⁹/L). In some embodiments, for Grade 3 hematologic toxicity lasting more than 2 days, the dose of bendamustine is reduced to 70 mg/m² on days 1 and 2 of each cycle. In a further embodiment, for Grade 4 hematologic toxicity, the dose of bendamustine is reduced to 60 mg/m² on days 1 and 2 of each cycle. In some embodiments, for ≥Grade 3 non-hematologic toxicity, the dose of bendamustine is reduced to 60 mg/m² on days 1 and 2 of each cycle.

In certain embodiments, the bispecific antibody, rituximab, and/or bendamustine are administered simultaneously.

In other embodiments, the bispecific antibody, rituximab, and/or bendamustine are administered sequentially. For instance, in one embodiment, rituximab is administered before the bispecific antibody if rituximab and the bispecific antibody are administered on the same day (e.g., day 1 of cycles 1-6 of 28-day cycles). In some embodiments, bendamustine is administered before the bispecific antibody if bendamustine and the bispecific antibody are administered on the same day (e.g., day 1 of cycles 1-6 of 28-day cycles). In some embodiments, rituximab is administered before bendamustine if rituximab and bendamustine are administered on the same day (e.g., day 1 of cycles 1-6 of 28-day cycles). In a further embodiment, rituximab is administered first, bendamustine is administered second, and the bispecific antibody is administered last if rituximab, bendamustine, and the bispecific antibody are administered on the same day (e.g., day 1 of cycles 1-6 of 28-day cycles). In some embodiments, if administered on the same day, (a) rituximab is administered before the bispecific antibody (e.g., day 1 of cycles 1-6); (b) bendamustine is administered before the bispecific antibody (e.g., day 1 of cycles 1-6); (c) bendamustine is administered before rituximab (e.g., day 1 of cycles 1-6); or (d) bendamustine is administered first, rituximab is administered second, and the bispecific antibody is administered last (e.g., day 1 of cycles 1-6).

In some embodiments, the subject is administered pre-medication and/or prophylaxis for CRS prior to administration of rituximab, bendamustine, and the bispecific antibody.

In some embodiments, rituximab (e.g., intravenous), bendamustine (e.g., intravenous), and the bispecific antibody (e.g., subcutaneous) are administered in 28-day cycles, wherein:
(a) the bispecific antibody is administered as follows:
  (i) in cycle 1, a priming dose of 0.16 mg is administered on day 1, an intermediate dose of 0.8 mg is administered on day 8, and a dose of 24 mg is administered on days 15 and 22;
  (ii) in cycles 2 and 3, a dose of 24 mg is administered on days 1, 8, 15, and 22;
  (iii) in cycles 4-9, a dose of 24 mg is administered on days 1 and 15; and
  (iv) in cycle 10 and subsequent cycles (e.g., cycles 10-15, cycles 10-20, cycles 10-25, or more cycles), a dose of 24 mg is administered on day 1;
(b) rituximab is administered on day 1 in cycles 1-6; and
(c) bendamustine is administered on days 1 and 2 in cycles 1-6.

In some embodiments, rituximab (e.g., intravenous), bendamustine (e.g., intravenous), and the bispecific antibody (e.g., subcutaneous) are administered in 28-day cycles, wherein:
(a) the bispecific antibody is administered as follows:
  (i) in cycle 1, a priming dose of 0.16 mg is administered on day 1, an intermediate dose of 0.8 mg is administered on day 8, and a dose of 48 mg is administered on days 15 and 22;
  (ii) in cycles 2 and 3, a dose of 48 mg is administered on days 1, 8, 15, and 22;
  (iii) in cycles 4-9, a dose of 48 mg is administered on days 1 and 15; and
  (iv) in cycle 10 and subsequent cycles (e.g., cycles 10-15, cycles 10-20, cycles 10-25, or more cycles), a dose of 48 mg is administered on day 1;
(b) rituximab is administered on day 1 in cycles 1-6; and
(c) bendamustine is administered on days 1 and 2 in cycles 1-6.

In some embodiments, rituximab (e.g., intravenous), bendamustine (e.g., intravenous), and the bispecific antibody epcoritamab (e.g., subcutaneous) are administered in 28-day cycles, wherein:
(a) the bispecific antibody epcoritamab is administered as follows:
  (i) in cycle 1, a priming dose of 0.16 mg is administered on day 1, an intermediate dose of 0.8 mg is administered on day 8, and a dose of 24 mg is administered on days 15 and 22;
  (ii) in cycles 2 and 3, a dose of 24 mg is administered on days 1, 8, 15, and 22;
  (iii) in cycles 4-9, a dose of 24 mg is administered on days 1 and 15; and
  (iv) in cycle 10 and subsequent cycles (e.g., cycles 10-15, cycles 10-20, cycles 10-25, or more cycles), a dose of 24 mg is administered on day 1;
(b) rituximab is administered on day 1 in cycles 1-6; and
(c) bendamustine is administered on days 1 and 2 in cycles 1-6.

In some embodiments, rituximab (e.g., intravenous), bendamustine (e.g., intravenous), and the bispecific antibody epcoritamab (e.g., subcutaneous) are administered in 28-day cycles, wherein:
(a) the bispecific antibody epcoritamab is administered as follows:

(i) in cycle 1, a priming dose of 0.16 mg is administered on day 1, an intermediate dose of 0.8 mg is administered on day 8, and a dose of 48 mg is administered on days 15 and 22;

(ii) in cycles 2 and 3, a dose of 48 mg is administered on days 1, 8, 15, and 22;

(iii) in cycles 4-9, a dose of 48 mg is administered on days 1 and 15; and (iv) in cycle 10 and subsequent cycles (e.g., cycles 10-15, cycles 10-20, cycles 10-25, or more cycles), a dose of 48 mg is administered on day 1;

(b) rituximab is administered on day 1 in cycles 1-6; and (c) bendamustine is administered on days 1 and 2 in cycles 1-6.

In some embodiments, rituximab (e.g., intravenous), bendamustine (e.g., intravenous), and the bispecific antibody (e.g., subcutaneous) are administered in 28-day cycles, wherein:

(a) the bispecific antibody is administered as follows:

(i) in cycle 1, a priming dose of 0.16 mg is administered on day 1, an intermediate dose of 0.8 mg is administered on day 8, and a dose of 24 mg is administered on days 15 and 22;

(ii) in cycles 2 and 3, a dose of 24 mg is administered on days 1, 8, 15, and 22;

(iii) in cycles 4-9, a dose of 24 mg is administered on days 1 and 15; and (iv) in cycle 10 and subsequent cycles (e.g., cycles 10-15, cycles 10-20, cycles 10-25, or more cycles), a dose of 24 mg is administered on day 1;

(b) rituximab is administered on day 1 in cycles 1-6 at a dose of 375 mg/m2; and (c) bendamustine is administered on days 1 and 2 in cycles 1-6 at a dose of 90 mg/m2.

In one embodiment, rituximab (e.g., intravenous), bendamustine (e.g., intravenous), and the bispecific antibody (e.g., subcutaneous) are administered in 28-day cycles, wherein:

(a) the bispecific antibody is administered as follows:

(i) in cycle 1, a priming dose of 0.16 mg is administered on day 1, an intermediate dose of 0.8 mg is administered on day 8, and a dose of 48 mg is administered on days 15 and 22;

(ii) in cycles 2 and 3, a dose of 48 mg is administered on days 1, 8, 15, and 22;

(iii) in cycles 4-9, a dose of 48 mg is administered on days 1 and 15; and (iv) in cycle 10 and subsequent cycles (e.g., cycles 10-15, cycles 10-20, cycles 10-25, or more cycles), a dose of 48 mg is administered on day 1;

(b) rituximab is administered on day 1 in cycles 1-6 at a dose of 375 mg/m2; and (c) bendamustine is administered on days 1 and 2 in cycles 1-6 at a dose of 90 mg/m2.

In some embodiments, rituximab (e.g., intravenous), bendamustine (e.g., intravenous), and the bispecific antibody epcoritamab (e.g., subcutaneous) are administered in 28-day cycles, wherein:

(a) the bispecific antibody epcoritamab is administered as follows:

(i) in cycle 1, a priming dose of 0.16 mg is administered on day 1, an intermediate dose of 0.8 mg is administered on day 8, and a dose of 24 mg is administered on days 15 and 22;

(ii) in cycles 2 and 3, a dose of 24 mg is administered on days 1, 8, 15, and 22;

(iii) in cycles 4-9, a dose of 24 mg is administered on days 1 and 15; and (iv) in cycle 10 and subsequent cycles (e.g., cycles 10-15, cycles 10-20, cycles 10-25, or more cycles), a dose of 24 mg is administered on day 1;

(b) rituximab is administered on day 1 in cycles 1-6 at a dose of 375 mg/m2; and (c) bendamustine is administered on days 1 and 2 in cycles 1-6 at a dose of 90 mg/m2.

In some embodiments, rituximab (e.g., intravenous), bendamustine (e.g., intravenous), and the bispecific antibody epcoritamab (e.g., subcutaneous) are administered in 28-day cycles, wherein:

(a) the bispecific antibody epcoritamab is administered as follows:

(i) in cycle 1, a priming dose of 0.16 mg is administered on day 1, an intermediate dose of 0.8 mg is administered on day 8, and a dose of 48 mg is administered on days 15 and 22;

(ii) in cycles 2 and 3, a dose of 48 mg is administered on days 1, 8, 15, and 22;

(iii) in cycles 4-9, a dose of 48 mg is administered on days 1 and 15; and (iv) in cycle 10 and subsequent cycles (e.g., cycles 10-15, cycles 10-20, cycles 10-25, or more cycles), a dose of 48 mg is administered on day 1;

((b) rituximab is administered on day 1 in cycles 1-6 at a dose of 375 mg/m2; and (c) bendamustine is administered on days 1 and 2 in cycles 1-6 at a dose of 90 mg/m2.In some embodiments, subjects considered to be at risk of thrombosis are administered prophylactic antithrombotic treatment, such as low-dose aspirin (e.g., 70-100 mg daily). In certain embodiments, subjects with a prior history of deep vein thrombosis (DVT) or pulmonary embolism (PE) are administered anticoagulation therapy.

In some embodiments, the subject undergoing the treatment with the methods described herein has histologically confirmed CD20+ follicular lymphoma.

In some embodiments, the subject has previously untreated follicular lymphoma of Grade 1, 2, or 3a. In some embodiments, the subject has previously untreated follicular lymphoma of Stage II, III, or IV.

In some embodiments, the subject has an Eastern Cooperative Oncology Group (ECOG) performance status (ECOG PS) of 0, 1, or 2. Information regarding ECOG PS scores can be found in, e.g., Oken et al, *Am J Clin Oncol* 1982 December; 5(6):649-55).

In some embodiments, the subject has measurable disease as defined as (a) ≥1 measurable nodal lesion (long axis >1.5 cm and short axis >1.0 cm) or ≥1 measurable extra-nodal lesion (long axis >1 cm) on CT or MRI.

In some embodiments, the subject has acceptable organ function as defined as: (a) ANC $\geq 1.0 \times 10^9$/L, (b) platelet count $>75 \times 10^9$/L, or $\geq 50 \times 10^9$/L if bone marrow infiltration or splenomegaly, (c) ALT level ≤2.5 times the ULN, (d) total bilirubin level ≤2×ULN, (e) eGFR >50 mL/min (by Cockcroft-Gault Formula), and (f) PT, INR, and aPTT≤1.5×ULN (unless receiving anticoagulant).

In some embodiments, the subject does not have severe allergic or anaphylactic reactions to anti-CD20 antibody therapy, bendamustine, or the bispecific antibody, or known allergy or intolerance to any component or excipient of rituximab, bendamustine, and/or the bispecific antibody.

In some embodiments, the subject does not have clinically significant cardiac disease, including (a) myocardial infarction within one year prior to the first dose of the bispecific antibody, or unstable or uncontrolled disease/condition related to or affecting cardiac function (e.g., unstable angina, congestive heart failure, NYHA class III-IV), cardiac arrhythmia (CTCAE Version 4 Grade 2 or higher), or clinically significant ECG abnormalities, and/or (b) 12-lead ECG showing a baseline QTcF >470 msec.

In some embodiments, the subject does not have a contraindication to bendamustine or rituximab.

A human subject receiving a treatment described herein may be a patient having one or more of the inclusion criteria set forth in Example 3, or not having one or more of the exclusion criteria set forth in Example 3.

The methods described herein are advantageous for treating follicular lymphoma, such as previously untreated follicular lymphoma. The treatment is maintained continuously using, e.g., the treatment regimens described herein. However, treatment may be terminated when progressive disease develops, or unacceptable toxicity occurs.

The response of subjects with follicular lymphoma to treatment using the methods described herein may be assessed according to the Lugano Response Criteria for Malignant Lymphoma (also referred to as "Lugano criteria" herein) and/or Lymphoma Response to Immunomodulatory Therapy Criteria (also referred to as "LYRIC" herein), as described in Example 3. In one embodiment, complete response (CR), partial response (PR), and stable disease (SD) are assessed using the Lugano criteria. In some embodiments, patients showing disease progression, also referred to as progressive disease (PD), according to the Lugano criteria are further evaluated according to LYRIC. Details regarding the Lugano criteria/classification system, including definitions for complete response, partial response, no response/stable disease, and progressive disease are provided in Cheson et al. *J Clin Oncol* 2014; 32:3059-68 (see, in particular, Table 3 in Cheson et al., 2014). Details regarding LYRIC are provided in Table 8.

In some embodiments, subjects are treated with the methods described herein until they show disease progression (PD), e.g., as defined by Lugano criteria and/or LYRIC. In one embodiment, subjects are treated with the methods described herein until they show disease progression (PD) as defined by both Lugano criteria and LYRIC. In some embodiments, the subjects are treated with the methods described herein for up to two years total duration of treatment with the bispecific antibody from initiation of rituximab and bendamustine.

Subjects treated according to the methods described herein preferably experience improvement in at least one sign of follicular lymphoma. In one embodiment, improvement is measured by a reduction in the quantity and/or size of measurable tumor lesions. In some embodiments, lesions can be measured on CT, PET-CT, or MRI films. In some embodiments, cytology or histology can be used to evaluate responsiveness to a therapy. In some embodiments, bone marrow aspirate and bone marrow biopsy can be used to evaluate response to therapy. In one embodiment, the subject treated exhibits a complete response (CR), a partial response (PR), or stable disease (SD), as defined by the Lugano criteria or LYRIC (see, e.g., Table 8). In some embodiments, the methods described herein produce at least one therapeutic effect chosen from prolonged survival, such as progression-free survival or overall survival, optionally compared to another therapy or placebo.

Cytokine release syndrome (CRS) can occur when methods are used in human subjects that utilize immune cell- and bispecific antibody-based approaches that function by activation of immune effector cell, such as by engaging CD3 (Lee et al., *Biol Blood Marrow Transplant* 2019; 25:625-38, which is incorporated herein by reference). Hence, in some embodiments, CRS mitigation is performed together with the methods described herein. As part of CRS mitigation, the selection of a priming dose and/or intermediate dose is performed prior to administering the full dose (e.g., 24 or 48 mg), as described herein. CRS can be classified in accordance with standard practice (e.g. as outlined in Lee et al., *Biol Blood Marrow Transplant* 2019; 25:625-38, which is incorporated herein by reference). CRS may include excessive release of cytokines, for example of proinflammatory cytokines, e.g., IL-6, TNF-alpha, or IL-8, that may result in adverse effects like fever, nausea, vomiting and chills. Thus, despite the unique anti-tumor activity of bispecific antibodies such as epcoritamab, their immunological mode of action may trigger unwanted "side" effects, i.e., the induction of unwanted inflammatory reactions. Hence, patients may be further subjected to a concomitant treatment, prophylaxis, and/or premedication with, e.g., analgesics, antipyretics, and/or anti-inflammatory drugs to mitigate possible CRS symptoms.

Accordingly, in one embodiment, human subjects in the methods described herein are treated with prophylaxis for CRS. In some embodiments, the prophylaxis includes the administration of a corticosteroid. In one embodiment, the prophylaxis is administered on the same day as the bispecific antibody. The prophylaxis can also be administered on the subsequent day as well, more preferably on subsequent days 2, 3, and 4. It is understood that days 2, 3 and 4 when relating to further medication, such as prophylaxis, is relative to the administration of the bispecific antibody which is administered on day 1. For example, when in a cycle the antibody is administered on day 15, and prophylaxis is also administered, the prophylaxis corresponding to days 2, 3 and 4 are days 16, 17, and 18 of the cycle. In some embodiments, the prophylaxis is administered on the day when the bispecific antibody is administered and on subsequent days 2-4. When said prophylaxis is administered on the same day as the bispecific antibody, the prophylaxis is preferably administered 30-120 minutes prior to said administration of the bispecific antibody. An exemplary corticosteroid suitable for use in the methods and uses described herein is prednisolone. In some embodiments, prednisolone is administered at an intravenous dose of 100 mg, or an equivalent thereof, including an oral dose. Exemplary corticosteroid equivalents of prednisolone, along with dosage equivalents, which can be used for CRS prophylaxis are shown in Table 5.

Furthermore, in some embodiments, human subjects in the methods described herein are treated with premedication to reduce reactions to injections. In one embodiment, the premedication includes the administration of antihistamines. In some embodiments, the premedication includes the administration of antipyretics. In a further embodiment, the premedication includes systemic administration of antihistamines and antipyretics.

An exemplary antihistamine suitable for use in premedication is diphenhydramine. In one embodiment, diphenhydramine is administered at an intravenous or oral dose 50 mg, or an equivalent thereof. An exemplary antipyretic suitable for use in premedication is acetaminophen. In one embodiment, acetaminophen is administered at an oral dose of 650-1000 mg, or equivalent thereof. In some embodiments, the premedication is administered on the same day as the bispecific antibody, for example, prior to the injection with the bispecific antibody, e.g., 30-120 minutes prior to administration of the bispecific antibody.

Premedication and/or prophylaxis for CRS can be administered at least in the initial phase of the treatment. In some embodiments, premedication and/or prophylaxis is administered during the first four administrations of the bispecific antibody. For example, the prophylaxis can be administered as described herein, during the first 28-day cycle of the bispecific antibody administration. In some embodiments, the premedication is administered during said first cycle.

Usually, risk of reactions during the initial treatment subsides after a few administrations, e.g., after the first four administrations (first cycle). Hence, when the human subject does not experience CRS with the fourth administration, prophylaxis for CRS may be stopped. However, CRS prophylaxis may continue, particularly when the human subject experiences a CRS greater than grade 1. Likewise, premedication may also optionally continue. CRS grading can be performed as described in Tables 6 and 7.

In a further embodiment, in the methods described herein, the prophylaxis for CRS is administered during the second 28-day cycle when the human subject experiences CRS greater than grade 1 after the fourth administration of the bispecific antibody in cycle 1. Furthermore, the prophylaxis can be continued during a subsequent cycle, when in the last administration of the bispecific antibody of the previous cycle, the human subject experiences CRS greater than grade 1. Any premedication may be optionally administered during the second cycle. Further premedication may be optionally administered during subsequent cycles as well.

In one embodiment, premedication and prophylaxis for CRS is administered, including an antihistamine such as diphenhydramine (e.g., at an intravenous or oral dose 50 mg, or an equivalent thereof), an antipyretic such as acetaminophen (e.g., at an oral dose of 650-1000 mg, or an equivalent thereof), and a corticosteroid such as prednisolone (e.g., at an intravenous dose of 100 mg, or an equivalent thereof). In some embodiments, the premedication and prophylaxis is administered 30-120 minutes prior to administration of the bispecific antibody. On subsequent days 2, 3, and optionally day 4, further prophylaxis is administered comprising the systemic administration of a corticosteroid such as prednisolone (e.g., at an intravenous dose of 100 mg, or an equivalent thereof). In some embodiments, the premedication and prophylaxis schedule preferably is administered during the first four administrations of the bispecific antibody, e.g., during the first 28-day cycle of bispecific antibody administration described herein. Furthermore, subsequent cycles, in case of, e.g., CRS greater than grade 1 occurring during the last administration of the prior cycle, can include the same administration schedule, wherein the premedication as part of the administration schedule is optional.

During the treatment of a human subject with follicular lymphoma using the doses and treatment regimens described herein, CRS can be well managed while at the same time effectively controlling and/or treating the follicular lymphoma. As described in the Examples, subjects treated with the methods described herein may experience manageable CRS. In some cases, subjects receiving the treatment described herein may develop CRS of grade 1 as defined in accordance with standard practice. In other cases, subjects may develop manageable CRS of grade 2 as defined in accordance with standard practice. Hence, subjects receiving the treatments described herein may have manageable CRS of grade 1 or grade 2 during as defined in accordance with standard practice. In accordance with standard classification for CRS, a grade 1 CRS includes a fever to at least 38° C., no hypotension, no hypoxia, and a grade 2 CRS includes a fever to at least 38° C. plus hypotension, not requiring vasopressors and/or hypoxia requiring oxygen by low flow nasal cannula or blow by. Such manageable CRS can occur during cycle 1. Human subjects receiving the treatments described herein may also have CRS greater than grade 2 during the treatments as defined in accordance with standard practice. Hence, human subjects receiving the treatments described herein may also have CRS of grade 3 during said treatments as defined in accordance with standard practice. Such manageable CRS may further occur during cycle 1 and subsequent cycles.

Human subjects treated according to the methods described herein may also experience pyrexia, fatigue, and injection site reactions. They may also experience neurotoxicity, partial seizures, agraphia related to CRS, or confusional state related to CRS.

As mentioned above, subjects may develop CRS during treatment with the methods described herein, despite having received CRS prophylaxis. CRS grading criteria are described in Tables 6 and 7.

In one embodiment, subjects who develop Grade 1 CRS are treated with antibiotics if they present with infection. In some embodiments, the antibiotics are continued until neutropenia, if present, resolves. In some embodiments, subjects with Grade 1 CRS who exhibit constitutional symptoms are treated with NSAIDs.

In one embodiments, subjects who develop Grade 2 CRS are treated with intravenous fluid boluses and/or supplemental oxygen. In some embodiments, subjects who develop Grade 2 CRS are treated with a vasopressor. In some embodiments, subjects with Grade 2 CRS with comorbidities are treated with tocilizumab (a humanized antibody against IL-6 receptor, commercially available as, e.g., ACTEMRA®) and/or steroids (e.g., dexamethasone or its equivalent of methylprednisolone). In a further embodiment, a subject who presents with concurrent ICANS is administered dexamethasone. In yet a further embodiment, if the subject does not show improvement in CRS symptoms within, e.g., 6 hours, or if the subject starts to deteriorate after initial improvement, then a second dose of tocilizumab is administered together with a dose of corticosteroids. In some embodiments, if the subject is refractory to tocilizumab after three administrations, then additional cytokine therapy, e.g., an anti-IL-6 antibody (e.g., siltuximab) or an IL-1R antagonist (e.g., anakinra) is administered to the subject.

In one embodiment, subjects who develop Grade 3 CRS are treated with vasopressor (e.g., norepinephrine) support and/or supplemental oxygen. In some embodiments, subjects with Grade 3 CRS are treated with tocilizumab, or tocilizumab in combination with steroids (e.g., dexamethasone or its equivalent of methylprednisolone). In yet some embodiments, a subject who presents with concurrent ICANS is administered dexamethasone. In a further embodiment, if the subject is refractory to tocilizumab after three administrations, then additional cytokine therapy, e.g., an anti-IL-6 antibody (e.g., siltuximab) or an IL-1R antagonist (e.g., anakinra) is administered to the subject.

In one embodiment, subjects who develop Grade 4 CRS are treated with vasopressor support and/or supplemental oxygen (e.g., via positive pressure ventilation, such as CPAP, BiPAP, intubation, or mechanical ventilation). In some embodiments, the subject is administered at least two vasopressors. In some embodiments, the subject is administered tocilizumab and a steroid. In a further embodiment, a subject who presents with concurrent ICANS is administered dexamethasone. In yet a further embodiment, if the subject is refractory to tocilizumab after three administrations, then additional cytokine therapy, e.g., an anti-IL-6 antibody (e.g., siltuximab) or an IL-1R antagonist (e.g., anakinra) is administered to the subject.

In some embodiments, the human subject receives prophylactic treatment for tumor lysis syndrome (TLS). Classification and grading of tumor lysis syndrome can be performed using methods known in the art, for example, as described in Howard et al. *N Engl J Med* 2011; 364:1844-54, and Coiffier et al., *J Clin Oncol* 2008; 26:2767-78. In some embodiments, prophylactic treatment of TLS comprises administering one or more uric acid reducing agents prior to administering the bispecific antibody. Exemplary uric acid reducing agents include rasburicase and allopurinol. Accordingly, in one embodiment, the prophylactic treatment of TLS comprises administering rasburicase and/or allopurinol prior to administering the bispecific antibody. In some embodiments, when the subject shows signs of TLS, supportive therapy, such as rasburicase, may be used.

Subjects being administered rituximab according to the methods described herein can be treated with supportive therapies. In one embodiment, supportive therapies include, but are not limited to, (a) premedication with acetaminophen (e.g., 650 mg orally), diphenhydramine (e.g., 50-100 mg intravenously or orally), and steroids, for example, 30-60 minutes prior to starting each rituximab infusion, (b) prophylactic treatment for *Pneumocystis carinii* pneumonia, (c) CNS prophylaxis according to standard local practice (e.g., methotrexate), (d) low-dose aspirin (e.g., 70-100 mg daily) or another prophylactic antithrombotic treatment for subjects without a prior history of deep vein thrombosis (DVT) or pulmonary embolism (PE) within 5 years of initiating treatment and considered to be at standard risk for thrombosis, and/or (e) anticoagulation therapy for subjects with a prior medical history of DVT or PE within 5 years of initiating treatment.

In one embodiment, the bispecific antibody is administered subcutaneously, and thus is formulated in a pharmaceutical composition such that it is compatible with subcutaneous (s.c.) administration, i.e., having a formulation and/or concentration that allows pharmaceutical acceptable s.c. administration at the doses described herein. In some embodiments, subcutaneous administration is carried out by injection. For example, formulations for DuoBody-CD3xCD20 that are compatible with subcutaneous formulation and can be used in the methods described herein have been described previously (see, e.g., WO2019155008, which is incorporated herein by reference). In some embodiments, the bispecific antibody may be formulated using sodium acetate trihydrate, acetic acid, sodium hydroxide, sorbitol, polysorbate 80, and water for injection, and have a pH of 5.5 or about 5.5. In some embodiments, the bispecific antibody is provided as a 5 mg/mL or 60 mg/mL concentrate. In other embodiments, the desired dose of the bispecific antibody is reconstituted to a volume of about 1 mL for subcutaneous injection.

In one embodiment, a suitable pharmaceutical composition for the bispecific antibody can comprise the bispecific antibody, 20-40 mM acetate, 140-160 mM sorbitol, and a surfactant, such as polysorbate 80, and having a pH of 5.3-5.6. In some embodiments, the pharmaceutical formulation may comprise an antibody concentration in the range of 5-100 mg/mL, e.g., 48 or 60 mg/mL of the bispecific antibody, 30 mM acetate, 150 mM sorbitol, 0.04% w/v polysorbate 80, and have a pH of 5.5. Such a formulation may be diluted with, e.g., the formulation buffer to allow proper dosing and subcutaneous administration.

The volume of the pharmaceutical composition is appropriately selected to allow for subcutaneous administration of the antibody. For example, the volume to be administered is in the range of about 0.3 mL to about 3 mL, such as from 0.3 mL to 3 mL. The volume to be administered can be 0.5 mL, 0.8 mL, 1 mL, 1.2 mL, 1.5 ml, 1.7 mL, 2 mL, or 2.5 mL, or about 0.5 mL, about 0.8 mL, about 1 mL, about 1.2 mL, about 1.5 ml, about 1.7 mL, about 2 mL, or about 2.5 mL. Accordingly, in one embodiment, the volume to be administered is 0.5 mL or about 0.5 mL. In some embodiments, the volume to be administered is 0.8 mL or about 0.8 mL. In some embodiments, the volume to be administered is 1 mL or about 1 mL. In some embodiments, the volume to be administered is 1.2 mL or about 1.2 mL. In some embodiments, the volume to be administered is 1.5 mL or about 1.5 mL. In some embodiments, the volume to be administered is 1.7 mL or about 1.7 mL. In some embodiments, the volume to be administered is 2 mL or about 2 mL. In some embodiments, the volume to be administered is 2.5 mL or about 2.5 mL.

In one embodiment, rituximab is formulated in a pharmaceutical composition comprising pharmaceutically-acceptable excipients for administration (e.g., intravenous administration) in accordance with local standard-of-care practice, e.g., as specified by local guidelines or local product labels. For example, in some embodiments, rituximab is provided as a sterile, clear, colorless, preservative-free liquid concentrate for intravenous administration. In one embodiment, rituximab is supplied at a concentration of 10 mg/mL in either 100 mg/10 mL or 500 mg/50 mL single-use vials. In some embodiments, rituximab is formulated in polysorbate 80 (0.7 mg/mL), sodium citrate dihydrate (7.35 mg/mL), sodium chloride (9 mg/mL), and water, at a pH of 6.5, for injection.

In one embodiment, bendamustine is formulated in a pharmaceutical composition comprising pharmaceutically-acceptable excipients suitable for administration (e.g., intravenous administration), e.g., in accordance with local standard-of-care practice, e.g., as specified by local guidelines or local product labels. In some embodiments, bendamustine is in the form of bendamustine hydrochloride.

In some embodiments, bendamustine (e.g., Treanda®) is provided as a lyophilized powder for reconstitution. In one embodiment, bendamustine is supplied as a single-use vial containing 100 mg of bendamustine HCl as a lyophilized powder. In some embodiments, the lyophilized powder is reconstituted in water. In yet some embodiments, the reconstituted lyophilized powder is formulated in 0.9% sodium chloride or 2.5% dextrose and 0.45% sodium chloride.

In some embodiments, bendamustine is provided as a solution. In one embodiment, bendamustine is supplied at a concentration of 100 mg/4 mL (25 mg/mL) in a multiple dose vial. In some embodiments, bendamustine is formulated in 0.9% sodium chloride. In yet some embodiments, bendamustine is formulated in 2.5% dextrose and 4.5% sodium chloride. In a further embodiment, bendamustine is formulated in 5% dextrose.

In one embodiment, the bispecific antibody used in the methods described herein comprises:

(i) a first binding arm comprising a first antigen-binding region which binds to human CD3ε (epsilon) and comprises a variable heavy chain (VH) region and a variable light chain (VL) region, wherein the VH region comprises the CDR1, CDR2 and CDR3 sequences within the amino acid sequence of SEQ ID NO: 6, and the VL region comprises the CDR1, CDR2 and CDR3 sequences within the amino acid sequence of SEQ ID NO: 7; and (ii) a second binding arm comprising a second antigen-binding region which binds to human CD20 and comprises a VH region and a VL region, wherein the VH region comprises the CDR1, CDR2 and CDR3 sequences within the amino acid sequence of SEQ ID NO: 13, and the VL region comprises the CDR1, CDR2 and CDR3 sequences within the amino acid sequence SEQ ID NO: 14.

CDR1, CDR2 and CDR3 regions can be identified from variable heavy and light chain regions using methods known in the art. The CDR regions from said variable heavy and light chain regions can be annotated according to IMGT (see Lefranc et al., *Nucleic Acids Research* 1999; 27:209-12, 1999] and Brochet. Nucl Acids Res 2008; 36:W503-8).

In some embodiments, the bispecific antibody comprises:

(i) a first binding arm comprising a first antigen-binding region which binds to human CD3ε (epsilon) and comprises VHCDR1, VHCDR2 and VHCDR3 the amino acid sequences set forth in SEQ ID NOs: 1, 2, and 3, respectively, and VLCDR1, VLCDR2, and VLCDR3 comprising the amino acid sequences set forth in SEQ ID NO: 4, the sequence GTN, and SEQ ID NO: 5, respectively; and (ii) a second binding arm comprising a second antigen-binding region which binds to human CD20 and comprises VHCDR1, VHCDR2, and VHCDR3 comprising the amino acid sequences set forth in SEQ ID NOs: 8, 9, and 10, respectively, and VLCDR1, VLCDR2, and VLCDR3 comprising the amino acid sequences set forth in SEQ ID NO: 11, the sequence DAS, and SEQ ID NO: 12, respectively.

In some embodiments, the bispecific antibody comprises:

(i) a first binding arm comprising a first antigen-binding region which binds to human CD3ε (epsilon) and comprises a VH region comprising the amino acid sequence of SEQ ID NO: 6, and a VL region comprising the amino acid sequence of SEQ ID NO: 7; and (ii) a second binding arm comprising a second antigen-binding region which binds to human CD20 and comprises a VH region comprising the amino acid sequence of SEQ ID NO: 13, and a VL region comprising the amino acid sequence of SEQ ID NO: 14.

In one embodiment, the bispecific antibody is a full-length antibody and may have an inert Fc region. In some embodiments, the first binding arm for CD3 is derived from a humanized antibody, e.g., from a full-length IgG1,λ (lambda) antibody such as H1L1 described in WO2015001085, which is incorporated herein by reference, and/or the second binding arm for CD20 is derived from a human antibody, e.g., from a full-length IgG1,κ (kappa) antibody such as clone 7D8 as described in WO2004035607, which is incorporated herein by reference. The bispecific antibody may be produced from two half molecule antibodies. Each of the two half molecule antibodies comprising, e.g., the respective first and second binding arms set forth in SEQ ID NOs: 24 and 25, and SEQ ID NOs: 26 and 27. The half-antibodies may be produced in CHO cells and the bispecific antibodies generated by, e.g., Fab-arm exchange. In one embodiment, the bispecific antibody is a functional variant of DuoBody-CD3xCD20.

Accordingly, in some embodiments, the bispecific antibody comprises (i) a first binding arm comprising a first antigen-binding region which binds to human CD3ε (epsilon) and comprises a VH region comprising an amino acid sequence which is at least 85%, 90%, 95%, 96%, 97%, 98%, or 99% identical to SEQ ID NO: 6 or a VH region comprising the amino acid sequence of SEQ ID NO: 6, but with 1, 2, or 3 mutations (e.g., amino acid substitutions), and a VL region comprising an amino acid sequence which is at least 85%, 90%, 95%, 96%, 97%, 98%, or 99% identical to SEQ ID NO: 7 or a VL region comprising the amino acid sequence of SEQ ID NO: 7, but with 1, 2, or 3 mutations (e.g., amino acid substitutions); and (ii) a second binding arm comprising a second antigen-binding region which binds to human CD20 and comprises a VH region comprising an amino acid sequence which is at least 85%, 90%, 95%, 98%, or 99% identical to SEQ ID NO: 13 or a VH region comprising the amino acid sequence of SEQ ID NO: 13, but with 1, 2, or 3 mutations (e.g., amino acid substitutions), and a VL region comprising an amino acid sequence which is at least 85%, 90%, 95%, 98%, or 99% identical to SEQ ID NO: 14 or a VL region comprising the amino acid sequence of SEQ ID NO: 14, but with 1, 2, or 3 mutations (e.g., amino acid substitutions).

In one embodiment, the bispecific antibody comprises:

(i) a first binding arm comprising a first antigen-binding region which binds to human CD3ε (epsilon) and comprises a heavy chain comprising the amino acid sequence of SEQ ID NO: 24, and a light chain comprising the amino acid sequence of SEQ ID NO: 25; and (ii) a second binding arm comprising a second antigen-binding region which binds to human CD20 and comprises a VH region comprising the amino acid sequence of SEQ ID NO: 26, and a VL region comprising the amino acid sequence of SEQ ID NO: 27.

In some embodiments, the bispecific antibody comprises (i) a first binding arm comprising a first antigen-binding region which binds to human CD3ε (epsilon) and comprises a heavy chain comprising an amino acid sequence which is at least 85%, 90%, 95%, 98%, or 99% identical to SEQ ID NO: 24 or a heavy chain comprising the amino acid sequence of SEQ ID NO: 24, but with 1, 2, or 3 mutations (e.g., amino acid substitutions), and a light chain comprising an amino acid sequence which is at least 85%, 90%, 95%, 98%, or 99% identical to SEQ ID NO: 25 or a light chain region comprising the amino acid sequence of SEQ ID NO: 25, but with 1, 2, or 3 mutations (e.g., amino acid substitutions); and (ii) a second binding arm comprising a second antigen-binding region which binds to human CD20 and comprises a heavy chain comprising an amino acid sequence which is at least 85%, 90%, 95%, 98%, or 99% identical to SEQ ID NO: 26 or a heavy chain comprising the amino acid sequence of SEQ ID NO: 26, but with 1, 2, or 3 mutations (e.g., amino acid substitutions), and a light chain comprising an amino acid sequence which is at least 85%, 90%, 95%, 98%, or 99% identical to SEQ ID NO: 27 or a light chain region comprising the amino acid sequence of SEQ ID NO: 27, but with 1, 2, or 3 mutations (e.g., amino acid substitutions).

Various constant regions or variants thereof may be used in the bispecific antibody. In one embodiment, the antibody comprises an IgG constant region, such as a human IgG1 constant region, e.g., a human IgG1 constant region as defined in SEQ ID NO: 15, or any other suitable IgG1 allotype. In one embodiment, the first binding arm of the bispecific antibody is derived from a humanized antibody, e.g., from a full-length IgG1) (lambda) antibody, and thus comprises a λ light chain constant region. In some embodiments, the first binding arm comprises a λ light chain constant region as defined in SEQ ID NO: 22. In some embodiments, the second binding arm of the bispecific antibody is derived from a human antibody, preferably from a full-length IgG1,κ (kappa) antibody, and thus may comprise a κ light chain constant region. In some embodiments, the second binding arm comprises a κ light chain constant region as defined in SEQ ID NO: 23.

It is understood that the constant region portion of the bispecific antibody may comprise modifications that allow for efficient formation/production of bispecific antibodies and/or provide for an inert Fc region. Such modifications are well known in the art.

Different formats of bispecific antibodies are known in the art (reviewed by Kontermann, *Drug Discov Today* 2015; 20:838-47; MAbs, 2012; 4:182-97). Thus, the bispecific antibody used in the methods and uses described herein are not limited to any particular bispecific format or method of producing it. For example, bispecific antibodies may include, but are not limited to, bispecific antibodies with complementary CH3 domains to force heterodimerization, Knobs-into-Holes molecules (Genentech, WO9850431), CrossMAbs (Roche, WO2011117329), or electrostatically-matched molecules (Amgen, EP1870459 and WO2009089004; Chugai, US201000155133; Oncomed, WO2010129304).

Preferably, the bispecific antibody comprises an Fc-region comprising a first heavy chain with a first Fc sequence comprising a first CH3 region, and a second heavy chain with a second Fc sequence comprising a second CH3 region, wherein the sequences of the first and second CH3 regions are different and are such that the heterodimeric interaction between said first and second CH3 regions is stronger than each of the homodimeric interactions of said first and second CH3 regions. Further details on these interactions and how they can be achieved are provided in e.g. WO2011131746 and WO2013060867 (Genmab), which are hereby incorporated by reference. In one embodiment, the bispecific antibody comprises in the first heavy chain (i) the amino acid L in the position corresponding to F405 in the human IgG1 heavy chain constant region of SEQ ID NO: 15, and comprises in the second heavy chain the amino acid R in the position corresponding to K409 in the human IgG1 heavy chain constant region of SEQ ID NO: 15, or vice versa.

Bispecific antibodies may comprise modifications in the Fc region to render the Fc region inert, or non-activating. Thus, in the bispecific antibodies disclosed herein, one or both heavy chains may be modified so that the antibody induces Fc-mediated effector function to a lesser extent relative to the bispecific antibody which does not have the modification. Fc-mediated effector function may be measured by determining Fc-mediated CD69 expression on T cells (i.e. CD69 expression as a result of CD3 antibody-mediated, Fcγ receptor-dependent CD3 cros slinking), by binding to Fcγ receptors, by binding to C1q, or by induction of Fc-mediated cross-linking of FcγRs. In particular, the heavy chain constant region sequence may be modified so that Fc-mediated CD69 expression is reduced by at least 50%, at least 60%, at least 70%, at least 80%, at least 90%, at least 99% or 100% when compared to a wild-type (unmodified) antibody, wherein said Fc-mediated CD69 expression is determined in a PBMC-based functional assay, e.g. as described in Example 3 of WO2015001085. Modifications of the heavy and light chain constant region sequences may also result in reduced binding of C1q to said antibody. As compared to an unmodified antibody, the reduction may be by at least 70%, at least 80%, at least 90%, at least 95%, at least 97%, or 100%, and C1q binding may be determined, e.g., by ELISA. Further, the Fc region which may be modified so that the antibody mediates reduced Fc-mediated T-cell proliferation compared to an unmodified antibody by at least 50%, at least 60%, at least 70%, at least 80%, at least 90%, at least 99% or 100%, wherein said T-cell proliferation is measured in a PBMC-based functional assay. Examples of amino acid positions that may be modified, e.g., in an IgG1 isotype antibody, include positions L234 and L235. Thus, in one embodiment, the bispecific antibody may comprise a first heavy chain and a second heavy chain, and wherein in both the first heavy chain and the second heavy chain, the amino acid residues at the positions corresponding to positions L234 and L235 in a human IgG1 heavy chain according to Eu numbering are F and E, respectively. In addition, a D265A amino acid substitution can decrease binding to all Fcγ receptors and prevent ADCC (Shields et al., *JBC* 2001; 276:6591-604). Therefore, the bispecific antibody may comprise a first heavy chain and a second heavy chain, wherein in both the first heavy chain and the second heavy chain, the amino acid residue at the position corresponding to position D265 in a human IgG1 heavy chain according to Eu numbering is A.

In one embodiment, in the first heavy chain and second heavy chain of the bispecific antibody, the amino acids in the positions corresponding to positions L234, L235, and D265 in a human IgG1 heavy chain, are F, E, and A, respectively. An antibody having these amino acids at these positions is an example of an antibody having an inert Fc region, or a non-activating Fc region.

With regard to the bispecific antibodies described herein, those which have the combination of three amino acid substitutions L234F, L235E and D265A and in addition the K409R or the F405L mutation, as described above, may be referred to with the suffix "FEAR" or "FEAL", respectively.

An amino acid sequence of a wild type IgG1 heavy chain constant region may be identified herein as SEQ ID NO: 15. Consistent with the embodiments disclosed above, the bispecific antibody may comprise an IgG1 heavy chain constant region carrying the F405L substitution and may have the amino acid sequence set forth in SEQ ID NO: 17 and/or an IgG1 heavy chain constant region carrying the K409R substitution and may have the amino acid sequence set forth in SEQ ID NO: 18, and have further substitutions that render the Fc region inert or non-activating. Hence, in one embodiment, the bispecific antibody comprises a combination of IgG1 heavy chain constant regions, with the amino acid sequence of one of the IgG1 heavy chain constant regions carrying the L234F, L235E, D265A and F405L substitutions (e.g., as set forth in SEQ ID NO: 19) and the amino acid sequence of the other IgG1 heavy chain constant region carrying the L234F, L235E, D265A and K409R substitutions (e.g., as set forth in SEQ ID NO: 20).

In some embodiments, the bispecific antibody used in the methods and uses described herein comprises a first binding arm comprising a heavy chain and a light chain as defined in SEQ ID NOs: 24 and 25, respectively, and a second binding arm comprising a heavy chain and a light chain as defined in SEQ ID NOs: 26 and 27, respectively. Such an antibody is referred to herein as DuoBody CD3xCD20. Also, variants of such antibodies are contemplated use in the methods and uses as described herein. In some embodiments, the bispecific antibody is epcoritamab (CAS 2134641-34-0), or a biosimilar thereof.

Kits

Also provided herein are kits which include a pharmaceutical composition containing a bispecific antibody which binds to CD3 and CD20 in accordance with the invention, such as DuoBody CD3xCD20 or epcoritamab, and a pharmaceutically-acceptable carrier, in a therapeutically effective amount adapted for use in the methods described herein. The kits may also include a pharmaceutical composition containing rituximab (e.g., for intravenous administration) and/or bendamustine (e.g., for intravenous administration in solution or lyophilized powder form). The kits optionally also can include instructions, e.g., comprising administration schedules, to allow a practitioner (e.g., a physician, nurse, or patient) to administer the composition or compositions contained therein to a patient with follicular lymphoma. The kit also can include a syringe or syringes.

Optionally, the kits include multiple packages of the single-dose pharmaceutical compositions each containing an effective amount of the bispecific antibody for a single administration in accordance with the methods described herein. They may also include multiple packages of single dose pharmaceutical compositions containing a dose of rituximab and/or bendamustine in accordance with a standard of care regimen. Instruments or devices necessary for administering the pharmaceutical composition(s) also may be included in the kits.

FURTHER EMBODIMENTS

1. A bispecific antibody comprising
   (i) a first binding arm comprising a first antigen-binding region which binds to human CD3ε (epsilon) and comprises a variable heavy chain (VH) region and a variable light chain (VL) region, wherein the VH region comprises the CDR1, CDR2 and CDR3 sequences that are in the
   VH region sequence of SEQ ID NO: 6, and the VL region comprises the CDR1, CDR2 and CDR3 sequences that are in the VL region sequence of SEQ ID NO: 7; and
   (ii) a second binding arm comprising a second antigen-binding region which binds to human CD20 and comprises a VH region and a VL region, wherein the VH region comprises the CDR1, CDR2 and CDR3 sequences that are in the VH region sequence of SEQ ID NO: 13, and the VL region comprises the CDR1, CDR2 and CDR3 sequences that are in the VL region sequence of SEQ ID NO: 14;
   for use in the treatment of follicular lymphoma in a human subject, wherein the treatment comprises administering the bispecific antibody and an effective amount of rituximab and bendamustine to the human subject, wherein the bispecific antibody is administered at a dose of 24 mg or 48 mg, and wherein the bispecific antibody, rituximab, and bendamustine are administered in 28-day cycles.
2. The bispecific antibody of embodiment 1, wherein the bispecific antibody is administered at a dose of 24 mg.
3. The bispecific antibody of embodiment 1, wherein the bispecific antibody is administered at a dose of 48 mg.
4. The bispecific antibody of any one of embodiments 1-3, wherein the bispecific antibody is administered once every week (weekly administration).
5. The bispecific antibody of embodiment 4, wherein the weekly administration of 24 mg or 48 mg is performed for 2.5 28-day cycles.
6. The bispecific antibody of embodiment 4 or 5, wherein after the weekly administration, the bispecific antibody is administered once every two weeks (biweekly administration).
7. The bispecific antibody of embodiment 6, wherein the biweekly administration is performed for six 28-day cycles.
8. The bispecific antibody of embodiment 6 or 7, wherein after the biweekly administration, the bispecific antibody is administered once every four weeks.
9. The bispecific antibody of embodiment 8, wherein the administration once every four weeks is performed for up to two years total duration of treatment with the bispecific antibody from initiation of rituximab and bendamustine.
10. The bispecific antibody of any one of embodiments 4-9, wherein prior to the weekly administration of 24 mg or 48 mg, a priming dose of the bispecific antibody is administered in cycle 1 of the 28-day cycles.
11. The bispecific antibody of embodiment 10, wherein the priming dose is administered two weeks prior to administering the first weekly dose of 24 mg or 48 mg.
12. The bispecific antibody of embodiment 10 or 11, wherein the priming dose is 0.16 mg.
13. The bispecific antibody of any one of embodiments 10-12, wherein after administering the priming dose and prior to administering the first weekly dose of 24 mg or 48 mg, an intermediate dose of the bispecific antibody is administered.
14. The bispecific antibody of embodiment 13, wherein the priming dose is administered on day 1 and the intermediate dose is administered on day 8 before the first weekly dose of 24 mg or 48 mg on days 15 and 22 of cycle 1.
15. The bispecific antibody of embodiment 13 or 14, wherein the intermediate dose is 0.8 mg.
16. The bispecific antibody of any one of embodiments 1-15, wherein rituximab is administered once every four weeks.
17. The bispecific antibody of embodiment 16, wherein the administration of rituximab once every four weeks is performed for six 28-day cycles.
18. The bispecific antibody of any one of embodiments 1-17, wherein rituximab is administered at a dose of 375 mg/m$^2$.
19. The bispecific antibody of any one of embodiments 1-18, wherein bendamustine is administered once a day from day 1 to day 2 of the 28-day cycles.
20. The bispecific antibody of any one of embodiments 1-19, wherein bendamustine is administered once a day from day 1 to day 2 for six 28-day cycles.
21. The bispecific antibody of any one of embodiments 1-20, wherein bendamustine is administered at a dose of 90 mg/m$^2$.
22. The bispecific antibody of embodiments 1-21, wherein rituximab, bendamustine, and the bispecific antibody are administered on the same day (e.g., on days 1 of cycles 1-6).
23. The bispecific antibody of any one of embodiments 1-22, wherein the dosing schedule for the bispecific antibody, rituximab, and bendamustine is as shown in Table 2.
24. The bispecific antibody of any one of embodiments 1, 2, and 4-23, wherein administration is performed in 28-day cycles, and wherein:
    (a) the bispecific antibody is administered as follows:
       (i) in cycle 1, a priming dose of 0.16 mg is administered on day 1, an intermediate dose of 0.8 mg is administered on day 8, and a dose of 24 mg is administered on days 15 and 22;
       (ii) in cycles 2 and 3, a dose of 24 mg is administered on days 1, 8, 15, and 22;
       (iii) in cycles 4-9, a dose of 24 mg is administered on days 1 and 15; and
       (iv) in cycle 10 and subsequent cycles, a dose of 24 mg is administered on day 1;
    (b) rituximab is administered on day 1 in cycles 1-6; and
    (c) bendamustine is administered on days 1 and 2 in cycles 1-6.

25. The bispecific antibody of any one of embodiments 1 and 3-24, wherein administration is performed in 28-day cycles, and wherein:
    (a) the bispecific antibody is administered as follows:
        (i) in cycle 1, a priming dose of 0.16 mg is administered on day 1, an intermediate dose of 0.8 mg is administered on day 8, and a dose of 48 mg is administered on days 15 and 22;
        (ii) in cycles 2 and 3, a dose of 48 mg is administered on days 1, 8, 15, and 22;
        (iii) in cycles 4-9, a dose of 48 mg is administered on days 1 and 15; and
        (iv) in cycle 10 and subsequent cycles, a dose of 48 mg is administered on day 1;
    (b) rituximab is administered on day 1 in cycles 1-6; and
    (c) bendamustine is administered on days 1 and 2 in cycles 1-6.
26. The bispecific antibody of any one of embodiments 1-25, wherein the bispecific antibody is administered subcutaneously.
27. The bispecific antibody of any one of embodiments 1-26, wherein rituximab is administered intravenously.
28. The bispecific antibody of any one of embodiments 1-27, wherein bendamustine is administered intravenously.
29. The bispecific antibody of any one of embodiments 1-28, wherein the bispecific antibody, rituximab, and bendamustine are administered sequentially.
30. The bispecific antibody of any one of embodiments 1-29, wherein:
    (a) rituximab is administered before the bispecific antibody if rituximab and the bispecific antibody are administered on the same day (e.g., day 1 of cycles 1-6);
    (b) bendamustine is administered before the bispecific antibody if bendamustine and the bispecific antibody are administered on the same day (e.g., day 1 of cycles 1-6);
    (c) rituximab is administered before bendamustine if rituximab and bendamustine are administered on the same day (e.g., day 1 of cycles 1-6); or
    (d) rituximab is administered first, bendamustine is administered second, and the bispecific antibody is administered last if rituximab, bendamustine, and the bispecific antibody are administered on the same day (e.g., day 1 of cycles 1-6).
31. The bispecific antibody of any one of embodiments 1-30, wherein the follicular lymphoma is previously untreated follicular lymphoma.
32. The bispecific antibody of embodiment 31, wherein the subject has grade 1, 2, or 3a untreated follicular lymphoma.
33. The bispecific antibody of embodiment 31 or 32, wherein the subject has Stage II, III, or IV untreated follicular lymphoma.
34. The bispecific antibody of any one of embodiments 1-33, wherein the subject is treated with prophylaxis for cytokine release syndrome.
35. The bispecific antibody of embodiment 34, wherein the prophylaxis comprises administering a corticosteroid to the subject.
36. The bispecific antibody of embodiment 35, wherein the corticosteroid is administered on the same day as the bispecific antibody.
37. The bispecific antibody of embodiment 36, wherein the corticosteroid is further administered on the second, third, and fourth days after administering the bispecific antibody.
38. The bispecific antibody of any one of embodiments 35-37, wherein the corticosteroid is prednisolone.
39. The bispecific antibody of embodiment 38, wherein the prednisolone is administered at an intravenous dose of 100 mg, or equivalent thereof, including oral dose.
40. The bispecific antibody of any one of embodiments 1-39, wherein the subject is administered premedication to reduce reactions to injections.
41. The bispecific antibody of embodiment 40, wherein the premedication comprises an antihistamine.
42. The bispecific antibody of embodiment 41, wherein the antihistamine is diphenhydramine.
43. The bispecific antibody of embodiment 42, wherein the diphenhydramine is administered at an intravenous or oral dose of 50 mg, or equivalent thereof.
44. The bispecific antibody of any one of embodiments 40-43, wherein the premedication comprises an antipyretic.
45. The bispecific antibody of embodiment 44, wherein the antipyretic is acetaminophen.
46. The bispecific antibody of embodiment 45, wherein the acetaminophen is administered at an oral dose of 650 mg to 1000 mg, or equivalent thereof.
47. The bispecific antibody of any one of embodiments 40-46, wherein the premedication is administered on the same day as the bispecific antibody.
48. The bispecific antibody of any one of embodiments 34-47, wherein the prophylaxis is administered in cycle 1 of the 28-day cycles.
49. The bispecific antibody of any one of embodiments 40-48, wherein the premedication is administered in cycle 1 of the 28-day cycles.
50. The bispecific antibody of any one of embodiments 34-49, wherein the prophylaxis is administered during cycle 2 of the 28-day cycles when the subject experiences CRS greater than grade 1 after the last administration of the bispecific antibody in cycle 1 of the 28-day cycles.
51. The bispecific antibody of embodiment 50, wherein the prophylaxis is continued in a subsequent cycle, when in the last administration of the bispecific antibody of the previous cycle, the subject experiences CRS greater than grade 1.
52. The bispecific antibody of any one of embodiments 40-51, wherein the premedication is administered during cycle 2 of the 28-day cycles.
53. The bispecific antibody of embodiment 52, wherein the premedication is administered during subsequent cycles.
54. The bispecific antibody of any one of embodiments 1-53, wherein the subject is administered antibiotics if the subject develops Grade 1 CRS.
55. The bispecific antibody of any one of embodiments 1-53, wherein the subject is administered a vasopressor if the subject develops Grade 2 or Grade 3 CRS.
56. The bispecific antibody of any one of embodiments 1-53, wherein the subject is administered at least two vasopressors if the subject develops Grade 4 CRS.
57. The bispecific antibody of any one of embodiments 1-56, wherein the subject is administered tocilizumab if the subject develops Grade 2, Grade 3, or Grade 4 CRS.
58. The bispecific antibody of embodiment 57, wherein the subject is further administered a steroid.
59. The bispecific antibody of embodiment 58, wherein the steroid is dexamethasone.
60. The bispecific antibody of embodiment 58, wherein the steroid is methylprednisolone.

61. The bispecific antibody of any one of embodiments 57-60, wherein tocilizumab is switched to an anti-IL-6 antibody (e.g., siltuximab) if the subject is refractory to tocilizumab.
62. The bispecific antibody of any one of embodiments 57-60, wherein tocilizumab is switched to an IL-1R antagonist (e.g., anakinra) if the subject is refractory to tocilizumab.
63. The bispecific antibody of any one of embodiments 1-62, wherein the subject is treated with prophylaxis for tumor lysis syndrome (TLS).
64. The bispecific antibody of embodiment 63, wherein the prophylaxis for TLS comprises administering one or more uric acid reducing agents prior to administration of the bispecific antibody.
65. The bispecific antibody of embodiment 64, wherein the one or more uric acid reducing agents comprise rasburicase and/or allopurinol.
66. The bispecific antibody of any one of embodiments 1-65, wherein the subject achieves a complete response, a partial response, or stable disease.
67. The bispecific antibody of any one of embodiments 1-66, wherein:
    (i) the first antigen-binding region of the bispecific antibody comprises VHCDR1, VHCDR2, and VHCDR3 comprising the amino acid sequences set forth in SEQ ID NOs: 1, 2, and 3, respectively, and VLCDR1, VLCDR2, and VLCDR3 comprising the amino acid sequences set forth in SEQ ID NO: 4, the sequence GTN, and SEQ ID NO: 5, respectively; and
    (ii) the second antigen-binding region of the bispecific antibody comprises VHCDR1, VHCDR2, and VHCDR3 comprising the amino acid sequences set forth in SEQ ID NOs: 8, 9, and 10, respectively, and VLCDR1, VLCDR2, and VLCDR3 comprising the amino acid sequences set forth in SEQ ID NO: 11, the sequence DAS, and SEQ ID NO: 12, respectively.
68. The bispecific antibody of any one of embodiments 1-67, wherein:
    (i) the first antigen-binding region of the bispecific antibody comprises a VH region comprising the amino acid sequence of SEQ ID NO: 6, and the VL region comprising the amino acid sequence of SEQ ID NO: 7; and
    (ii) the second antigen-binding region of the bispecific antibody comprises a VH region comprising the amino acid sequence of SEQ ID NO: 13, and the VL region comprising the amino acid sequence of SEQ ID NO: 14.
69. The bispecific antibody of any one of embodiments 1-68, wherein the first binding arm of the bispecific antibody is derived from a humanized antibody, preferably from a full-length IgG 1) (lambda) antibody.
70. The bispecific antibody of embodiment 69, wherein the first binding arm of the bispecific antibody comprises a λ light chain constant region comprising the amino acid sequence set forth in SEQ ID NO: 22.
71. The bispecific antibody of any one of embodiments 1-70, wherein the second binding arm of the bispecific antibody is derived from a human antibody, preferably from a full-length IgG1,κ (kappa) antibody.
72. The bispecific antibody of embodiment 71, wherein the second binding arm comprises a κ light chain constant region comprising the amino acid sequence set forth in SEQ ID NO: 23.
73. The bispecific antibody of any one of embodiments 1-72, wherein the bispecific antibody is a full-length antibody with a human IgG1 constant region.
74. The bispecific antibody of any one of embodiments 1-73, wherein the bispecific antibody comprises an inert Fc region.
75. The bispecific antibody of any one of embodiments 1-74, wherein the bispecific antibody comprises a first heavy chain and a second heavy chain, wherein in both the first and second heavy chains, the amino acids in the positions corresponding to positions L234, L235, and D265 in the human IgG1 heavy chain constant region of SEQ ID NO: 15 are F, E, and A, respectively.
76. The bispecific antibody of any one of embodiments 1-75, wherein the bispecific antibody comprises a first heavy chain and a second heavy chain, wherein in the first heavy chain, the amino acid in the position corresponding to F405 in the human IgG1 heavy chain constant region of SEQ ID NO: 15 is L, and wherein in the second heavy chain, the amino acid in the position corresponding to K409 in the human IgG1 heavy chain constant region of SEQ ID NO: 15 is R, or vice versa.
77. The bispecific antibody of any one of embodiments 1-76, wherein the bispecific antibody comprises a first heavy chain and a second heavy chain, wherein
    (i) in both the first and second heavy chains, the amino acids in the positions corresponding to positions L234, L235, and D265 in the human IgG1 heavy chain constant region of SEQ ID NO: 15 are F, E, and A, respectively, and
    (ii) in the first heavy chain, the amino acid in the position corresponding to F405 in the human IgG1 heavy chain constant region of SEQ ID NO: 15 is L, and wherein in the second heavy chain, the amino acid in the position corresponding to K409 in the human IgG1 heavy chain constant region of SEQ ID NO: 15 is R, or vice versa.
78. The bispecific antibody of embodiment 77, wherein the bispecific antibody comprises heavy chain constant regions comprising the amino acid sequences of SEQ ID NOs: 19 and 20.
79. The bispecific antibody of any one of embodiments 1-78, wherein the bispecific antibody comprises a heavy chain and a light chain comprising the amino acid sequences set forth in SEQ ID NOs: 24 and 25, respectively, and a heavy chain and a light chain comprising the amino acid sequences set forth in SEQ ID NOs: 26 and 27, respectively.
80. The bispecific antibody of any one of embodiments 1-79, wherein the bispecific antibody comprises a heavy chain and a light chain consisting of the amino acid sequence of SEQ ID NOs: 24 and 25, respectively, and a heavy chain and a light chain consisting of the amino acid sequence of SEQ ID NOs: 26 and 27, respectively.
81. The bispecific antibody of any one of embodiments 1-80, wherein the bispecific antibody is epcoritamab, or a biosimilar thereof.
1a. A method of treating follicular lymphoma in a human subject, the method comprising administering to the subject a bispecific antibody and an effective amount of rituximab and bendamustine, wherein the bispecific antibody comprises:
    (i) a first binding arm comprising a first antigen-binding region which binds to human CD3ε (epsilon) and comprises a variable heavy chain (VH) region and a variable light chain (VL) region, wherein the VH region comprises the CDR1, CDR2 and CDR3 sequences that are in the VH region sequence of SEQ ID NO: 6, and the VL region comprises the CDR1, CDR2 and CDR3 sequences that are in the VL region sequence of SEQ ID NO: 7; and (ii) a second binding arm comprising a second antigen-binding region which binds to human CD20 and comprises a VH region and a VL region, wherein the VH region comprises the CDR1, CDR2 and CDR3 sequences that are in the VH region sequence of SEQ ID NO: 13, and the VL region comprises the CDR1, CDR2 and CDR3 sequences that are in the VL region sequence of SEQ ID NO: 14;
wherein the bispecific antibody is administered at a dose of 24 mg or 48 mg, and wherein rituximab, bendamustine, and the bispecific antibody are administered in 28-day cycles.

2a. The method of embodiment 1a, wherein the bispecific antibody is administered at a dose of 24 mg.

3aa. The method of embodiment 1a, wherein the bispecific antibody is administered at a dose of 48 mg.

4a. The method of any one of embodiments 1a-3a, wherein the bispecific antibody is administered once every week (weekly administration).

5a. The method of embodiment 4a, wherein the weekly administration of 24 mg or 48 mg is performed for 2.5 28-day cycles.

6a. The method of embodiment 4a or 5a, wherein after the weekly administration, the bispecific antibody is administered once every two weeks (biweekly administration).

7a. The method of embodiment 6a, wherein the biweekly administration is performed for six 28-day cycles.

8a. The method of embodiment 6a or 7a, wherein after the biweekly administration, the bispecific antibody is administered once every four weeks.

9a. The method of embodiment 8a, wherein the administration once every four weeks is performed for up to two years total duration of treatment with the bispecific antibody from initiation of rituximab and bendamustine.

10a. The method of any one of embodiments 4a-9a, wherein prior to the weekly administration of 24 mg or 48 mg, a priming dose of the bispecific antibody is administered in cycle 1 of the 28-day cycles.

11a. The method of embodiment 10a, wherein the priming dose is administered two weeks prior to administering the first weekly dose of 24 mg or 48 mg.

12a. The method of embodiment 10a or 11a, wherein the priming dose is 0.16 mg.

13a. The method of any one of embodiments 10a-12a, wherein after administering the priming dose and prior to administering the first weekly dose of 24 mg or 48 mg, an intermediate dose of the bispecific antibody is administered.

14a. The method of embodiment 13a, wherein the priming dose is administered on day 1 and the intermediate dose is administered on day 8 before the first weekly dose of 24 mg or 48 mg on days 15 and 22 of cycle 1.

15a. The method of embodiment 13a or 14a, wherein the intermediate dose is 0.8 mg.

16a. The method of any one of embodiments 1a-15a, wherein rituximab is administered once every four weeks.

17a. The method of embodiment 16a, wherein the administration of rituximab once every four weeks is performed for six 28-day cycles.

18a. The method of any one of embodiments 1a-17a, wherein rituximab is administered at a dose of 375 mg/m².

19a. The method of any one of embodiments 1a-18a, wherein bendamustine is administered once a day from day 1 to day 2 of the 28-day cycles.

20a. The method of any one of embodiments 1a-19a, wherein bendamustine is administered once a day from day 1 to day 2 for six 28-day cycles.

21a. The method of any one of embodiments 1a-20a, wherein bendamustine is administered at a dose of 90 mg/m².

22a. The method of any one of embodiments 1a-21a, wherein rituximab, bendamustine, and the bispecific antibody are administered on the same day (e.g., on days 1 of cycles 1-6).

23a. The method of any one of embodiments 1a-22a, wherein the dosing schedule for the bispecific antibody, rituximab, and bendamustine is as shown in Table 2.

24a. The method of any one of embodiments 1a, 2a, and 4a-23a, wherein administration is performed in 28-day cycles, and wherein:
(a) the bispecific antibody is administered as follows:
  (i) in cycle 1, a priming dose of 0.16 mg is administered on day 1, an intermediate dose of 0.8 mg is administered on day 8, and a dose of 24 mg is administered on days 15 and 22;
  (ii) in cycles 2 and 3, a dose of 24 mg is administered on days 1, 8, 15, and 22;
  (iii) in cycles 4-9, a dose of 24 mg is administered on days 1 and 15; and
  (iv) in cycle 10 and subsequent cycles, a dose of 24 mg is administered on day 1;
(b) rituximab is administered on day 1 in cycles 1-6; and
(c) bendamustine is administered on days 1 and 2 in cycles 1-6.

25a. The method of any one of embodiments 1 and 3a-24a, wherein administration is performed in 28-day cycles, and wherein:
(a) the bispecific antibody is administered as follows:
  (i) in cycle 1, a priming dose of 0.16 mg is administered on day 1, an intermediate dose of 0.8 mg is administered on day 8, and a dose of 48 mg is administered on days 15 and 22;
  (ii) in cycles 2 and 3, a dose of 48 mg is administered on days 1, 8, 15, and 22;
  (iii) in cycles 4-9, a dose of 48 mg is administered on days 1 and 15; and
  (iv) in cycle 10 and subsequent cycles, a dose of 48 mg is administered on day 1;
(b) rituximab is administered on day 1 in cycles 1-6; and
(c) bendamustine is administered on days 1 and 2 in cycles 1-6.

26a. The method of any one of embodiments 1a-25a, wherein the bispecific antibody is administered subcutaneously.

27a. The method of any one of embodiments 1a-26a, wherein rituximab is administered intravenously.

28a. The method of any one of embodiments 1a-27a, wherein bendamustine is administered intravenously.

29a. The method of any one of embodiments 1a-28a, wherein the bispecific antibody, rituximab, and bendamustine are administered sequentially.

30a. The method of any one of embodiments 1a-29a, wherein:
(a) rituximab is administered before the bispecific antibody if rituximab and the bispecific antibody are administered on the same day (e.g., day 1 of cycles 1-6);
(b) bendamustine is administered before the bispecific antibody if bendamustine and the bispecific antibody are administered on the same day (e.g., day 1 of cycles 1-6);

(c) rituximab is administered before bendamustine if rituximab and bendamustine are administered on the same day (e.g., day 1 of cycles 1-6); or (d) rituximab is administered first, bendamustine is administered second, and the bispecific antibody is administered last if rituximab, bendamustine, and the bispecific antibody are administered on the same day (e.g., day 1 of cycles 1-6).

31a. The method of any one of embodiments 1a-30a, wherein the follicular lymphoma is previously untreated follicular lymphoma.

32a. The method of embodiment 31a, wherein the subject has grade 1, 2, or 3a untreated follicular lymphoma.

33a. The method of embodiment 31a or 32a, wherein the subject has Stage II, III, or IV untreated follicular lymphoma.

34a. The method of any one of embodiments 1a-33a, wherein the subject is treated with prophylaxis for cytokine release syndrome.

35a. The method of embodiment 34a, wherein the prophylaxis comprises administering a corticosteroid to the subject.

36a. The method of embodiment 35a, wherein the corticosteroid is administered on the same day as the bispecific antibody.

37a. The method of embodiment 36a, wherein the corticosteroid is further administered on the second, third, and fourth days after administering the bispecific antibody.

38a. The method of any one of embodiments 35a-37a, wherein the corticosteroid is prednisolone.

39a. The method of embodiment 38a, wherein the prednisolone is administered at an intravenous dose of 100 mg, or equivalent thereof, including oral dose.

40a. The method of any one of embodiments 1a-39a, wherein the subject is administered premedication to reduce reactions to injections.

41a. The method of embodiment 40a, wherein the premedication comprises an antihistamine.

42a. The method of embodiment 41a, wherein the antihistamine is diphenhydramine.

43a. The method of embodiment 42a, wherein the diphenhydramine is administered at an intravenous or oral dose of 50 mg, or equivalent thereof.

44a. The method of any one of embodiments 40a-43a, wherein the premedication comprises an antipyretic.

45a. The method of embodiment 44a, wherein the antipyretic is acetaminophen.

46a. The method of embodiment 45a, wherein the acetaminophen is administered at an oral dose of 650 mg to 1000 mg, or equivalent thereof.

47a. The method of any one of embodiments 40a-46a, wherein the premedication is administered on the same day as the bispecific antibody.

48a. The method of any one of embodiments 34a-47a, wherein the prophylaxis is administered in cycle 1 of the 28-day cycles.

49a. The method of any one of embodiments 40a-48a, wherein the premedication is administered in cycle 1 of the 28-day cycles.

50a. The method of any one of embodiments 34a-49a, wherein the prophylaxis is administered during cycle 2 of the 28-day cycles when the subject experiences CRS greater than grade 1 after the last administration of the bispecific antibody in cycle 1 of the 28-day cycles.

51a. The method of embodiment 50a, wherein the prophylaxis is continued in a subsequent cycle, when in the last administration of the bispecific antibody of the previous cycle, the subject experiences CRS greater than grade 1.

52a. The method of any one of embodiments 40a-51a, wherein the premedication is administered during cycle 2 of the 28-day cycles.

53a. The method of embodiment 52a, wherein the premedication is administered during subsequent cycles.

54a. The method of any one of embodiments 1a-53a, wherein the subject is administered antibiotics if the subject develops Grade 1 CRS.

55a. The method of any one of embodiments 1a-53a, wherein the subject is administered a vasopressor if the subject develops Grade 2 or Grade 3 CRS.

56a. The method of any one of embodiments 1a-53a, wherein the subject is administered at least two vasopressors if the subject develops Grade 4 CRS.

57a. The method of any one of embodiments 1a-56a, wherein the subject is administered tocilizumab if the subject develops Grade 2, Grade 3, or Grade 4 CRS.

58a. The method of embodiment 57a, wherein the subject is further administered a steroid.

59a. The method of embodiment 58a, wherein the steroid is dexamethasone.

60a. The method of embodiment 58a, wherein the steroid is methylprednisolone.

61a. The method of any one of embodiments 57a-60a, wherein tocilizumab is switched to an anti-IL-6 antibody (e.g., siltuximab) if the subject is refractory to tocilizumab.

62a. The method of any one of embodiments 57a-60a, wherein tocilizumab is switched to an IL-1R antagonist (e.g., anakinra) if the subject is refractory to tocilizumab.

63a. The method of any one of embodiments 1a-62a, wherein the subject is treated with prophylaxis for tumor lysis syndrome (TLS).

64a. The method of embodiment 63a, wherein the prophylaxis for TLS comprises administering one or more uric acid reducing agents prior to administration of the bispecific antibody.

65a. The method of embodiment 64a, wherein the one or more uric acid reducing agents comprise rasburicase and/or allopurinol.

66a. The method of any one of embodiments 1a-65a, wherein the subject achieves a complete response, a partial response, or stable disease.

67a. The method of any one of embodiments 1a-66a, wherein:

(i) the first antigen-binding region of the bispecific antibody comprises VHCDR1, VHCDR2, and VHCDR3 comprising the amino acid sequences set forth in SEQ ID NOs: 1, 2, and 3, respectively, and VLCDR1, VLCDR2, and VLCDR3 comprising the amino acid sequences set forth in SEQ ID NO: 4, the sequence GTN, and SEQ ID NO: 5, respectively; and (ii) the second antigen-binding region of the bispecific antibody comprises VHCDR1, VHCDR2, and VHCDR3 comprising the amino acid sequences set forth in SEQ ID NOs: 8, 9, and 10, respectively, and VLCDR1, VLCDR2, and VLCDR3 comprising the amino acid sequences set forth in SEQ ID NO: 11, the sequence DAS, and SEQ ID NO: 12, respectively.

68a. The method of any one of embodiments 1a-67a, wherein:

(i) the first antigen-binding region of the bispecific antibody comprises a VH region comprising the amino acid sequence of SEQ ID NO: 6, and the VL region comprising the amino acid sequence of SEQ ID NO: 7; and (ii) the second antigen-binding region of the bispecific antibody comprises a VH region comprising the amino acid sequence of SEQ ID NO: 13, and the VL region comprising the amino acid sequence of SEQ ID NO: 14.

69a. The method of any one of embodiments 1a-68a, wherein the first binding arm of the bispecific antibody is derived from a humanized antibody, preferably from a full-length IgG1,λ (lambda) antibody.

70a. The method of embodiment 69a, wherein the first binding arm of the bispecific antibody comprises a λ light chain constant region comprising the amino acid sequence set forth in SEQ ID NO: 22.

71a. The method of any one of embodiments 1a-70a, wherein the second binding arm of the bispecific antibody is derived from a human antibody, preferably from a full-length IgG1,κ (kappa) antibody.

72a. The method of embodiment 71a, wherein the second binding arm comprises a κ light chain constant region comprising the amino acid sequence set forth in SEQ ID NO: 23.

73a. The method of any one of embodiments 1a-72a, wherein the bispecific antibody is a full-length antibody with a human IgG1 constant region.

74a. The method of any one of embodiments 1a-73a, wherein the bispecific antibody comprises an inert Fc region.

75a. The method of any one of embodiments 1a-74a, wherein the bispecific antibody comprises a first heavy chain and a second heavy chain, wherein in both the first and second heavy chains, the amino acids in the positions corresponding to positions L234, L235, and D265 in the human IgG1 heavy chain constant region of SEQ ID NO: 15 are F, E, and A, respectively.

76a. The method of any one of embodiments 1a-75a, wherein the bispecific antibody comprises a first heavy chain and a second heavy chain, wherein in the first heavy chain, the amino acid in the position corresponding to F405 in the human IgG1 heavy chain constant region of SEQ ID NO: 15 is L, and wherein in the second heavy chain, the amino acid in the position corresponding to K409 in the human IgG1 heavy chain constant region of SEQ ID NO: 15 is R, or vice versa.

77a. The method of any one of embodiments 1a-76a, wherein the bispecific antibody comprises a first heavy chain and a second heavy chain, wherein (i) in both the first and second heavy chains, the amino acids in the positions corresponding to positions L234, L235, and D265 in the human IgG1 heavy chain constant region of SEQ ID NO: 15 are F, E, and A, respectively, and (ii) in the first heavy chain, the amino acid in the position corresponding to F405 in the human IgG1 heavy chain constant region of SEQ ID NO: 15 is L, and wherein in the second heavy chain, the amino acid in the position corresponding to K409 in the human IgG1 heavy chain constant region of SEQ ID NO: 15 is R, or vice versa.

78a. The method of embodiment 77a, wherein the bispecific antibody comprises heavy chain constant regions comprising the amino acid sequences of SEQ ID NOs: 19 and 20.

79a. The method of any one of embodiments 1a-78a, wherein the bispecific antibody comprises a heavy chain and a light chain comprising the amino acid sequences set forth in SEQ ID NOs: 24 and 25, respectively, and a heavy chain and a light chain comprising the amino acid sequences set forth in SEQ ID NOs: 26 and 27, respectively.

80a. The method of any one of embodiments 1a-79a, wherein the bispecific antibody comprises a heavy chain and a light chain consisting of the amino acid sequence of SEQ ID NOs: 24 and 25, respectively, and a heavy chain and a light chain consisting of the amino acid sequence of SEQ ID NOs: 26 and 27, respectively.

81a. The method of any one of embodiments 1a-80a, wherein the bispecific antibody is epcoritamab, or a biosimilar thereof.

The present disclosure is further illustrated by the following examples, which should not be construed as further limiting. The contents of all figures and all references, Genbank sequences, journal publications, patents, and published patent applications cited throughout this application are expressly incorporated herein by reference.

EXAMPLES

DuoBody-CD3xCD20

DuoBody-CD3xCD20 is a bsAb recognizing the T-cell antigen CD3 and the B-cell antigen CD20. DuoBody-CD3xCD20 triggers potent T-cell-mediated killing of CD20-expressing cells. DuoBody-CD3xCD20 has a regular IgG1 structure.

Two parental antibodies, IgG1-CD3-FEAL, a humanized IgG1λ, CD3ε-specific antibody having heavy and light chain sequences as listed in SEQ ID NOs: 24 and 25, respectively, and IgG1-CD20-FEAR, derived from human IgG1κ CD20-specific antibody 7D8 having heavy and light chain sequences as listed in SEQ ID NOs: 26 and 27, respectively, were manufactured as separate biological intermediates. Each parental antibody contains one of the complementary mutations in the CH3 domain required for the generation of DuoBody molecules (F405L and K409R, respectively). The parental antibodies comprised three additional mutations in the Fc region (L234F, L235E and D265A; FEA). The parental antibodies were produced in mammalian Chinese hamster ovary (CHO) cell lines using standard suspension cell cultivation and purification technologies. DuoBody-CD3xCD20 was subsequently manufactured by a controlled Fab-arm exchange (cFAE) process (Labrijn et al. 2013, Labrijn et al. 2014, Gramer et al. 2013). The parental antibodies are mixed and subjected to controlled reducing conditions. This leads to separation of the parental antibodies that, under re-oxidation, re-assemble. This way, highly pure preparations of DuoBody-CD3xCD20 (~93-95%) were obtained. After further polishing/purification, final product was obtained, close to 100% pure. The DuoBody-CD3xCD20 concentration was measured by absorbance at 280 nm, using the theoretical extinction coefficient $\varepsilon=1.597$ mL·mg$^{-1}$ cm$^{-1}$. The final product was stored at 4° C. The product has an international proprietary name of epcoritamab.

Epcoritamab is prepared (5 mg/mL or 60 mg/mL) as a sterile clear colorless to slightly yellow solution supplied as concentrate for solution for subcutaneous (SC) injection. Epcoritamab contains buffering and tonicifying agents. All excipients and amounts thereof in the formulated product are pharmaceutically acceptable for subcutaneous injection products. Appropriate doses are reconstituted to a volume of about 1 mL for subcutaneous injection.

Example 1: Anti-Tumor Activity of Epcoritamab in the Presence of Anti-CD20 Antibody in Vivo and in NHL Patient-Derived Samples After Anti-CD20 Treatment The effects of the presence of an anti-CD20 antibody on the anti-tumor activity of epcoritamab in a humanized mouse xenograft model has been previously described in Engelberts et al., *EBioMedicine* 2020; 52:10265, as summarized below.

Epcoritamab was found to effectively reduce tumor growth in the xenograft model (NOD-SCID mice injected with CD20-expressing Raji-luc tumor cells and PBMCs), even in the presence of an excess of a rituximab variant with an inert Fc domain (IgG1-RTX-FEAR, containing L234F, L235E, D265A, and K409R mutations). Rituximab and IgG1-CD20, of which the CD20 arm of epcoritamab is derived, compete for CD20 binding even though they bind to a different epitope, indicating that epcoritamab is able to induce effective anti-tumor activity in the presence of circulating anti-CD20 antibodies that can compete for target binding.

Furthermore, epcoritamab induced T-cell-mediated cytotoxicity in primary DLBCL and follicular lymphoma patient biopsies taken a certain amount of time after administration of an anti-CD20 antibody (Van der Horst et al., Blood (2019) 134 (Supplement_1): 4066) Even in a biopsy taken 2 weeks after administering the anti-CD20 antibody, epcoritamab was able to induce up to 40% tumor cell kill.

Example 2: Effects of Bendamustine on the Anti-Tumor Activity of Epcoritamab in Vitro Bendamustine, an alkylating agent that causes intra- and inter-strand crosslinks between DNA bases, is approved for treatment of CLL and indolent B-NHL. This experiment was performed to determine whether bendamustine impacts the anti-tumor activity of epcoritamab by using in vitro T-cell activation and cytotoxicity assays.

Briefly, Human Burkitt lymphoma (Raji [ATCC, cat. no. CCL-86]) and DLBCL (SU-DHL-4 [Deutsche Sammlung von Mikroorganismen and Zellkulturen—DSMZ, cat. no. ACC-495]) cell lines were used as target cells. Cells were cultured in culture medium (RPMI 1640 with HEPES and L-Glutamine supplemented with 10% heat-inactivated donor bovine serum with iron, and 1% [v/v] penicillin/streptomycin) to which 2 mM L-glutamine, and 1 mM sodium pyruvate were added, at 37° C., 5% CO2. T cells, which were isolated from human healthy donor buffy coats by negative selection using the RosetteSep™ Human T Cell Enrichment Cocktail (Stemcell Technologies) followed by density centrifugation over a Ficoll gradient, both according to the manufacturer's instructions, were used as effector cells. Isolated cells were washed twice in phosphate buffered saline (PBS) and counted using acridine orange/propidium iodide (AO/PI) viability staining solution (Nexcelom Bioscience) on a Cellometer® Auto 2000 Cell Viability Counter. T cells (100,000 cells/well) were incubated with Raji or SU-DHL-4 cells (50,000 cells/well) in culture medium in the presence of epcoritamab (0.033 pg/mL-333 ng/mL) and bendamustine (0-20 µM) at 37° C., 5% CO2 for 48 hours. B-cell viability and T-cell activation were measured by flow cytometry (count of CD22-positive cells; expression of the activation markers CD69, CD25, and CD107 [LAMP-1] on CD4+ and CD8+ T cells). The percentage cytotoxicity was calculated as follows:

% cytotoxicity=100−([cell counts$_{ample}$/cell count$_{no\ antibody}$]×100%)

Figure 1B:
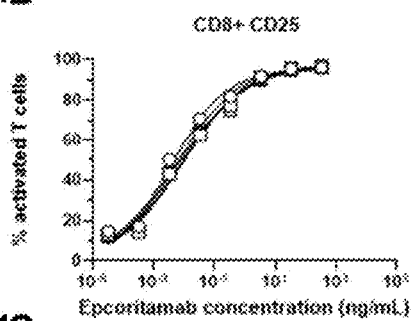
Figure 1B:
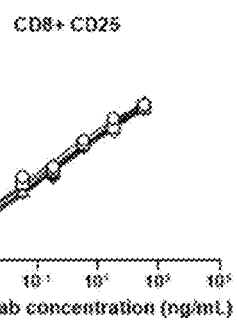
Figure 1C:
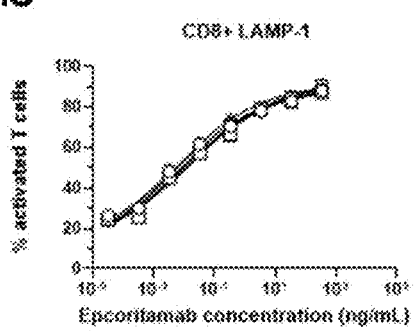
Figure 1C:
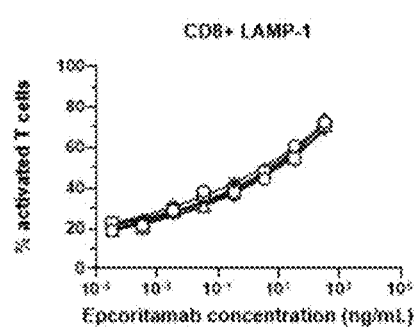
Figure 1D:
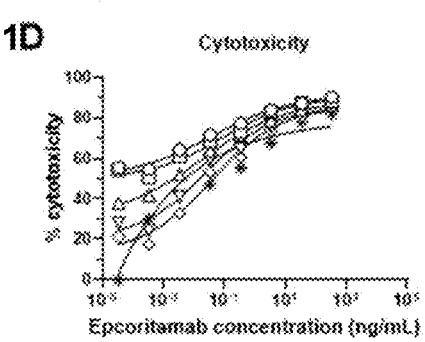
Figure 1D:
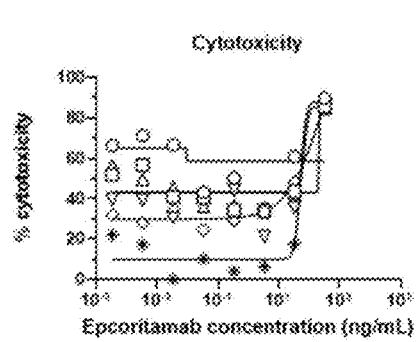

As shown in FIGS. 1A-1C, epcoritamab induced concentration-dependent activation of CD8+ T cells, as shown by upregulation of the T-cell activation markers CD69, CD25 and LAMP-1 (Lysosomal-associated membrane protein 1) expression on CD8+ T cells (FIGS. 1A-1C respectively, left panel: in presence of Raji cells, right panels: in presence of SU-DHL-4 cells). Similarly, upregulation of TR-cell activation markers by epcoritamab on CD4+ T cells was not affected by bendamustine (data not shown). Epcoritamab-induced T-cell activation was not affected by the presence of bendamustine at all concentrations tested. Incubation with bendamustine alone decreased the number of viable B cells in a dose dependent manner (FIG. 1D, start of the curves at higher percentage cytotoxicity with increasing bendamustine concentration). Epcoritamab induced concentration-dependent T-cell-mediated cytotoxicity, as measured by the decrease in the number of viable B cells, of Raji and SU-DHL-4 cells was not affected by the presence of bendamustine as the slopes are similar across the concentrations tested (FIG. 1D, left panel: Raji, right panel: SU-DHL-4). These data suggest that epcoritamab-induced T-cell-mediated cytotoxicity and T cell activation are not affected by the presence of bendamustine.

Example 3: A Phase 1b, Open-Label, Safety and Efficacy Study of Epcoritamab in Combination with Standard-of-Care Rituximab and Bendamustine for the Treatment of Previously Untreated Follicular Lymphoma An open-label, 2-part (dose escalation and expansion), multinational, multicenter interventional study is conducted to evaluate the safety, tolerability, PK, pharmacodynamics/biomarkers, immunogenicity, and preliminary efficacy of epcoritamab in combination with a standard of care regimen of rituximab and bendamustine (BR) in subjects with previously untreated follicular lymphoma.

Summary of Ongoing Clinical Trial with Epcoritamab

Epcoritamab as monotherapy is currently in a clinical trial for the treatment of relapsed/refractory (R/R) B-NHL (ClinicalTrials.gov Identifier: NCT03625037). Preliminary data suggest that the drug is tolerated at doses up to at least 48 mg, including 60 mg, in R/R B-NHL patients, with no dose-limiting toxicities reported.

Objectives

Dose Escalation

The primary objective of the dose escalation part is to evaluate the safety and tolerability of epcoritamab in combination with BR (endpoints: incidence of dose-limiting toxicities (DLTs), incidence and severity of adverse events (AEs), incidence and severity of changes in laboratory values, and incidence of dose interruptions and delays).

Secondary objectives of the dose escalation part include characterizing the PK properties of epcoritamab (endpoints: PK parameters, including clearance, volume of distribution, AUC0-last, AUC0-x, Cmax, Tmax, predose values, and half-life), evaluating pharmacodynamic markers linked to efficacy and the mechanism of action of epcoritamab (endpoints: pharmacodynamic markers in blood samples and within tumor), evaluating immunogenicity (endpoint: incidence of anti-drug antibodies (ADAs) to epcoritamab), and assessing the preliminary anti-tumor activity of epcoritamab in combination with BR (endpoints: overall response rate (ORR) by Lugano criteria and LYRIC, duration of response (DOR) by Lugano criteria and LYRIC, time to response (TTR) by Lugano criteria and LYRIC, progression free survival (PFS) by Lugano criteria and LYRIC, overall survival (OS), time to next anti-lymphoma therapy (TTNT), and rate and duration of minimal residual disease (MRD) negativity).

Exploratory objectives of the dose escalation part include assessing potential biomarkers predictive of clinical response to epcoritamab (endpoints: CD3, CD20, and other molecular/phenotypic markers pre-treatment and during treatment, DNA mutation status, and gene profile).

Expansion

The primary objective of the expansion part is to assess the preliminary anti-tumor activity of epcoritamab in combination with BR (endpoint: ORR by Lugano criteria). Secondary objectives of the expansion part include evaluating the preliminary anti-tumor activity of epcoritamab in combination with BR (endpoints: endpoints: DOR by Lugano criteria and LYRIC, TTR by Lugano criteria and LYRIC, PFS by Lugano criteria and LYRIC, ORR by LYRIC, OS, TTNT, and rate and duration of minimal residual disease (MRD) negativity), further evaluating the safety and tolerability of epcoritamab in combination with BR (endpoints: incidence and severity of changes in laboratory values, and incidence of dose interruptions and delays), characterizing the PK properties of epcoritamab (PK parameters, including clearance, volume of distribution, AUC0-last, AUC0-x, Cmax, Tmax, predose values, and half-life), evaluating pharmacodynamic markers linked to efficacy and mechanism of action of epcoritamab (endpoints: pharmacodynamic markers in blood samples and within tumor), and evaluating immunogenicity (endpoint: incidence of ADAs to epcoritamab).

Exploratory objectives of the expansion part include assessing potential biomarkers predictive of clinical response to epcoritamab (endpoints: expression of CD20 in tumors, evaluation of molecular and genetic tumor markers, immune populations, phenotype and function in tumors and blood, and DNA mutation status and gene profile), and evaluating patient-reported outcomes (PROs) (endpoint: changes in lymphoma symptoms and general health status as evaluated by the FACT-Lym).

Study Design Overview

Figure 2:
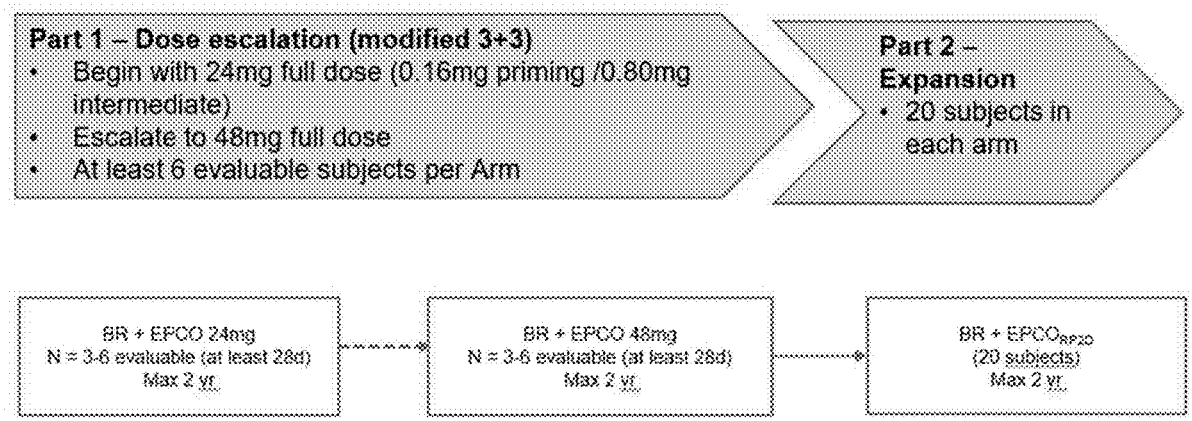
FIG. 2 is a schematic of the overall clinical trial design.

The trial is conducted in 2 parts: dose escalation (Part 1) and expansion (Part 2). Subjects participate in only one part. A schematic of the overall trial design is shown in FIG. 2. Both parts consist of a screening period, a treatment period, a safety follow-up period, and a survival follow-up period.

Dose Escalation (Part 1) and Expansion (Part 2)

Figure 3:
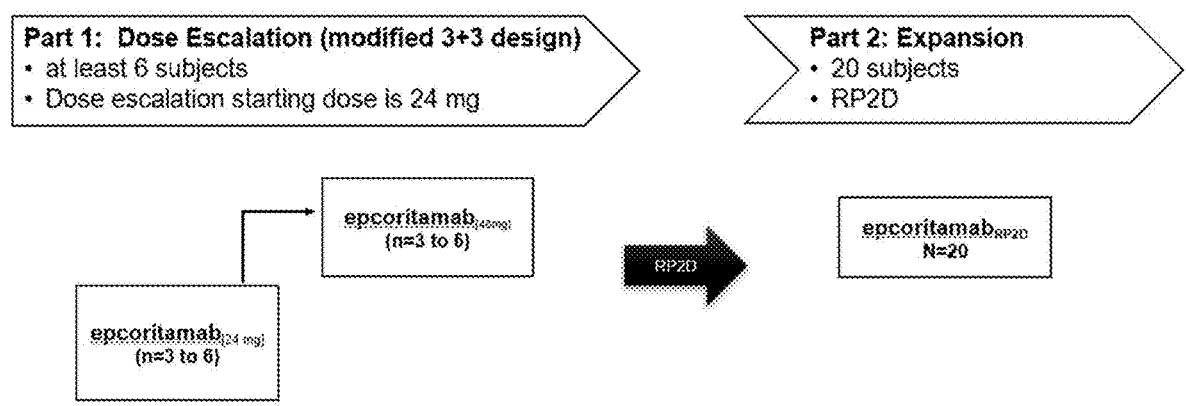
FIG. 3 is a schematic of the dose escalation design.

The Part 1 dose escalation assesses the initial safety, tolerability, and clinical activity of epcoritamab in combination with BR. Epcoritamab is initially be administered in combination with BR in a 3-subject cohort. DLTs are evaluated during the first 28 days. Depending on the number of DLTs observed in the initial 3 subjects, administration of epcoritamab (full dose: 48 mg or 24 mg) in combination with BR is performed in an additional 3 patients as shown in FIG. 3.

In Part 2, epcoritamab is administered (with the dosing regimen determined in the dose escalation part) in combination with BR. The expansion will include 20 subjects in order to evaluate the preliminary clinical activity of the combination, in addition to safety, tolerability, PK, pharmacodynamic, and immunogenicity data.

In both Part 1 and Part 2, epcoritamab is administered as a subcutaneous (SC) injection (24 mg or 48 mg; step-up dosing) for up to two years total duration of treatment with the bispecific antibody from initiation of rituximab and bendamustinecycles in combination with rituximab (intravenous) and bendamustine (intravenous), as follows:

TABLE 2

Dosing schedule

| Cycle number (28-day cycle) | Epcoritamab | Rituximab | Bendamustine |
|---|---|---|---|
| 1 | QW, step-up dosing | Q4W | Days 1 and 2 |
| 2-3 | QW | Q4W | Days 1 and 2 |
| 4-6 | Q2W | Q4W | Days 1 and 2 |
| 7-9 | Q2W | — | — |
| 10+ | Q4W | — | — |

QW: once a week (days 1, 8, 15, and 22), Q2W: once every 2 weeks (days 1 and 15), Q4W: once every 4 weeks (day 1)

A step-up dosing method is used for epcoritamab to mitigate the potential for CRS: priming dose (0.16 mg) on cycle 1 day 1, followed by intermediate dose (0.8 mg) on cycle 1 day 8, full dose (24 mg or 48 mg) on cycle 1 day 15 and day 22, and full dose in subsequent cycles. Rituximab (375 mg/m$^2$) is administered intravenously once every four weeks (Q4W) for cycles 1-6. Bendamustine (90 mg/m$^2$) is administered intravenously daily on days 1 and 2 of cycles 1-6. If bendamustine is started later than day 1 of a cycle, then planned day 1 of the next cycle is calculated from the day when bendamustine was actually initiated in order to maintain the regular cycle interval of 28 days.

The order of treatments are as follows:

TABLE 3

Treatment administration order

| Dosing order | Treatment | Dose |
|---|---|---|
| Pre-Meds | Pre-medications | As described in Table 4 |
| 1 | Rituximab | 375 mg/m$^2$ |
| 2 | Bendamustine | 90 mg/m$^2$ |
| 3 | Epcoritamab | 24 mg or 48 mg (as described in Table 2) |

Inclusion Criteria
1. Subject must be at least 18 years of age
2. ECOG PS score of 0, 1, or 2
3. CD20-positive NHL at representative tumor biopsy
4. Measurable disease defined as ≥1 measurable nodal lesion (long axis >1.5 cm and short axis >1.0 cm) or ≥1 measurable extra-nodal lesion (long axis >1.0 cm) on CT or MRI
5. Acceptable organ function at screening defined as:
   a. ANC≥1.0×10$^9$/L (growth factor use is allowed)
   b. Platelet count >75×10$^9$/L, or >50×10$^9$/L if bone marrow infiltration or splenomegaly
   c. ALT level ≤2.5 times the ULN
   d. Total bilirubin level ≤2×ULN
   e. eGFR >50 mL/min (by Cockcroft-Gault Formula)
   f. PT, INR, and aPTT <1.5×ULN, unless receiving anticoagulant
6. Histologically confirmed CD20+ FL according to the WHO 2016 classification
7. Newly diagnosed, previously untreated FL, grade 1, 2 or 3a, stage II, III, or IV
8. No prior therapy for the lymphoma other than corticosteroids not exceeding the threshold listed in exclusion criterion 9.
9. Must have a need for treatment initiation based on symptoms and/or disease burden
10. Eligible to receive BR Exclusion Criteria
1. FL grade 3b
2. Histologic evidence of transformation to an aggressive lymphoma
3. Contraindication to rituximab or bendamustine
4. History of severe allergic or anaphylactic reactions to anti-CD20 mAb therapy or known allergy or intolerance to any component or excipient of epcoritamab
5. Prior treatment with a bispecific antibody targeting CD3 and CD20
6. Chemotherapy, radiation therapy, or major surgery within 4 weeks prior to the first dose of epcoritamab
7. Treatment with an investigational drug within 4 weeks or 5 half-lives, whichever is longer, prior to the first dose of epcoritamab
8. Treatment with CAR-T therapy within 30 days prior to first dose of epcoritamab
9. Cumulative dose of corticosteroids ≥140 mg of prednisone or the equivalent within 2-week period before the first dose of epcoritamab
10. Vaccination with live vaccines within 28 days prior to the first dose of epcoritamab
11. Clinically significant cardiac disease, including:
    a. Myocardial infarction within 1 year prior to the first dose of epcoritamab, or unstable or uncontrolled disease/condition related to or affecting cardiac function (e.g., unstable angina, congestive heart failure, New York Heart Association Class III-IV), cardiac arrhythmia (CTCAE Version 4 Grade 2 or higher), or clinically significant ECG abnormalities
    b. Screening 12-lead ECG showing a baseline QTcF >470 msec
12. Evidence of significant, uncontrolled concomitant diseases that could affect compliance with the protocol or interpretation of results
13. Known active bacterial, viral, fungal, mycobacterial, parasitic, or other infection (excluding fungal infections of nail beds) at trial enrollment or significant infections within 2 weeks prior to the first dose of epcoritamab
14. CNS lymphoma or known CNS involvement by lymphoma at screening as confirmed by MRI/CT scan of the brain and, if clinically indicated, by lumbar puncture
15. Active positive tests for hepatitis B virus or hepatitis C virus indicating acute or chronic infection
16. History of HIV antibody positivity, or tests positive for HIV at screening
17. Positive test results for HTLV-1
18. Suspected active or latent tuberculosis
19. Past or current malignancy other than inclusion diagnosis, except for:
    a. Cervical carcinoma of Stage 1B or less
    b. Non-invasive basal cell or squamous cell skin carcinoma
    c. Non-invasive, superficial bladder cancer
    d. Prostate cancer with a current PSA level <0.1 ng/mL
    e. Any curable cancer with a CR of >2 years duration
20. Neuropathy >grade 1
21. Female who is pregnant, breast-feeding, or planning to become pregnant while enrolled in this trial or within 12 months after the last dose of epcoritamab
22. Male who plans to father a child while enrolled in this trial or within 12 months after the last dose of epcoritamab
23. Subject who has any condition for which participation would not be in the best interest of the subject (e.g., compromise the well-being) or that could prevent, limit, or confound the protocol-specified assessments.

CRS Prophylaxis

Administration of corticosteroids for four days is performed to reduce/prevent the severity of symptoms from potential CRS for each dose of epcoritamab. For administration of epcoritamab in cycle 2 and beyond, CRS prophylaxis with corticosteroids is optional. Corticosteroid administration can be either intravenous or oral route with recommended dose or equivalent.

Supportive therapies recommended for treatments containing rituximab include:
  Premedication with acetaminophen (650 mg orally), diphenhydramine (50 to 100 mg IV or orally), and steroids, 30 to 60 minutes before starting each rituximab infusion, to attenuate infusion reactions
  Prophylactic treatment for *Pneumocystis carinii* pneumonia
  Central nervous system (CNS) prophylaxis; subjects with 1) involvement of 2 extranodal sites and elevated LDH, or 2) lymphomatous involvement of the bone marrow, testis, or a para-meningeal site are considered to be at high risk of developing CNS disease and should receive CNS prophylaxis. CNS prophylaxis with IV methotrexate is permitted following completion of the DLT period (28 days from first dose of study treatment)

TABLE 4

Pre-medication and CRS prophylaxis

| | | | | Corticosteroids | Antihistamines | Antipyretics |
|---|---|---|---|---|---|---|
| Cycle 1 | 1st epcoritamab administration (priming dose) | Day 01* | | Prednisolone 100 mg IV (or equivalent, including oral dose) | Diphenhydramine 50 mg IV or oral (PO) (or equivalent) | Paracetamol (acetaminophen) 650 to 1000 mg PO (or equivalent) |
| | | Day 02 | | Prednisolone 100 mg IV (or equivalent, including oral dose) | | |
| | | Day 03 | | Prednisolone 100 mg IV (or equivalent, including oral dose) | | |
| | | Day 04 | | Prednisolone 100 mg IV (or equivalent, including oral dose) | | |

TABLE 4-continued

| | | | Pre-medication and CRS prophylaxis | | |
|---|---|---|---|---|---|
| | | | Corticosteroids | Antihistamines | Antipyretics |
| | 2nd epcoritamab administration (intermediate dose) | Day 08* | Prednisolone 100 mg IV (or equivalent including oral dose) | Diphenhydramine 50 mg IV or oral (PO) (or equivalent) | Paracetamol (acetaminophen) 650 to 1000 mg PO (or equivalent) |
| | | Day 09 | Prednisolone 100 mg IV (or equivalent including oral dose) | | |
| | | Day 10 | Prednisolone 100 mg IV (or equivalent including oral dose) | | |
| | | Day 11 | Prednisolone 100 mg IV (or equivalent, including oral dose) | | |
| | 3rd epcoritamab administration (full dose) | Day 15* | At least prednisolone 100 mg IV (or equivalent including oral dose) | Diphenhydramine 50 mg IV or oral (PO) (or equivalent) | Paracetamol (acetaminophen) 650 to 1000 mg PO (or equivalent) |
| | | Day 16 | At least prednisolone 100 mg IV (or equivalent including oral dose) | | |
| | | Day 17 | At least prednisolone 100 mg IV (or equivalent including oral dose) | | |
| | | Day 18 | Prednisolone 100 mg IV (or equivalent, including oral dose) | | |
| Cycle 1 | 4th epcoritamab administration (full dose) | Day 22 | At least prednisolone 100 mg IV (or equivalent including oral dose) | Diphenhydramine 50 mg IV or oral (PO) (or equivalent) | Paracetamol (acetaminophen) 650 to 1000 mg PO (or equivalent) |
| | | Day 23 | At least prednisolone 100 mg IV (or equivalent including oral dose) | | |
| | | Day 24 | At least prednisolone 100 mg IV (or equivalent including oral dose) | | |
| | | Day 25 | Prednisolone 100 mg IV (or equivalent, including oral dose) | | |
| Cycle 2 | 5th epcoritamab administration (full dose) | Day 29* Day 30 | If CRS > grade 1 occurs following the 4th epcoritamab administration, 4-day consecutive corticosteroid administration is continued in Cycle 2 until CRS recedes. | Optional | Optional |

*30 minutes to 2 hours prior to administration of epcoritamab

Note:
If epcoritamab dose is administered more than 24 h after the start of BR, the premedication is administered prior to epcoritamab dose and corticosteroid prophylaxis is continued for 3 days following the epcoritamab administration.

TABLE 5

Corticosteroid Dose Equivalents - Conversion Table

| Glucocorticoid | Approximate equivalent dose (mg) |
|---|---|
| Short-acting | |
| Cortisone (PO) | 500 |
| Hydrocortisone (IV or PO) | 400 |
| Intermediate-acting | |
| Methylprednisolone (IV or PO) | 80 |
| Prednisolone (PO) | 100 |
| Prednisone (IV or PO) | 100 |
| Triamcinolone (IV) | 80 |
| Long-acting | |
| Betamethasone (IV) | 15 |
| Dexamethasone (IV or PO) | 15 |

Supportive Care for Cytokine Release Syndrome

CRS is graded according to the ASTCT grading for CRS (Tables 6 and 7), and for treatment of CRS, subjects should receive supportive care. Supportive care can include, but is not limited to, Infusion of saline Systemic glucocorticosteroid, antihistamine, antipyrexia Support for blood pressure (vasopressin, vasopressors)

Support for low-flow and high-flow oxygen and positive pressure ventilation

Monoclonal antibody against IL-6R, e.g., IV administration of tocilizumab

Monoclonal antibody against IL-6, e.g., IV siltuximab if not responding to repeated tocilizumab.

TABLE 6

Grading and Management of Cytokine Release Syndrome
Harmonized definitions and grading criteria for CRS, per the American Society for Transplantation and Cellular Therapy (ASTCT), formerly American Society for Blood and Marrow Transplantation, (ASBMT), are presented below.
Grading of Cytokine Release Syndrome

| CRS parameter | Grade 1 | Grade 2 | Grade 3 | Grade 4 | Grade 5 |
|---|---|---|---|---|---|
| Fever[1] With hypotension | ≥38.0° C. None | ≥38.0° C. Not requiring vasopressors | ≥38.0° C. Requiring 1 vasopressor with or without vasopressin | ≥38.0° C. Requiring ≥2 vasopressors (excluding vasopressin) | Death due to CRS in which another cause is not the principle factor leading to this outcome |
| And/or hypoxia[2] | None | Requiring low-flow (≤6 L/minute) nasal cannula or blow-by | Requiring high-flow (>6 L/minute) nasal cannula, facemask, nonrebreather mask, or venturi mask | Requiring positive pressure ventilation[3] (eg, CPAP, BiPAP, intubation and mechanical ventilation) | |

Abbreviations: BiPAP, Bilevel positive airway pressure; CPAP, continuous positive airway pressure; CRS, cytokine release syndrome; IV, intravenous.
Note:
organ toxicities or constitutional symptoms associated with CRS may be graded according to CTCAE but they do not influence CRS grading.
[1]Fever is defined as temperature ≥38.0° C. not attributable to any other cause, with or without constitutional symptoms (eg, myalgia, arthralgia, malaise). In subjects who have CRS receiving antipyretics, anticytokine therapy, and/or corticosteroids, fever is no longer required to grade subsequent CRS severity. In this case, CRS grading is driven by hypotension and/or hypoxia.
[2]CRS grade is determined by the more severe event: hypotension or hypoxia not attributable to any other cause. For example, a subject with temperature of 39.5° C., hypotension requiring 1 vasopressor, and hypoxia requiring low-flow nasal cannula is classified as grade 3 CRS. Both systolic blood pressure and mean arterial pressure are acceptable for blood pressure measurement. No specific limits are required, but hypotension should be determined on a case-by-case basis, accounting for age and the subject's individual baseline, i.e., a blood pressure that is below the normal expected for an individual in a given environment.
[3]Intubation of a subject without hypoxia for the possible neurologic compromise of a patent airway alone or for a procedure is not by definition grade 4 CRS.
Source: Adapted from Lee et al., Biol Blood Marrow Transplant 2019; 25: 625-638

TABLE 7

Grading and Management of Cytokine Release Syndrome

| CRS grade | Management |
|---|---|
| 1 | Fever: Patients with a new fever should be admitted to the hospital if not already. Investigate for infection and rapidly startup broad-spectrum antibiotics. Continuation of antibiotic therapy is recommended until and potential neutropenia resolve. Constitutional symptoms may be helped by NSAIDs. Tocilizumab: No*. Steroids: No. |

TABLE 7-continued

Grading and Management of Cytokine Release Syndrome

| CRS grade | Management |
|---|---|
| 2 | Fever: As per grade 1.<br>Hypotension: Immediate clinical evaluation and intervention is warranted. At the first confirmed decrease ≥20% from baseline systolic, diastolic or mean arterial pressure or evidence of worsening perfusion, administer an IV fluid bolus (20 mL/kg up to 1 L). Consider a vasopressor and administer no later than after the $3^{rd}$ IV fluid bolus due the vasodilatation and capillary leak associated with CRS.<br>Hypoxia: Consider X-ray or CT-scan if hypoxic and/or tachypneic. Administer oxygen by low-flow nasal cannula (≤6 L/min) or blow-by.<br>Tocilizumab: No* (yes, if the patient has comorbidities†).<br>Steroids: No (consider, if the patient has comorbidities‡). |
| 3 | Fever: As per grade 1.<br>Hypotension: Immediate clinical evaluation and intervention is warranted. Administer a vasopressor (norepinephrine), with or without vasopressin, as most patients with CRS have peripheral vasodilation.<br>Hypoxia: Administer oxygen by high-flow nasal cannula (>6 L/min), facemask, non-breather mask, or Venturi mask.<br>Tocilizumab: Yes†.<br>Steroids: Consider‡. |
| 4 | Fever: As per grade 1.<br>Hypotension: Immediate clinical evaluation and intervention is warranted. Administer at least 2 vasopressors, with or without vasopressin, as most patients with CRS have peripheral vasodilation.<br>Hypoxia: Positive pressure (e.g. CPAP, BiPAP, intubation, and mechanical ventilation).<br>Tocilizumab: Yes†.<br>Steroids: Yes‡. |

*Consider intervening earlier in specific cases. For example, an elderly patient with prolonged fever (>72 hours) or very high fever (>40.5° C./104.9° F.) may not tolerate the resulting sinus tachycardia as well as a younger patient, so tocilizumab may be indicated.
†Tocilizumab (anti-IL-6R) remains the only first-line anticytokine therapy approved for CRS. If there is no improvement in symptoms within 6 hours, or if the patient starts to deteriorate after initial improvement, a second dose of tocilizumab should be administered along with a dose of corticosteroids. For patients being refractory to tocilizumab (3 administrations), additional anticytokine therapy such as siltuximab (anti-IL-6) or anakinra (anti-IL-1R) may be considered. However, such use is entirely anecdotal and, as such, is entirely at the discretion of the treating physician.
‡Consider dexamethasone over methylprednisolone due to improved CNS penetration even in absence of neurotoxicity, as high-grade CRS is correlated with risk of concurrent or subsequent ICANS. If concurrent ICANS is observed, dexamethasone should be preferred.
Source: (Varadarajan I, Kindwall-Keller T L, Lee D W (2020). Management of cytokine release syndrome. In: Chimeric antigen receptor T-cell therapies for cancer (Chapter 5). Elsevier 2020)

Tumor Lysis Syndrome Prevention and Management

For prophylactic treatment of tumor lysis syndrome, subjects receive hydration and uric acid reducing agents prior to the administration of epcoritamab. If signs of tumor lysis syndrome (TLS) occur, supportive therapy, including rasburicase, is used.

Dose Modification Guidance and Safety Management

There will be no dose modification for epcoritamab (see FIG. 3 for exceptions in the dose escalation cohorts) or rituximab, although they may be held or discontinued depending on any toxicities (and grade of toxicities) subjects develop during their use.

For bendamustine, myelosuppression may require dose delays and/or subsequent dose reductions if recovery to the recommended values has not occurred by the first day of the next scheduled cycle. Prior to the initiation of the next cycle of therapy, the ANC should be $\geq 1 \times 10^9$/L and the platelet count should be $\geq 75 \times 10^9$/L.

Bendamustine administration is delayed in the event of a Grade 3 hematologic toxicity or clinically significant ≥Grade 2 non-hematologic toxicity. Once non-hematologic toxicity has recovered to ≤Grade 1 and/or the blood counts have improved (ANC≥$1 \times 10^9$/L, platelets ≥$75 \times 10^9$/L), bendamustine is re-initiated at the discretion of the treating physician. Dose reduction may also be considered.

Dose modifications for hematologic toxicity: for Grade 3 toxicity lasting more than 2 days, reduce the dose to 70 mg/m² on Days 1 and 2 of each cycle; for Grade 4 toxicity, reduce the dose to 60 mg/m² on Days 1 and 2 of each cycle; if Grade 4 toxicity recurs, discontinue bendamustine.

Dose modifications for non-hematologic toxicity: for Grade 3 or greater toxicity, reduce the dose to 60 mg/m² on Days 1 and 2 of each cycle; if Grade 3 or greater toxicity recurs, discontinue bendamustine.

Study Assessments

Demographics and Baseline Assessments

Demographic details of subjects are collected, as is information such as date of lymphoma diagnosis, Ann Arbor Staging at diagnosis, including constitutional symptoms (B symptoms), and prior evidence of CD20 positivity. Medical history, information regarding prior and concomitant medications, concomitant procedures, and prior cancer therapies and surgeries (including prior anti-cancer therapy for NHL, such as surgery, radiotherapy, chemo-radiotherapy, and systemic treatment regimens), are also collected.

Efficacy Assessments

Eligible subjects have at least 1 measurable site of disease (as indicated in the inclusion criteria) for disease evaluations. Measurable sites of lymphoma are defined as lymph nodes, lymph node masses, or extranodal sites. Measurements are determined by imaging evaluation, with up to 6 measurable sites followed as target lesions for each subject. Sites not measurable as defined above are considered assessable by objective evidence of disease (i.e., radiographic imaging, physical examination, or other procedures). Examples of assessable disease include, e.g., bone marrow involvement, bone lesions, effusions, or thickening of bowel wall.

Tumor and Bone Marrow Biopsies

Two fresh core tumor biopsies are collected before treatment with epcoritamab (during the screening period) and 2 fresh core tumor biopsies at the start of cycle 2 day 15 (±1 week) for all subjects with accessible tumors. An archival tumor biopsy, if collected within 3 months prior to enrollment, is acceptable if a fresh biopsy at screening cannot be collected. The biopsy can be a whole lymph node or a core biopsy. Tumor biopsies should be FFPE. Tumor biopsies are examined for MRD assessment and exploratory biomarkers.

Radiographic Assessments

An FDG PET-CT scan (or CT/MRI and FDG PET when PET-CT scan not available) is performed during Screening. For subjects with FDG-avid tumors at Screening, all subsequent disease assessments include FDG-PET using the 5-point scale described in Barrington et al. (*J Clin Oncol* 2014; 32:3048-58; Score 1: No uptake; Score 2: Uptake-≤mediastinum; Score 3: Update>mediastinum but≤liver; Score 4: Uptake moderately higher than liver; Score 5: Uptake markedly higher than liver and/or new lesions; Score X: new areas of update unlikely to be related to lymphoma). For subjects with non-avid or variably FDG-avid tumors, CT scan with IV contrast of neck/chest/abdomen/pelvis/additional known lesions may be performed. The CT component of the PET-CT may be used in lieu of a standalone CT/MRI, if the CT component is of similar diagnostic quality as a contrast enhanced CT performed without PET. If contrast enhanced PET-CT is not available, a standalone diagnostic CT/MRI and a standard FDG-PET is performed. Subjects who are intolerant of IV CT contrast agents undergo CT scans with oral contrast.

MRI can be used to evaluate sites of disease that cannot be adequately imaged using CT or for subjects intolerant of CT contrast agents. In cases where MRI is the imaging modality of choice, the MRI is obtained at screening and at all subsequent response evaluations.

Bone Marrow Assessments

A bone marrow biopsy (archival or fresh), with or without aspirate, is obtained at screening for all patients to document bone marrow involvement with lymphoma. A bone marrow biopsy obtained as routine SOC may be used if taken up to 42 days before first dose of epcoritamab. If bone marrow aspirate is obtained, determination of bone marrow involvement can be confirmed by flow cytometry. A bone marrow biopsy is taken (1) at screening; (2) for subjects with bone marrow involvement at screening who later achieve CR by imaging—bone marrow evaluation includes morphological examination and either flow cytometry or IHC, if warranted, to confirm the presence or absence (complete remission) of lymphoma; (3) for subjects with bone marrow involvement documented at screening who later achieve CR by imaging—a portion of the aspirate collected to confirm CR will be used for MRD assessments.

Minimal Residual Disease Assessment

MRD is assessed by tracking the presence of DNA that encodes the B cell receptor (BCR) expressed specifically by the cancer cells. The DNA sequence of this BCR is identified by tumor biopsy submitted at screening. After the start of treatment, blood samples are taken at fixed timepoints and at the time of CR to assess whether the amount of cancer DNA is declining, as a potential measure of (early) response, and to assess MRD. As an exploratory analysis, when a subject reaches a metabolic/radiologic CR and has bone marrow involvement documented at screening, a portion of the aspirate collected to confirm CR is used to assess MRD.

Disease Response and Progressive Disease Assessment

Disease response is assessed according to both Lugano criteria (described in Cheson et al., *J Clin Oncol* 2014; 32:3059-68 (see, in particular, Table 3 in Cheson et al., 2014) and LYRIC (Table 8) to inform decisions on continuation of treatment.

Endpoint definitions are as follows:

Overall response rate (ORR), is defined as the proportion of subjects who achieve a response of PR or CR, prior to initiation of subsequent therapy.

Time to response (TTR), is defined among responders, as the time between first dose (from day 1, cycle 1) of epcoritamab and the initial documentation of PR or CR.

Duration of response (DOR), is defined among responders, as the time from the initial documentation of PR or CR to the date of disease progression or death, whichever occurs earlier.

Progression-free survival (PFS), is defined as the time from the first dosing date (day 1, cycle 1) of epcoritamab and the date of disease progression or death, whichever occurs earlier.

Overall survival (OS), is defined as the time from the first dosing date (day 1, cycle 1) of epcoritamab and the date of death.

Time to next anti-lymphoma therapy (TTNT), is defined as the number of days from day 1 of cycle 1 to the first documented administration of subsequent anti-lymphoma therapy.

MRD negativity rate, is defined as the proportion of subjects with at least 1 undetectable MRD result according to the specific threshold, prior to initiation of subsequent therapy. Lugano criteria (see, e.g., Cheson et al., *J Clin Oncol* 2014; 32:3059-68, for definitions of complete response, partial response, no response/stable disease, and progressive disease)

(a) Target and Non-Target Lesions

Target lesions for the Lugano criteria include up to 6 of the largest dominant nodes, nodal masses, or other lymphomatous lesions that are measurable in two diameters and are preferably from different body regions representative of the subject's overall disease burden, including mediastinal and retroperitoneal disease, where applicable. At baseline, a measurable node is >15 mm in longest diameter (LDi). Measurable extranodal disease may be included in the six representative target lesions. At baseline, measurable extranodal lesions should be >10 mm in LDi.

All other lesions (including nodal, extranodal, and assessable disease) may be followed as non-target lesions (e.g., cutaneous, GI, bone, spleen, liver, kidneys, pleural or pericardial effusions, ascites, bone, bone marrow).

(b) Split Lesions and Confluent Lesions

Lesions may split or may become confluent over time. In the case of split lesions, the individual product of the perpendicular diameters (PPDs) of the nodes should be summed together to represent the PPD of the split lesion; this PPD is added to the sum of the PPDs of the remaining lesions to measure response. If subsequent growth of any or all of these discrete nodes occurs, the nadir of each individual node is used to determine progression. In the case of confluent lesions, the PPD of the confluent mass should be compared with the sum of the PPDs of the individual nodes, with more than 50% increase in PPD of the confluent mass compared with the sum of individual nodes necessary to indicate progressive disease (PD). The LDi and smallest diameter (SDi) are no longer needed to determine progression.

LYRIC

Clinical studies have shown that cancer immunotherapies may result in early apparent radiographic progression (including the appearance of new lesions), followed by a delayed response. As this initial increase in tumor size might be caused by immune-cell infiltration in the setting of a T-cell response, this progression may not be indicative of true disease progression and is therefore called "pseudoprogression" (Wolchok et al., Clin Cancer Res 2009; 15:7412-20).

The current Lugano response assessment criteria (Cheson et al., J Clin Oncol 2014; 32:3059-68) does not take pseudoprogression into account, and there is a significant risk of premature discontinuation of a potentially efficacious immunomodulatory drug following the observation of an atypical response. Atypical responses are characterized either by the early progression of existing lesions, later followed by response, or by the development of new lesions, with or without tumor shrinkage elsewhere.

LYRIC is a modification of the Lugano response assessment criteria, which has been adapted to immune-based therapies, and it implements a new, mitigating response category: the "indeterminate response" (IR) designation (Cheson et al., Blood 2016; 128:2489-96). This IR designation was introduced to potentially identify "atypical response" cases until confirmed as flare/pseudoprogression or true PD by either biopsy or subsequent imaging.

A subject who shows PD according Lugano criteria/classification will be considered to have IR in 1 or more of the 3 following circumstances:

IR (1): Increase in overall tumor burden (as assessed by sum of the product of the diameters [SPD]) of ≅50% of up to 6 target lesions in the first 12 weeks of therapy, without clinical deterioration.

IR (2): Appearance of new lesions or growth of one or more existing lesion(s) ≥50% at any time during treatment; occurring in the context of lack of overall progression (SPD <50% increase) of overall tumor burden, as measured by SPD of up to 6 lesions at any time during the treatment.

IR (3): Increase in FDG uptake of 1 or more lesion(s) without a concomitant increase in lesion size or number.

It is possible that, at a single time point, a subject could fulfill criteria for both IR(1) or IR(2) and IR(3): for example, there could be a new FDG-avid lesion in the absence of overall progression (IR[2]), and, at the same time, increase in FDG uptake of a separate lesion (IR[3]). In such cases, the designation of IR(1) or IR (2) should take priority (e.g., IR[2] in the above example).

Subjects categorized as having any of the IR types receive repeat imaging after an additional 12 weeks (or earlier if clinically indicated). At that time, response should be re-evaluated, and the subject should be considered to have true PD with the following considerations:

Follow-up IR(1): In case of IR(1), comparison should be made between the first IR(1) and the current SPD. The IR(1) will become PD if: (a) SPD increases by ≥10% from first IR1 AND (b) an increase of ≥5 mm (in either dimension) of ≥1 lesion for lesions ≤2 cm and ≥10 mm for lesions >2 cm, to be consistent with Lugano criteria.

Follow-up IR(2): In case of IR(2), the new or growing lesion(s) is added to the target lesion(s), up to a total of no more than 6 total lesions. The IR(2) will become PD if: (a) ≥50% increase in SPD (newly defined set of target lesions) from nadir value.

Follow-up IR(3): The IR(3) will become PD if lesion with increased FDG uptake also shows size increase.

TABLE 8

| | | | LYRIC | |
| --- | --- | --- | --- | --- |
| | CR | PR | SD | PD |
| LYRIC | Same as Lugano Classification | Same as Lugano Classification | Same as Lugano Classification | As with Lugano with the following exceptions: IR Categories: IR (1): ≥50% increase in SPD in first 12 weeks of therapy IR (2): <50% increase in SPD with a) New lesion(s), or b) ≥50% increase of 1 lesion or set of lesions at any time during treatment IR (3): Increase in FDG uptake without a concomitant increase in lesion size meeting criteria for PD |

Clinical Safety Assessments

Safety is assessed by measuring adverse events, laboratory test results, ECGs, vital sign measurements, physical examination findings, and ECOG performance status. Also assessed are immune effector cell-associated neurotoxicity syndrome (e.g., as described by Lee et al., Biol Blood Marrow Transplant 2019; 25:625-638), constitutional symptoms (B symptoms), tumor flare reaction, and survival.

Patient-Reported Outcomes

Patient-reported outcomes are evaluated using the FACT-Lym health-related quality of life (QOL) questionnaire, which assesses QOL in lymphoma patients.

Preliminary Results

As of Sep. 8, 2021, a total of 17 patients were dosed. The expansion phase for 48 mg was opened on Jun. 28, 2021. 5 responders were observed in dose escalation phase and 1 responder in expansion phase. The most common related AEs were CRS and Nausea. All CRS were Grade 1/2. These data are preliminary and non-validated and unclean data and response data were not completely entered by site.

TABLE 9

Summary of Sequences

| SEQ ID | Description | Sequence |
|---|---|---|
| 1 | huCD3 VH CDR1 | GFTFNTYA |
| 2 | huCD3 VH CDR2 | IRSKYNNYAT |
| 3 | huCD3 VH CDR3 | VRHGNFGNSYVSWFAY |
| 4 | huCD3 VL CDR1 | TGAVTTSNY |
| — | huCD3 VL CDR2 | GTN |
| 5 | huCD3 VL CDR3 | ALWYSNLWV |
| 6 | huCD3 VH1 | EVKLVESGGGLVQPGGSLRLSCAAS<u>GFTFNTYA</u>MNWVRQAPGKGLE WVAR<u>IRSKYNNYAT</u>YYADSVKDRFTISRDDSKSSLYLQMNNLKTEDTA MYYC<u>VRHGNFGNSYVSWFAY</u>WGQGTLVTVSS |
| 7 | huCD3 VL1 | QAVVTQEPSFSVSPGGTVTLTCRSS<u>TGAVTTSNY</u>ANWVQQTPGQAF RGLIG<u>GTN</u>KRAPGVPARFSGSLIGDKAALTITGAQADDESIYFC<u>ALWYS NLWV</u>FGGGTKLTVL |
| 8 | VH CD20-7D8 CDR1 | GFTFHDYA |
| 9 | VH CD20-7D8 CDR2 | ISWNSGTI |
| 10 | VH CD20-7D8 CDR3 | AKDIQYGNYYYGMDV |
| 11 | VL CD20-7D8 CDR1 | QSVSSY |
| — | VL CD20-7D8 CDR2 | DAS |
| 12 | VL CD20-7D8 CDR3 | QQRSNWPIT |
| 13 | VH CD20-7D8 | EVQLVESGGGLVQPDRSLRLSCAAS<u>GFTFHDYA</u>MHWVRQAPGKGLE WVST<u>ISWNSGTI</u>GYADSVKGRFTISRDNAKNSLYLQMNSLRAEDTAL YYC<u>AKDIQYGNYYYGMDV</u>WGQGTTVTVSS |
| 14 | VL CD20-7D8 | EIVLTQSPATLSLSPGERATLSCRAS<u>QSVSSY</u>LAWYQQKPGQAPRLLIY <u>DAS</u>NRATGIPARFSGSGSGTDFTLTISSLEPEDFAVYYC<u>QQRSNWPIT</u>F GQGTRLEIK |
| 15 | IgG1 heavy chain constant region-WT (amino acids positions 118-447 according to EU numbering). CH3 region italics | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAK*GQPREPQVYTLPPSRE EMTKNQVSLTCLVKGFYPSDIAVEWESNGQPENNYKTTPPVLDSDGS FFLYSKLTVDKSRWQQGNVFSCSVMHEALHNHYTQKSLSLSPG* |
| 16 | IgG1-LFLEDA heavy chain constant region (amino acids positions 118-447 according to EU numbering). | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPEFEGGPSVFLFPPKPKDTLMISRTPEVTCV VVAVSHEDPEVKFNWYVDGVEVHNAKTKPREEQYNSTYRVVSVLTV LHQDWLNGKEYKCKVSNKALPAPIEKTISKAKGQPREPQVYTLPPSRE EMTKNQVSLTCLVKGFYPSDIAVEWESNGQPENNYKTTPPVLDSDGS FFLYSKLTVDKSRWQQGNVFSCSVMHEALHNHYTQKSLSLSPG |
| 17 | IgG1 F405L (amino acids positions 118-447 according to EU numbering) | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRE EMTKNQVSLTCLVKGFYPSDIAVEWESNGQPENNYKTTPPVLDSDGS FLLYSKLTVDKSRWQQGNVFSCSVMHEALHNHYTQKSLSLSPG |
| 18 | IgG1-K409R (amino acids positions 118-447 according to EU numbering) | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRE EMTKNQVSLTCLVKGFYPSDIAVEWESNGQPENNYKTTPPVLDSDGS FFLYSRLTVDKSRWQQGNVFSCSVMHEALHNHYTQKSLSLSPG |

TABLE 9-continued

Summary of Sequences

| SEQ ID | Description | Sequence |
|---|---|---|
| 19 | IgG1-LFLEDA-F405L (FEAL) (amino acids positions 118-447 according to EU numbering) | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPEFEGGPSVFLFPPKPKDTLMISRTPEVTCV VVAVSHEDPEVKFNWYVDGVEVHNAKTKPREEQYNSTYRVVSVLTV LHQDWLNGKEYKCKVSNKALPAPIEKTISKAKGQPREPQVYTLPPSRE EMTKNQVSLTCLVKGFYPSDIAVEWESNGQPENNYKTTPPVLDSDGS FLLYSKLTVDKSRWQQGNVFSCSVMHEALHNHYTQKSLSLSPG |
| 20 | IgG1-LFLEDA-K409R (FEAR) (amino acids positions 118-447 according to EU numbering) | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPEFEGGPSVFLFPPKPKDTLMISRTPEVTCV VVAVSHEDPEVKFNWYVDGVEVHNAKTKPREEQYNSTYRVVSVLTV LHQDWLNGKEYKCKVSNKALPAPIEKTISKAKGQPREPQVYTLPPSRE EMTKNQVSLTCLVKGFYPSDIAVEWESNGQPENNYKTTPPVLDSDGS FFLYSRLTVDKSRWQQGNVFSCSVMHEALHNHYTQKSLSLSPG |
| 21 | IgG1 CH3 region | GQPREPQVYTLPPSREEMTKNQVSLTCLVKGFYPSDIAVEWESNGQP ENNYKTTPPVLDSDGSFFLYSKLTVDKSRWQQGNVFSCSVMHEALH NHYTQKSLSLSPG |
| 22 | Constant region human lambda LC | GQPKAAPSVTLFPPSSEELQANKATLVCLISDFYPGAVTVAWKADSSP VKAGVETTTPSKQSNNKYAASSYLSLTPEQWKSHRSYSCQVTHEGST VEKTVAPTECS |
| 23 | Constant region human kappa LC | RTVAAPSVFIFPPSDEQLKSGTASVVCLLNNFYPREAKVQWKVDNAL QSGNSQESVTEQDSKDSTYSLSSTLTLSKADYEKHKVYACEVTHQGLS SPVTKSFNRGEC |
| 24 | huCD3-LFLEDA-F405L (FEAL) heavy chain | EVKLVESGGGLVQPGGSLRLSCAASGFTFNTYAMNWVRQAPGKGLE WVARIRSKYNNYATYYADSVKDRFTISRDDSKSSLYLQMNNLKTEDTA MYYCVRHGNFGNSYVSWFAYWGQGTLVTVSSASTKGPSVFPLAPSS KSTSGGTAALGCLVKDYFPEPVTVSWNSGALTSGVHTFPAVLQSSGLY SLSSVVTVPSSSLGTQTYICNVNHKPSNTKVDKRVEPKSCDKTHTCPPC PAPEFEGGPSVFLFPPKPKDTLMISRTPEVTCVVVAVSHEDPEVKFNW YVDGVEVHNAKTKPREEQYNSTYRVVSVLTVLHQDWLNGKEYKCKV SNKALPAPIEKTISKAKGQPREPQVYTLPPSREEMTKNQVSLTCLVKGF YPSDIAVEWESNGQPENNYKTTPPVLDSDGSFLLYSKLTVDKSRWQQ GNVFSCSVMHEALHNHYTQKSLSLSPG |
| 25 | huCD3 VL + CL light chain | QAVVTQEPSFSVSPGGTVTLTCRSSTGAVTTSNYANWVQQTPGQAF RGLIGGTNKRAPGVPARFSGSLIGDKAALTITGAQADDESIYFCALWYS NLWVFGGGTKLTVLGQPKAAPSVTLFPPSSEELQANKATLVCLISDFY PGAVTVAWKADSSPVKAGVETTTPSKQSNNKYAASSYLSLTPEQWKS HRSYSCQVTHEGSTVEKTVAPTECS |
| 26 | CD20-7D8-LFLEDA-K409R (FEAR) heavy chain | EVQLVESGGGLVQPDRSLRLSCAAS<u>GFTFHDYAM</u>HWVRQAPGKGLE WVST<u>ISWNSGTI</u>GYADSVKGRFTISRDNAKNSLYLQMNSLRAEDTAL YYC<u>AKDIQYGNYYYGMD</u>VWGQGTTVTVSSASTKGPSVFPLAPSSKST SGGTAALGCLVKDYFPEPVTVSWNSGALTSGVHTFPAVLQSSGLYSLS SVVTVPSSSLGTQTYICNVNHKPSNTKVDKRVEPKSCDKTHTCPPCPA PEFEGGPSVFLFPPKPKDTLMISRTPEVTCVVVAVSHEDPEVKFNWYV DGVEVHNAKTKPREEQYNSTYRVVSVLTVLHQDWLNGKEYKCKVSN KALPAPIEKTISKAKGQPREPQVYTLPPSREEMTKNQVSLTCLVKGFYP SDIAVEWESNGQPENNYKTTPPVLDSDGSFFLYSRLTVDKSRWQQG NVFSCSVMHEALHNHYTQKSLSLSPG |
| 27 | CD20-7D8 VL + CL light chain | EIVLTQSPATLSLSPGERATLSCRASQSVSSYLAWYQQKPGQAPRLLIY DASNRATGIPARFSGSGSGTDFTLTISSLEPEDFAVYYCQQRSNWPITF GQGTRLEIKRTVAAPSVFIFPPSDEQLKSGTASVVCLLNNFYPREAKVQ WKVDNALQSGNSQESVTEQDSKDSTYSLSSTLTLSKADYEKHKVYACE VTHQGLSSPVTKSFNRGEC |
| 28 | Human CD3 (epsilon) | MQSGTHWRVLGLCLLSVGVWGQDGNEEMGGITQTPYKVSISGTTVI LTCPQYPGSEILWQHNDKNIGGDEDDKNIGSDEDHLSLKEFSELEQSG YYVCYPRGSKPEDANFYLYLRARVCENCMEMDVMSVATIVIVDICITG GLLLLVYYWSKNRKAKAKPVTRGAGAGGRQRGQNKERPPPVPNPDY EPIRKGQRDLYSGLNQRRI |

TABLE 9-continued

Summary of Sequences

| SEQ ID | Description | Sequence |
|---|---|---|
| 29 | Human CD20 | MTTPRNSVNGTFPAEPMKGPIAMQSGPKPLFRRMSSLVGPTQSFFM RESKTLGAVQIMNGLFHIALGGLLMIPAGIYAPICVTVWYPLWGGIM YIISGSLLAATEKNSRKCLVKGKMIMNSLSLFAAISGMILSIMDILNIKIS HFLKMESLNFIRAHTPYINIYNCEPANPSEKNSPSTQYCYSIQSLFLGILS VMLIFAFFQELVIAGIVENEWKRTCSRPKSNIVLLSAEEKKEQTIEIKEEV VGLTETSSQPKNEEDIEIIPIQEEEEETETNFPEPPQDQESSPIENDSSP |

Bold and underlined are FE; A; L and R, corresponding to positions 234 and 235; 265; 405 and 409, respectively, said positions being in accordance with EU-numbering. In variable regions, said CDR regions that were annotated in accordance with IMGT definitions are underlined.

The invention claimed is:

1. A method of treating follicular lymphoma in a human subject, the method comprising administering to the subject a bispecific antibody and an effective amount of rituximab and bendamustine, wherein the bispecific antibody comprises:
   (i) a first binding arm comprising a first antigen-binding region which binds to human CD3ε (epsilon) and comprises a variable heavy chain (VH) region and a variable light chain (VL) region, wherein the VH region comprises the CDR1, CDR2 and CDR3 sequences that are in the VH region sequence of SEQ ID NO: 6, and the VL region comprises the CDR1, CDR2 and CDR3 sequences that are in the VL region sequence of SEQ ID NO: 7; and
   (ii) a second binding arm comprising a second antigen-binding region which binds to human CD20 and comprises a VH region and a VL region, wherein the VH region comprises the CDR1, CDR2 and CDR3 sequences that are in the VH region sequence of SEQ ID NO: 13, and the VL region comprises the CDR1, CDR2 and CDR3 sequences that are in the VL region sequence of SEQ ID NO: 14;
   wherein the bispecific antibody is administered at a dose of 24 mg or 48 mg, and wherein rituximab, bendamustine, and the bispecific antibody are administered in 28-day cycles,
   wherein the bispecific antibody, rituximab, and bendamustine are administered in the same cycle for the first 6 cycles, and the bispecific antibody is administered alone for subsequent cycles, and wherein a priming dose of the bispecific antibody is administered on day 1 of cycle 1 and an intermediate dose is administered on day 8 of cycle 1 before the dose of 24 mg or 48 mg on days 15 and 22 of cycle 1.

2. The method of claim 1, wherein the bispecific antibody is administered at a dose of 24 mg.

3. The method of claim 1, wherein the bispecific antibody is administered at a dose of 48 mg.

4. The method of claim 1, wherein the bispecific antibody is administered once every week (weekly administration) for 2.5 28-day cycles.

5. The method of claim 4, wherein after the weekly administration, the bispecific antibody is administered once every two weeks (biweekly administration) for six 28-day cycles.

6. The method of claim 5, wherein after the biweekly administration, the bispecific antibody is administered once every four weeks for up to two years total duration of treatment with the bispecific antibody from initiation of rituximab and bendamustine.

7. The method of claim 1, wherein the priming dose is 0.16 mg and the intermediate dose is 0.8 mg.

8. The method of claim 1, wherein rituximab is administered once every four weeks for six 28-day cycles.

9. The method of claim 1, wherein bendamustine is administered once a day from day 1 to day 2 for six 28-day cycles.

10. The method of claim 1, wherein rituximab, bendamustine, and the bispecific antibody are administered on the same day.

11. The method of claim 1, wherein administration is performed in 28-day cycles, and wherein:
    (a) the bispecific antibody is administered as follows:
       (i) in cycle 1, a priming dose of 0.16 mg is administered on day 1, an intermediate dose of 0.8 mg is administered on day 8, and a dose of 24 mg is administered on days 15 and 22;
       (ii) in cycles 2 and 3, a dose of 24 mg is administered on days 1, 8, 15, and 22;

(iii) in cycles 4-9, a dose of 24 mg is administered on days 1 and 15; and (iv) in cycle 10 and subsequent cycles, a dose of 24 mg is administered on day 1;

(b) rituximab is administered on day 1 in cycles 1-6; and (c) bendamustine is administered on days 1 and 2 in cycles 1-6.

12. The method of claim 1, wherein administration is performed in 28-day cycles, and wherein:

(a) the bispecific antibody is administered as follows:

(i) in cycle 1, a priming dose of 0.16 mg is administered on day 1, an intermediate dose of 0.8 mg is administered on day 8, and a dose of 48 mg is administered on days 15 and 22;

(ii) in cycles 2 and 3, a dose of 48 mg is administered on days 1, 8, 15, and 22;

(iii) in cycles 4-9, a dose of 48 mg is administered on days 1 and 15; and (iv) in cycle 10 and subsequent cycles, a dose of 48 mg is administered on day 1;

(b) rituximab is administered on day 1 in cycles 1-6; and (c) bendamustine is administered on days 1 and 2 in cycles 1-6.

13. The method of claim 1, wherein rituximab is administered at a dose of 375 mg/m².

14. The method of claim 1, wherein bendamustine is administered at a dose of 90 mg/m².

15. The method of claim 1, wherein the bispecific antibody is administered subcutaneously.

16. The method of claim 1, wherein rituximab and bendamustine are administered intravenously.

17. The method of claim 1, wherein (a) the follicular lymphoma is previously untreated follicular lymphoma;

(b) the subject has grade 1, 2, or 3a untreated follicular lymphoma; and/or (c) the subject has Stage II, III, or IV untreated follicular lymphoma.

18. The method of claim 1, wherein:

(i) the first antigen-binding region of the bispecific antibody comprises a VH region comprising the amino acid sequence of SEQ ID NO: 6, and the VL region comprising the amino acid sequence of SEQ ID NO: 7; and (ii) the second antigen-binding region of the bispecific antibody comprises a VH region comprising the amino acid sequence of SEQ ID NO: 13, and the VL region comprising the amino acid sequence of SEQ ID NO: 14.

19. The method of claim 1, wherein the first binding arm of the bispecific antibody is derived from a humanized antibody and comprises a λ light chain constant region comprising the amino acid sequence set forth in SEQ ID NO: 22 and/or wherein the second binding arm of the bispecific antibody is derived from a human antibody and comprises a κ light chain constant region comprising the amino acid sequence set forth in SEQ ID NO: 23.

20. The method of claim 1, wherein the bispecific antibody is a full-length antibody with a human IgG1 constant region.

21. The method of claim 1, wherein the bispecific antibody comprises an inert Fc region.

22. The method of claim 1, wherein the bispecific antibody comprises a first heavy chain and a second heavy chain, wherein (i) in both the first and second heavy chains, the amino acids in the positions corresponding to positions L234, L235, and D265 in the human IgG1 heavy chain constant region of SEQ ID NO: 15 are F, E, and A, respectively, and (ii) in the first heavy chain, the amino acid in the position corresponding to F405 in the human IgG1 heavy chain constant region of SEQ ID NO: 15 is L, and wherein in the second heavy chain, the amino acid in the position corresponding to K409 in the human IgG1 heavy chain constant region of SEQ ID NO: 15 is R, or vice versa.

23. The method of claim 1, wherein the bispecific antibody comprises heavy chain constant regions comprising the amino acid sequences of SEQ ID NOs: 19 and 20.

24. The method of claim 1, wherein the bispecific antibody comprises a first heavy chain and a first light chain comprising the amino acid sequences set forth in SEQ ID NOs: 24 and 25, respectively, and a second heavy chain and a second light chain comprising the amino acid sequences set forth in SEQ ID NOs: 26 and 27, respectively.

25. The method of claim 1, wherein the bispecific antibody is epcoritamab, or a biosimilar thereof, wherein the biosimilar comprises:

(i) a first binding arm comprising a VH region comprising the CDR1, CDR2 and CDR3 sequences that are in the VH region sequence of SEQ ID NO: 6, and a VL region comprising the CDR1, CDR2 and CDR3 sequences that are in the VL region sequence of SEQ ID NO: 7; and (ii) a second binding arm comprising a VH region comprising the amino acid sequence of SEQ ID NO: 13, and a VL region comprising the amino acid sequence of SEQ ID NO: 14; or (i) a first binding arm comprising a VH region comprising the amino acid sequence of SEQ ID NO: 6, and a VL region comprising the amino acid sequence of SEQ ID NO: 7; and (ii) a second binding arm comprising a VH region comprising the CDR1, CDR2 and CDR3 sequences that are in the VH region sequence of SEQ ID NO: 13, and a VL region comprising the CDR1, CDR2 and CDR3 sequences that are in the VL region sequence of SEQ ID NO: 14.

26. A method of treating follicular lymphoma in a human subject, the method comprising administering to the subject a bispecific antibody and an effective amount of rituximab and bendamustine, wherein the bispecific antibody comprises a first heavy chain and a first light chain comprising the amino acid sequences set forth in SEQ ID NOs: 24 and 25, respectively, and a second heavy chain and a second light chain comprising the amino acid sequences set forth in SEQ ID NOs: 26 and 27, respectively;

wherein the bispecific antibody is administered at a dose of 24 mg, and wherein rituximab, bendamustine, and the bispecific antibody are administered in 28-day cycles, and wherein:

(a) the bispecific antibody is administered as follows:

(i) in cycle 1, a priming dose of 0.16 mg is administered on day 1, an intermediate dose of 0.8 mg is administered on day 8, and a dose of 24 mg is administered on days 15 and 22;

(ii) in cycles 2 and 3, a dose of 24 mg is administered on days 1, 8, 15, and 22;

(iii) in cycles 4-9, a dose of 24 mg is administered on days 1 and 15; and (iv) in cycle 10 and subsequent cycles, a dose of 24 mg is administered on day 1;

(b) rituximab is administered on day 1 in cycles 1-6; and
(c) bendamustine is administered on days 1 and 2 in cycles 1-6.

27. A method of treating follicular lymphoma in a human subject, the method comprising administering to the subject a bispecific antibody and an effective amount of rituximab and bendamustine, wherein the bispecific antibody comprises a first heavy chain and a first light chain comprising the amino acid sequences set forth in SEQ ID NOs: 24 and 25, respectively, and a second heavy chain and a second light chain comprising the amino acid sequences set forth in SEQ ID NOs: 26 and 27, respectively;

wherein the bispecific antibody is administered at a dose of 48 mg, and wherein rituximab, bendamustine, and the bispecific antibody are administered in 28-day cycles, and wherein:

(a) the bispecific antibody is administered as follows:
  (i) in cycle 1, a priming dose of 0.16 mg is administered on day 1, an intermediate dose of 0.8 mg is administered on day 8, and a dose of 48 mg is administered on days 15 and 22;
  (ii) in cycles 2 and 3, a dose of 48 mg is administered on days 1, 8, 15, and 22;
  (iii) in cycles 4-9, a dose of 48 mg is administered on days 1 and 15; and
  (iv) in cycle 10 and subsequent cycles, a dose of 48 mg is administered on day 1;
(b) rituximab is administered on day 1 in cycles 1-6; and
(c) bendamustine is administered on days 1 and 2 in cycles 1-6.

\* \* \* \* \*

UNITED STATES PATENT AND TRADEMARK OFFICE
CERTIFICATE OF CORRECTION

| | | |
|---|---|---|
| PATENT NO. | : 11,535,679 B2 | |
| APPLICATION NO. | : 17/558404 | |
| DATED | : December 27, 2022 | |
| INVENTOR(S) | : Brian Elliott et al. | |

It is certified that error appears in the above-identified patent and that said Letters Patent is hereby corrected as shown below:

In the Claims

At Column 95, Claim number 1, Line 39, delete "region which binds to human CD3c (epsilon) and" and insert --region which binds to human CD3ε (epsilon) and--

At Column 97, Claim number 19, Line number 52, delete "antibody and comprises a λ, light chain constant region" and insert --antibody and comprises a λ light chain constant region--

Signed and Sealed this
Fourteenth Day of February, 2023

*Katherine Kelly Vidal*

Katherine Kelly Vidal
*Director of the United States Patent and Trademark Office*